(12) United States Patent  
Hoischen et al.

(10) Patent No.: US 7,807,703 B2  
(45) Date of Patent: Oct. 5, 2010

(54) SUBSTITUTED ARYL KETONES

(75) Inventors: Dorothee Hoischen, Düsseldorf (DE); Stefan Herrmann, Langenfeld (DE); Kristian Kather, Langenfeld (DE); Klaus-Helmut Müller, Düsseldorf (DE); Hans-Georg Schwarz, Langenfeld (DE); Otto Schallner, Monheim (DE); Mark Wilhelm Drewes, Langenfeld (DE); Peter Dahmen, Neuss (DE); Dieter Feucht, Eschborn (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 1457 days.

(21) Appl. No.: 10/506,644

(22) PCT Filed: Feb. 21, 2003

(86) PCT No.: PCT/EP03/01800

§ 371 (c)(1),  
(2), (4) Date: Feb. 11, 2005

(87) PCT Pub. No.: WO03/074475

PCT Pub. Date: Sep. 12, 2003

(65) Prior Publication Data

US 2005/0153958 A1     Jul. 14, 2005

(30) Foreign Application Priority Data

Mar. 5, 2002   (DE) .................. 102 09 645

(51) Int. Cl.  
*A01N 43/48* (2006.01)  
*A01N 41/06* (2006.01)  
*A01N 25/00* (2006.01)  
*C07D 231/00* (2006.01)  
*C07C 311/00* (2006.01)

(52) U.S. Cl. .............. 514/406; 514/407; 514/604; 548/369.4; 564/88; 424/405

(58) Field of Classification Search ........... 514/406, 514/407, 604; 564/88; 548/369.4  
See application file for complete search history.

(56) References Cited

U.S. PATENT DOCUMENTS

| | | | |
|---|---|---|---|
| 4,780,127 A | 10/1988 | Michaely et al. | 71/103 |
| 4,806,146 A | 2/1989 | Carter | 71/98 |
| 4,816,066 A | 3/1989 | Michaely et al. | 71/123 |
| 4,946,981 A | 8/1990 | Carter et al. | 558/415 |
| 4,986,845 A * | 1/1991 | Oya et al. | 504/196 |
| 5,006,162 A | 4/1991 | Carter | 71/123 |
| 5,085,688 A | 2/1992 | Michaely et al. | 71/103 |
| 5,110,343 A | 5/1992 | Ueda et al. | 71/88 |
| RE34,779 E | 11/1994 | Oya et al. | 504/282 |
| 5,371,063 A | 12/1994 | Cramp et al. | 504/270 |
| 5,374,606 A | 12/1994 | Cramp et al. | 504/270 |
| 5,489,570 A | 2/1996 | Geach et al. | 504/261 |
| 5,650,533 A | 7/1997 | Roberts et al. | 560/17 |
| 5,656,573 A | 8/1997 | Roberts et al. | 504/271 |
| 5,747,424 A | 5/1998 | Roberts et al. | 504/271 |
| 5,804,532 A | 9/1998 | Cain et al. | 504/309 |
| 5,834,402 A | 11/1998 | Von Deyn et al. | 504/271 |
| 5,846,906 A | 12/1998 | von Deyn et al. | 504/221 |
| 5,846,907 A | 12/1998 | von Deyn et al. | 504/221 |
| 5,859,283 A | 1/1999 | Cramp | 560/124 |
| 5,863,865 A | 1/1999 | Lee et al. | 504/271 |

(Continued)

FOREIGN PATENT DOCUMENTS

| | | |
|---|---|---|
| CA | 2257196 | 12/1997 |
| CA | 2338304 | 2/2000 |
| CA | 2 252 543 | 1/2003 |
| CA | 2 075 348 C | 10/2003 |
| DE | 198 46 792 | 4/2000 |
| EP | 0 186 119 B1 | 8/1989 |
| WO | 95/31446 | 11/1995 |
| WO | 97/27187 | 7/1997 |
| WO | 98/28981 | 7/1998 |
| WO | 99/03856 | 1/1999 |

*Primary Examiner*—Sharmila Gollamudi Landau  
*Assistant Examiner*—Kortney L Klinkel  
(74) *Attorney, Agent, or Firm*—Baker Donelson Bearman, Caldwell & Berkowitz, PC

(57) ABSTRACT

The invention relates to novel aryl ketones of the formula (I)

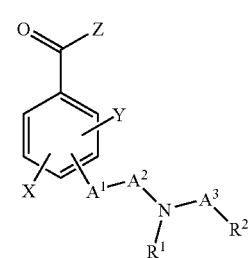

(I)

in which  
Z represents the groups

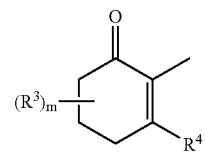 or 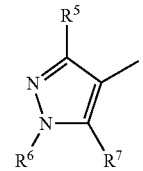

and  
$A^1$, $A^2$, $A^3$, $R^1$, $R^2$, $R^3$, $R^4$, $R^5$, $R^6$, $R^7$, X, Y, and m are as defined in the disclosure,  
to their use as pesticides, in particular herbicides, and to processes and intermediates for their preparation.

11 Claims, No Drawings

U.S. PATENT DOCUMENTS

| | | | |
|---|---|---|---|
| 5,948,917 A | 9/1999 | Adachi et al. | 548/274 |
| 6,004,903 A | 12/1999 | von Deyn et al. | 504/239 |
| 6,124,469 A | 9/2000 | Rheinheimer et al. | 548/240 |
| 6,153,759 A | 11/2000 | von Deyn et al. | 548/131 |
| 6,156,702 A | 12/2000 | Engel et al. | 504/282 |
| 6,165,944 A | 12/2000 | von Deyn et al. | 504/271 |
| 6,207,618 B1 | 3/2001 | Engel et al. | 504/282 |
| 6,218,579 B1 | 4/2001 | Jones et al. | 568/309 |
| 6,297,198 B1 | 10/2001 | Lee | 504/271 |
| 6,376,429 B1 * | 4/2002 | Van Almsick et al. | 504/271 |
| 6,432,881 B1 | 8/2002 | Engel et al. | 504/280 |
| 6,559,100 B1 | 5/2003 | Engel et al. | 504/223 |
| 6,864,219 B2 | 3/2005 | Schallner et al. | 504/273 |
| 2002/0025910 A1 | 2/2002 | Deyn et al. | 504/263 |
| 2003/0153465 A1 | 8/2003 | Schallner et al. | 504/271 |
| 2004/0176253 A1 | 9/2004 | Hermann et al. | 504/322 |
| 2005/0009704 A1 | 1/2005 | Schallner et al. | 504/271 |

* cited by examiner

SUBSTITUTED ARYL KETONES

The present patent application has been filed under 35 U.S.C. 371 as a national stage application of PCT/EP03/01800, filed Feb. 21, 2003, which was published in German as International Patent Publication WO 03/074475 on Sep. 12, 2003, which is entitled to the right of priority of German Patent Application 102 09 645.7, filed Mar. 5, 2002.

The invention relates to novel substituted aryl ketones, to a process for their preparation and to their use as crop treatment agents, in particular herbicides.

It is already known that certain substituted aryl ketones have herbicidal properties (cf. EP-A-090 262, EP-A-135 191, EP-A-186 118, EP-A-186 119, EP-A-186 120, EP-A-319 075, EP-A-352 543, EP-A-418 175, EP-A-487 357, EP-A-527 036, EP-A-527 037, EP-A-560 483, EP-A-609 797, EP-A-609 798, EP-A-625 505, EP-A-625 508, EP-A-636 622, U.S. Pat. No. 5,804,532, U.S. Pat. No. 5,834,402, U.S. Pat. No. 5,846,906, U.S. Pat. No. 5,863,865, WO-A-95/31446, WO-A-96/26192, WO-A-96/26193, WO-A-96/26200, WO-A-96/26206, WO-A-97/27187, WO-A-97/35850, WO-A-97/41105, WO-A-97/41116, WO-A-97/41117, WO-A-97/41118, WO-A-97/43270, WO-A-97/46530, WO-A-98/28981, WO-A-98/31681, WO-A-98/31682, WO-A-99/03856, WO-A-99/07688, WO-A-99/07697, WO-A-99/10327, WO-A-99/10328, WO-A-00/05221, WO-A-00/21924). However, the activity of these compounds is not entirely satisfactory.

This invention now provides the novel substituted aryl ketones of the formula (I)

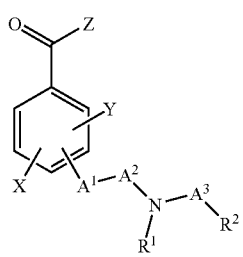

(I)

in which $A^1$ represents a single bond, represents O (oxygen), S (sulphur) or the grouping

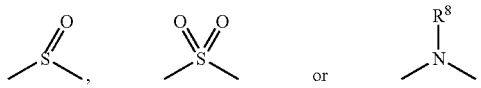

where $R^8$ represents hydrogen, represents in each case optionally substituted alkyl, alkylcarbonylalkyl, alkoxycarbonylalkyl, alkylthio, alkylsulphinyl, alkylsulphonyl, alkenyl, alkenylcarbonylalkyl, alkenyloxycarbonylalkyl, alkynyl, alkynylcarbonylalkyl, alkynyloxycarbonylalkyl, cycloalkyl, cycloalkylcarbonylalkyl, cycloalkyloxycarbonylalkyl, cycloalkylalkyl, cycloalkylalkylcarbonylalkyl, cycloalkylalkoxycarbonylalkyl, aryl, arylcarbonylalkyl, aryloxycarbonylalkyl, arylalkyl, arylalkylcarbonylalkyl or arylalkoxycarbonylalkyl, $A^2$ represents alkanediyl (alkylene), alkenediyl or alkynediyl, $A^3$ represents O (oxygen), S (sulphur), or the grouping

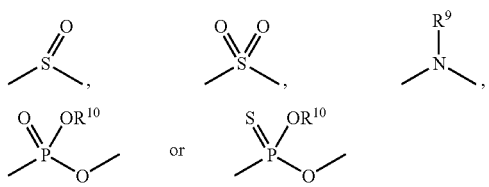

where $R^9$ represents hydrogen or represents in each case optionally substituted alkyl, alkylcarbonyl, alkoxycarbonyl, alkylthio, alkylsulphinyl, alkylsulphonyl, alkenyl, alkenylcarbonyl, alkenyloxycarbonyl, alkynyl, alynylcarbonyl, alkynyloxycarbonyl, cycloalkyl, cycloalkylcarbonyl, cycloalkyloxycarbonyl, cycloalkylalkyl, cycloalkylalkylcarbonyl, cycloalkylalkoxycarbonyl, aryl, arylcarbonyl, aryloxycarbonyl, arylalkyl, arylalkylcarbonyl, arylalkoxycarbonyl, heterocyclyl, heterocyclylcarbonyl or heterocyclylalkyl, or $R^9$ together with $R^2$ and the nitrogen to which they are attached represents an optionally substituted heterocycle, $R^{10}$ represents hydrogen, represents formyl or represents in each case optionally substituted alkyl, alkylcarbonyl, alkoxycarbonyl, alkylaminocarbonyl, dialkylaminocarbonyl, alkenyl, alkenylcarbonyl, alkenyloxycarbonyl, alkynyl, alkynylcarbonyl, alkynyloxycarbonyl, cycloalkyl, cycloalkylcarbonyl, cycloalkyloxycarbonyl, cycloalkylaminocarbonyl, cycloalkylalkyl, aryl, arylcarbonyl, aryloxycarbonyl, arylaminocarbonyl, arylalkyl, arylalkylcarbonyl, arylalkoxycarbonyl, heterocyclyl, heterocyclylcarbonyl or heterocyclylalkyl, $R^1$ represents hydrogen or represents in each case optionally substituted alkyl, alkylthio, alkylsulphinyl, alkylsulphonyl, alkenyl, alkynyl, cycloalkyl, cycloalkylalkyl, aryl, arylalkyl, arylcarbonylalkyl, heterocyclyl, or heterocyclylalkyl, $R^2$ represents hydrogen, represents formyl or represents in each case optionally substituted alkyl, alkylcarbonyl, alkoxycarbonyl, alkylaminocarbonyl, dialkylaminocarbonyl, alkenyl, alkenylcarbonyl, alkenyloxycarbonyl, alkynyl, alkynylcarbonyl, alkynyloxycarbonyl, cycloalkyl, cycloalkylcarbonyl, cycloalkyloxycarbonyl, cycloalkylaminocarbonyl, cycloalkylalkyl, aryl, arylcarbonyl, aryloxycarbonyl, arylaminocarbonyl, arylalkyl, arylalkylcarbonyl, arylalkoxycarbonyl, heterocyclyl, heterocyclylcarbonyl or heterocyclylalkyl, X represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, Y represents hydrogen, nitro, cyano, carboxyl, carbamoyl, thiocarbamoyl, halogen, or represents in each case optionally substituted alkyl, alkoxy, alkylthio, alkylsulphinyl, alkylsulphonyl, alkylamino, dialkylamino or dialkylaminosulphonyl, and Z represents one of the groupings below

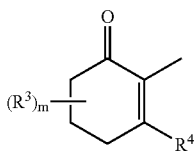
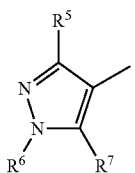

where
m represents the numbers 0 to 6,
$R^3$ represents hydrogen, halogen or represents in each case optionally substituted alkyl, alkylthio or aryl, or—if m represents 2—optionally also together with a second radical $R^3$ represents oxygen or alkanediyl (alkylene),
$R^4$ represents hydroxyl, formyloxy, halogen, or represents in each case optionally substituted alkoxy, cycloalkoxy, alkylthio, cycloalkylthio, alkylsulphinyl, alkylsulphonyl, alkylcarbonyloxy, alkoxycarbonyloxy, alkylaminocarbonyloxy, alkylsulphonyloxy, alkenyloxy, alkynyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, arylalkylsulphonyl or heterocyclyl which contains at least one nitrogen atom and is attached via nitrogen,
$R^5$ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl,
$R^6$ represents hydrogen or represents in each case optionally substituted alkyl, alkenyl, alkynyl, cycloalkyl, cycloalkylalkyl, aryl or arylalkyl, and
$R^7$ represents hydroxyl, formyloxy, or represents in each case optionally substituted alkoxy, cycloalkoxy, alkylcarbonyloxy, alkoxycarbonyloxy, alkoxycarbonylalkoxy, alkylaminocarbonyloxy, alkylsulphonyloxy, alkenyloxy, alkynyloxy, arylalkoxy, arylcarbonyloxy, arylcarbonylalkoxy, arylsulphonyloxy or aminocarbonyloxy.

Unless indicated otherwise, the following definitions apply in the definitions above and below:

Saturated or unsaturated hydrocarbon chains, such as alkyl, alkanediyl, alkenyl or alkynyl, are in each case straight-chain or branched, including in combination with heteroatoms, such as, for example, in alkoxy, alkylthio or alkylamino. Unless indicated otherwise, preference is given to hydrocarbon chains having 1 to 6 carbon atoms.

Cycloalkyl represents saturated carbocyclic compounds which, if appropriate, form a polycyclic ring system with further carbocyclic fused-on or bridged rings. Unless indicated otherwise, preference is given to cyclopropyl, cyclopentyl and cyclohexyl.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated, unsaturated or aromatic cyclic compounds in which at least one ring member is a heteroatom, i.e. an atom different from carbon. If the ring contains a plurality of heteroatoms, these can be identical or different. Preferred heteroatoms are oxygen, nitrogen and sulphur. If this ring contains a plurality of oxygen atoms, these are not adjacent. If appropriate, the cyclic compounds form a polycyclic ring system with further carbocyclic or heterocyclic fused-on or bridged rings. A polycyclic ring system may be attached via the heterocyclic ring or a fused-on carbocyclic ring. Preference is given to mono- or bicyclic ring systems, in particular to monocyclic ring systems having 5 or 6 ring members and bicyclic ring systems having 7 to 9 ring members.

If the compounds of the general formula (I) can exist in different tautomeric or stereoisomeric forms, the invention includes the tautomeric and stereoisomeric forms possible in each case.

Preferred substituents or preferred ranges of the radicals present in the formulae listed above and below are defined below.

$A^2$ preferably represents alkanediyl having 1 to 6 carbon atoms, alkenediyl or alkynediyl having in each case 2 to 6 carbon atoms.

$R^1$ preferably represents hydrogen,
represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, di($C_1$-$C_4$-alkyl) amino-, di($C_1$-$C_4$-alkyl)aminocarbonyl- or N—($C_1$-$C_4$-alkoxy)-N—($C_1$-$C_4$-alkyl)aminocarbonyl-substituted alkyl having 1 to 6 carbon atoms, represents in each case optionally halogen-substituted alkylthio, alkylsulphinyl or alkylsulphonyl having in each case 1 to 6 carbon atoms, represents in each case optionally halogen-substituted alkenyl or alkynyl having in each case 2 to 6 carbon atoms,
represents in each case optionally cyano-, halogen- or $C_1$-$C_4$-alkyl-substituted cycloalkyl, cycloalkylalkyl having in each case 3 to 6 carbon atoms in the cycloalkyl groups and, if appropriate, 1 to 4 carbon atoms in the alkyl moiety,
represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl, arylalkyl or arylcarbonylalkyl having in each case 6 or 10 carbon atoms in the aryl groups and, if appropriate, 1 to 4 carbon atoms in the alkyl moiety, or
represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted heterocyclyl or heterocyclylalkyl where in each case the heterocyclyl grouping contains up to 10 carbon atoms and additionally at least one heteroatom selected from the group consisting of N (nitrogen, but at most 5 N atoms), O (oxygen, but at most 2 O atoms), S (sulphur, but at most 2 S atoms), SO and $SO_2$, and optionally additionally one group selected from the group consisting of oxo (C=O), thioxo (C=S), imino (C=NH), cyanoimino (C=N—CN), nitroimino (C=N—$NO_2$).

$R^2$ preferably represents hydrogen, represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylamino-carbonyl- or di($C_1$-$C_4$-alkyl)aminocarbonyl-substituted alkyl having 1 to 6 carbon atoms,
represents in each case optionally cyano-, halogen- or $C_1$-$C_4$-alkoxy-substituted alkylcarbonyl, alkoxycarbonyl or alkylaminocarbonyl having in each case 1 to 6 carbon atoms in the alkyl groups,
represents dialkylaminocarbonyl having in each case 1 to 4 carbon atoms in the alkyl groups,
represents in each case optionally halogen-substituted alkenyl, alkenylcarbonyl, alkenyloxycarbonyl, alkynyl, alkynylcarbonyl or alkynyloxycarbonyl having in each case 3 to 6 carbon atoms in the alkenyl or alkynyl groups,
represents in each case optionally cyano-, halogen- or $C_1$-$C_4$-alkyl-substituted cycloalkyl, cycloalkylcarbonyl, cycloalkyloxycarbonyl, cycloalkylalkyl, cycloalkylalkylcarbonyl or cycloalkylalkoxycarbonyl having in each case 3 to 6 carbon atoms in the cycloalkyl groups and, if appropriate, 1 to 4 carbon atoms in the alkyl moiety, represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl, arylcarbonyl, aryloxycarbonyl, arylaminocarbonyl, arylalkyl, arylalkylcarbonyl, arylalkoxycarbonyl or arylalkylaminocarbonyl having in each case 6 or 10 carbon atoms in the aryl groups and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted heterocyclyl, heterocyclylcarbonyl or heterocyclylalkyl, where the heterocyclyl group contains in each case up to 10 carbon atoms and additionally at least one heteroatom selected from the group consisting of N (nitrogen, but at most 5 N atoms), O (oxygen, but at most 2 O atoms), S (sulphur, but at most 2 S atoms), SO and $SO_2$, and optionally additionally one group selected from the group consisting of oxo (C=O), thioxo (C=S), imino (C=NH), cyanoimino (C=N—CN), nitroimino (C=N—$NO_2$).

$R^3$ preferably represents hydrogen, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl or alkylthio having in each case 1 to 6 carbon atoms, or represents phenyl, or—if m represents 2—optionally also together with a second radical $R^3$ represents oxygen or alkanediyl (alkylene) having 3 to 5 carbon atoms.

$R^4$ preferably represents hydroxyl, formyloxy, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy or alkylsulphonyloxy having in each case 1 to 6 carbon atoms, represents in each case optionally halogen-substituted alkenyloxy or alkynyloxy having in each case 3 to 6 carbon atoms, represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl group and, if appropriate, 1 to 4 carbon atoms in the alkyl moiety, represents in each case optionally cyano-, halogen-, oxo-, hydroxyl-, $C_1$-$C_4$-alkoxy-, $C_1$-$C_4$-alkyl-substituted heterocyclyl having 5 or 6 ring atoms comprising at least 1 nitrogen atom and optionally up to 2 oxygen atoms, sulphur atoms and 3 nitrogen atoms, where in total not more than 4 heteroatoms are present and where the heterocycle is attached via the nitrogen.

$R^5$ preferably represents hydrogen, cyano, carbamoyl, thiocarbamoyl, halogen, represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl or alkoxycarbonyl having in each case 1 to 6 carbon atoms in the alkyl groups, or represents optionally cyano-, halogen- or $C_1$-$C_4$-alkyl-substituted cycloalkyl having 3 to 6 carbon atoms.

$R^6$ preferably represents hydrogen, represents optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl having 1 to 6 carbon atoms, represents in each case optionally cyano- or halogen-substituted alkenyl or alkynyl having in each case 3 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted aryl or arylalkyl having in each case 6 or 10 carbon atoms in the aryl group and, if appropriate, 1 to 4 carbon atoms in the alkyl moiety.

$R^7$ preferably represents hydroxyl, formyloxy, represents in each case optionally alkyl-, cyano-, halogen- or $C_1$-$C_4$-alkoxy-substituted alkoxy, alkylcarbonyloxy, alkoxycarbonyloxy, alkoxycarbonylalkoxy, alkylaminocarbonyloxy or alkylsulphonyloxy having in each case 1 to 6 carbon atoms in the alkyl groups, represents in each case optionally cyano- or halogen-substituted alkenyloxy or alkynyloxy having in each case 3 to 6 carbon atoms, or represents in each case optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-$C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- or $C_1$-$C_4$-haloalkylsulphonyl-substituted arylalkoxy, arylcarbonyloxy, arylcarbonylalkoxy or arylsulphonyloxy having in each case 6 or 10 carbon atoms in the aryl group and, if appropriate, 1 to 4 carbon atoms in the alkyl moiety.

$R^8$ preferably represents hydrogen, represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl- or di($C_1$-$C_4$-alkyl)aminocarbonyl-substituted alkyl having 1 to 6 carbon atoms, represents in each case optionally cyano-, halogen- or $C_1$-$C_4$-alkoxy-substituted alkylcarbonyl or alkoxycarbonyl having in each case 1 to 6 carbon atoms in the alkyl groups, represents in each case optionally halogen-substituted alkylthio, alkylsulphinyl or alkylsulphonyl having in each case 1 to 6 carbon atoms, represents in each case optionally halogen-substituted alkenyl, alkenylcarbonyl, alkenyloxycarbonyl, alkynyl, alkynylcarbonyl or alkynyloxycarbonyl having in each case 2 to 6 carbon atoms in the alkenyl or alkynyl groups, represents in each case optionally cyano-, halogen- or $C_1$-$C_4$-alkyl-substituted cycloalkyl, cycloalkylcarbonyl, cycloalkyloxycarbonyl, cycloalkylalkyl, cycloalkylalkylcarbonyl or cycloalkylalkoxycarbonyl having in each case 3 to 6 carbon atoms in the cycloalkyl groups and, if appropriate, 1 to 4 carbon atoms in the alkyl moiety, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl, arylcarbonyl, aryloxycarbonyl, arylalkyl, arylalkylcarbonyl or arylalkoxycarbonyl having in each case 6 or 10 carbon atoms in the aryl groups and, if appropriate, 1 to 4 carbon atoms in the alkyl moiety.

$R^9$ preferably represents hydrogen,
  represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxycarbonyl-, $C_1$-$C_4$-alkylamino-carbonyl or di($C_1$-$C_4$-alkyl)aminocarbonyl-substituted alkyl having 1 to 6 carbon atoms,
  represents in each case optionally cyano-, halogen- or $C_1$-$C_4$-alkoxy-substituted alkylcarbonyl or alkoxycarbonyl having in each case 1 to 6 carbon atoms in the alkyl groups,
  represents in each case optionally halogen-substituted alkylthio, alkylsulphinyl or alkylsulphonyl having in each case 1 to 6 carbon atoms,
  represents in each case optionally halogen-substituted alkenyl, alkenylcarbonyl, alkenyloxycarbonyl, alkynyl, alkynylcarbonyl or alkynyloxycarbonyl having in each case 2 to 6 carbon atoms in the alkenyl or alkynyl groups,
  represents in each case optionally cyano-, halogen- or $C_1$-$C_4$-alkyl-substituted cycloalkyl, cycloalkylcarbonyl, cycloalkyloxycarbonyl, cycloalkylalkyl, cycloalkylalkylcarbonyl or cycloalkylalkoxycarbonyl having in each case 3 to 6 carbon atoms in the cycloalkyl groups and, if appropriate, 1 to 4 carbon atoms in the alkyl moiety,
  represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl, arylcarbonyl, aryloxycarbonyl, arylalkyl, arylalkylcarbonyl or arylalkoxycarbonyl having in each case 6 or 10 carbon atoms in the aryl groups and, if appropriate, 1 to 4 carbon atoms in the alkyl moiety, or
  represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted heterocyclyl, heterocyclylcarbonyl or heterocyclylalkyl, where in each case the heterocyclyl grouping contains up to 10 carbon atoms and additionally at least one heteroatom selected from the group consisting of N (but at most 5 N atoms), O (but at most 2 O atoms), S (but at most 2 S atoms), SO and $SO_2$, and optionally additionally one group selected from the group consisting of oxo (C=O), thioxo (C=S), imino (C=NH), cyanoimino (C=N—CN), nitroimino (C=N—$NO_2$), or
  together with $R^2$ and the nitrogen to which they are attached represents an optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted heterocycle which contains 1 nitrogen atom and 1 to 10 carbon atoms and optionally one further heteroatom from the group consisting of N (but at most 4 further N atoms), O (but at most 2 O atoms), S (but at most 2 S atoms), SO and $SO_2$, and optionally additionally one group selected from the group consisting of oxo (C=O), thioxo (C=S), imino (C=NH), cyanoimino (C=N—CN), nitroimino (C=N—$NO_2$),
$R^{10}$ preferably represents hydrogen, formyl,
  represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl- or di-($C_1$-$C_4$-alkyl)-amino-carbonylsubstituted alkyl having 1 to 6 carbon atoms.
X preferably represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.
Y preferably represents hydrogen, nitro, cyano, carboxyl, carbamoyl, thiocarbamoyl, halogen, or represents in each case optionally cyano-, halogen-, $C_1$-$C_4$-alkoxy-, $C_1$-$C_4$-alkylthio-, $C_1$-$C_4$-alkylsulphinyl- or $C_1$-$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.
m preferably represents the numbers 0 to 3.
$A^2$ particularly preferably represents methylene (—$CH_2$—), ethane-1,1-diyl (—CH($CH_3$)—), ethane-1,2-diyl (dimethylene, —$CH_2CH_2$—), propane-1,1-diyl (—CH($C_2H_5$)—), propane-1,2-diyl (—CH($CH_3$)$CH_2$—), propane-1,3-diyl (—$CH_2CH_2CH_2$—), butane-1,3-diyl (—CH($CH_3$)$CH_2CH_2$—), butane-1,4-diyl (—$CH_2CH_2CH_2CH_2$—), ethenediyl, propenediyl, butenediyl, ethynediyl, propynediyl or butynediyl.
$R^1$ particularly preferably represents hydrogen,
  represents in each case optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylamino-, diethylamino-, dimethylaminocarbonyl-, diethylaminocarbonyl- or N-methoxy-N-methylaminocarbonyl-substituted methyl, ethyl, n- or i-propyl, n-, i- or s-butyl, n-, i- or s-pentyl,
  represents in each case optionally fluorine- and/or chlorine-substituted methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl,
  represents in each case optionally fluorine-, chlorine- and/or bromine-substituted propenyl, butenyl, propynyl or butynyl,
  represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl,
  represents in each case optionally cyano-, nitro-, fluorine-, chlorine-, bromine-, methyl-, ethyl-, n- or i-propyl-, n-, i-, s- or t-butyl, trifluoromethyl-, methoxy-, ethoxy-, s- or i-propoxy-, n-, i-, s- or t-butoxy-, difluoromethoxy- or trifluoromethoxy-substituted phenyl, benzoyl, benzyl, phenylethyl or phenylcarbonylmethyl, or
  represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl or heterocyclylalkyl from the group consisting of furyl, furylmethyl, thienyl, thienylmethyl, pyrrolidinyl, oxopyrrolidinyl, pyrrolyl, indolyl, pyrrolylmethyl, pyrazolyl, pyrazolylmethyl, oxazolyl, oxazolylmethyl, isoxazolyl, thiazolyl, thiazolylmethyl, dihydropyranyl, dihydropyranylmethyl, piperidinyl, oxopiperidinyl, morpholinyl, piperazinyl, pyridinyl, pyridinylcarbonyl or pyridinylmethyl.
$R^2$ particularly preferably represents hydrogen,
  represents in each case optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylaminocarbonyl-substituted methyl, ethyl, n- or i-propyl, n-, i-, s- or t-butyl, n-, i-, s- or t-pentyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, represents dimethylaminocarbonyl, diethylaminocarbonyl or dipropylaminocarbonyl, represents in each case optionally fluorine-, chlorine- and/or bromine-substituted propenyl, butenyl, propenylcarbonyl, butenylcarbonyl, propenyloxycarbonyl, butenyloxycarbonyl, propenylaminocarbonyl, butenylaminocarbonyl, propynyl, butynyl, propynylcarbonyl, butynylcarbonyl, propynyloxycarbonyl or butynyloxycarbonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, cyclohexylmethoxycarbonyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, naphthyl, benzoyl, phenoxycarbonyl, phenylaminocarbonyl, benzyl, phenylethyl, phenylmethylcarbonyl or phenylmethoxycarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted furyl, furylcarbonyl, furylmethyl, thienyl, thienylcarbonyl, thienylmethyl, pyrrolidinyl, oxopyrrolidinyl, pyrrolyl, indolyl, pyrrolylmethyl, pyrazolyl, pyrazolylcarbonyl, pyrazolylmethyl, oxazolyl, oxazolylmethyl, isoxazolyl, isoxazolylcarbonyl, thiazolyl, thiazolylmethyl, 2-oxo-1,3-diazacyclopentyl (2-oxoimidazolidinyl), piperidinyl, oxopiperidinyl, 2-oxo-1,3-diazacyclohexyl, morpholinyl, thiomorpholinyl, 3-oxomorpholinyl, 3-oxothiomorpholinyl, piperazinyl, pyridinyl, pyridinylcarbonyl or pyridinylmethyl.

$R^3$ particularly preferably represents hydrogen, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methylthio, ethylthio, n- or i-propylthio, n-, i-, s- or t-butylthio, or represents phenyl, or—if m represents 2—optionally also together with a second radical $R^3$ represents oxygen, propane-1,3-diyl or butane-1,4-diyl.

$R^4$ particularly preferably represents hydroxyl, formyloxy, fluorine or chlorine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine-, chlorine- and/or bromine-substituted propenyloxy, butenyloxy, propynyloxy or butynyloxy, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl, represents in each case optionally cyano-, oxo-, fluorine-, chlorine-, methyl-, ethyl-, methoxy-, ethoxy-, methylthio-, ethylthio-substituted pyrrolyl, pyrrolinyl, pyrrolidinyl, pyrazolyl, pyrazolinyl, pyrazolidinyl, imidazolyl, imidazolinyl, imidazolidinyl, triazolyl, triazolinyl, triazolidinyl, tetrazolyl, tetrazolinyl, tetrazolidinyl, oxazolyl, oxazolinyl, oxazolidinyl, isoxazolyl, isoxazolinyl, isoxazolidinyl, thiazolyl, thiazolinyl, thiazolidinyl, thiadiazolyl, indolyl, piperidinyl, piperazinyl, oxazinyl, thiazinyl, morpholinyl.

$R^5$ particularly preferably represents hydrogen, cyano, carbamoyl, thiocarbamoyl, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents in each case optionally cyano-, fluorine-, chlorine-, methyl- or ethyl-substituted cyclopropyl, cyclobutyl, cyclopentyl or cyclohexyl.

$R^6$ particularly preferably represents hydrogen, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, represents in each case optionally cyano-, fluorine-, chlorine- or bromine-substituted propenyl, butenyl, propynyl or butynyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio, n-, i-, s- or t-butylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyl or phenylmethyl.

$R^7$ particularly preferably represents hydroxyl, formyloxy, represents in each case optionally alkyl-, cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, ethoxycarbonylmethoxy, methoxycarbonylmethoxy, methylsulphonyloxy, ethylsulphonyloxy, n- or i-propylsulphonyloxy, represents in each case optionally cyano-, fluorine-, chlorine- or bromine-substituted propenyloxy, butenyloxy, propynyloxy or butynyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

$R^8$ particularly preferably represents hydrogen, represents in each case optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylaminocarbonyl-substituted methyl, ethyl, n- or i-propyl, n-, i- or s-butyl, n-, i- or s-pentyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, represents in each case optionally fluorine- and/or chlorine-substituted methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents in each case optionally fluorine-, chlorine- and/or bromine-substituted propenyl, butenyl, propenylcarbonyl, butenylcarbonyl, propenyloxycarbonyl, butenyloxycarbonyl, propynyl, butynyl, propynylcarbonyl, butynylcarbonyl, propynyloxycarbonyl or butynyloxycarbonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropyloxycarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, cyclohexylmethoxycarbonyl, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, s- or i-propoxy-, n-, i-, s- or t-butoxy-, difluoromethoxy- or trifluoromethoxy-substituted phenyl, benzoyl, phenoxycarbonyl, benzyl, phenylethyl, phenylmethylcarbonyl or phenylmethoxycarbonyl.

$R^9$ particularly preferably represents hydrogen, represents in each case optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl- or diethylaminocarbonyl-substituted methyl, ethyl, n- or i-propyl, n-, i- or s-butyl, n-, i- or s-pentyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, represents in each case optionally fluorine- and/or chlorine-substituted methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, represents in each case optionally fluorine-, chlorine- and/or bromine-substituted propenyl, butenyl, propenylcarbonyl, butenylcarbonyl, propenyloxycarbonyl, butenyloxycarbonyl, propynyl, butynyl, propynylcarbonyl, butynylcarbonyl, propynyloxycarbonyl or butynyloxycarbonyl, represents in each case optionally cyano-, fluorine-, chlorine-, methyl- or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropyloxycarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, cyclohexylmethoxycarbonyl, represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, s- or i-propoxy-, n-, i-, s- or t-butoxy-, difluoromethoxy- or trifluoromethoxy-substituted phenyl, benzoyl, phenoxycarbonyl, benzyl, phenylethyl, phenylmethylcarbonyl or phenylmethoxycarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl, heterocyclylcarbonyl and heterocyclylalkyl from the group consisting of furyl, furylcarbonyl, furylmethyl, thienyl, thienylcarbonyl, thienylmethyl, pyrrolidinyl, oxopyrrolidinyl, pyrrolyl, indolyl, pyrrolylmethyl, pyrazolyl, pyrazolylcarbonyl, pyrazolylmethyl, oxazolyl, oxazolylmethyl, isoxazolyl, isoxazolylcarbonyl, thiazolyl, thiazolylmethyl, piperidinyl, oxopiperidinyl, morpholinyl, piperazinyl, pyridinyl, pyridinylcarbonyl or pyridinylmethyl, or together with $R^2$ and the nitrogen to which they are attached represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted pyrrolidinyl, oxopyrrolidinyl, pyrrolyl, indolyl, pyrazolyl, oxazolyl, isoxazolyl, dihydropyranyl, piperidinyl, thiomorpholinyl, 3-oxomorpholinyl, 3-oxothiomorpholinyl, oxopiperidinyl, morpholinyl, piperazinyl, imidazolyl, imidazolidinyl, oxo-imidazolidinyl, triazol, triazolinyl, tetrazolinyl or pyridinyl.

$R^{10}$ particularly preferably represents hydrogen, formyl,
represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl- or di($C_1$-$C_4$-alkyl)aminocarbonyl-substituted alkyl having 1 to 6 carbon atoms.

X particularly preferably represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

Y particularly preferably represents hydrogen, nitro, cyano, carboxyl, carbamoyl, thiocarbamoyl, fluorine, chlorine, bromine, iodine, or represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

m particularly preferably represents the numbers 0, 1 or 2.

$A^2$ very particularly preferably represents methylene (—$CH_2$—), ethane-1,1-diyl (—CH($CH_3$)—), ethane-1,2-diyl (dimethylene, —$CH_2CH_2$—), propane-1,2-diyl (—CH($CH_3$)$CH_2$—) or propane-1,3-diyl (—$CH_2CH_2CH_2$—).

$R^1$ very particularly preferably represents hydrogen,
represents in each case optionally cyano-, fluorine-, chlorine-, methoxy-, ethoxy-, n- or i-propoxy-, acetyl-, propionyl-, methoxycarbonyl- or ethoxycarbonyl-substituted methyl, ethyl, n- or i-propyl,
represents in each case optionally cyano-, fluorine-, chlorine-, methoxy-, ethoxy-, n- or i-propoxy-substituted acetyl, propionyl, methoxycarbonyl or ethoxycarbonyl,
represents in each case optionally fluorine and/or chlorine-substituted methylthio, ethylthio, n- or i-propylthio, n-, i-, s- or t-butylthio, methylsulphinyl, ethylsulphinyl, methylsulphonyl or ethylsulphonyl,
represents in each case optionally fluorine-, chlorine- and/or bromine-substituted propenyl, butenyl, propynyl or butynyl,
represents in each case optionally fluorine-, chlorine- or methyl-substituted cyclopropyl, cyclopropylcarbonyl or cyclopropylmethyl, or
represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, s- or i-propoxy-, difluoromethoxy- or trifluoromethoxy-substituted phenyl, benzoyl, phenoxycarbonyl, benzyl, phenylmethylcarbonyl or phenylmethoxycarbonyl.

$R^2$ very particularly preferably represents hydrogen,
represents in each case optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl, ethyl, n- or i-propyl, n-, i-, s- or t-butyl, n-, i-, s- or t-pentyl,
represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, represents dimethylaminocarbonyl,
represents in each case optionally fluorine- and/or chlorine-substituted methylthio, ethylthio, n- or i-propylthio, n-, i-, s- or t-butylthio, methylsulphinyl, ethylsulphinyl, methylsulphonyl or ethylsulphonyl, represents in each case optionally fluorine-, chlorine- and/or bromine-substituted propenyl, butenyl, propynyl or butynyl,
represents in each case optionally fluorine-, chlorine- or methyl-substituted cyclopropyl, cyclopropylcarbonyl or cyclopropylmethyl,
represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, benzoyl, phenoxycarbonyl, phenylaminocarbonyl, benzyl, phenylmethylcarbonyl or phenylmethoxycarbonyl, or
represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl, heterocyclylcarbonyl or heterocyclylalkyl from the group consisting of furyl, furylcarbonyl, furylmethyl, thienyl, thienylcarbonyl, thienylmethyl, pyrrolidinyl, pyrrolyl, indolyl, pyrrolylmethyl, pyrazolyl, pyrazolylmethyl, isoxazolyl, piperidinyl, morpholinyl, thiomorpholinyl, 3-oxomorpholinyl, 3-oxothiomorpholinyl, piperazinyl, pyridinyl, pyridinylmethyl.

$R^3$ very particularly preferably represents hydrogen, represents in each case optionally fluorine- and/or chlorine-substituted methyl, ethyl, n- or i-propyl, methylthio, ethylthio, n- or i-propylthio, or represents phenyl, or—if m represents 2—optionally also together with a second radical $R^3$ represents oxygen, propane-1,3-diyl or butane-1,4-diyl.

$R^4$ very particularly preferably represents hydroxyl, represents formyloxy, represents in each case optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally fluorine- and/or chlorine-substituted propenyloxy, butenyloxy, propynyloxy or butynyloxy, represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl, represents in each case optionally cyano-, oxo-, fluorine-, chlorine-, methyl-, ethyl-, methoxy-, ethoxy-, methylthio-, ethylthio-substituted pyrrolyl, pyrrolinyl, pyrrolidinyl, pyrazolyl, pyrazolinyl, pyrazolidinyl, imidazolyl, imidazolinyl, imidazolidinyl, triazolyl, triazolinyl, triazolidinyl, tetrazolyl, tetrazolinyl, tetrazolidinyl, oxazolyl, oxazolinyl, oxazolidinyl, isoxazolyl, isoxazolinyl, isoxazolidinyl, thiazolyl, thiazolinyl, thiazolidinyl, thiadiazolyl, indolyl, piperidinyl, piperazinyl, oxazinyl, thiazinyl, morpholinyl.

$R^5$ very particularly preferably represents hydrogen, cyano, fluorine, chlorine, represents in each case optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or represents optionally cyano-, fluorine-, chlorine- or methyl-substituted cyclopropyl.

$R^6$ very particularly preferably represents hydrogen, represents in each case optionally cyano-, fluorine-, chlorine-, methoxy- or ethoxy-substituted methyl, ethyl, n- or i-propyl, n-, i-, s- or t-butyl, represents in each case optionally fluorine- or chlorine-substituted propenyl, butenyl, propynyl or butynyl, represents in each case optionally fluorine-, chlorine- or methyl-substituted cyclopropyl, cyclobutyl, cyclopentyl or cyclohexyl, or represents in each case optionally fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or phenylmethyl.

$R^7$ very particularly preferably represents hydroxyl, represents formyloxy, represents in each case optionally alkyl-, cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, ethoxycarbonylmethoxy, methoxycarbonylmethoxy, methylsulphonyloxy, ethylsulphonyloxy, n- or i-propylsulphonyloxy, represents in each case optionally fluorine- and/or chlorine-substituted propenyloxy, butenyloxy, propynyloxy or butynyloxy, or represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenylmethoxy, phenylcarbonyloxy, phenylcarbonylmethoxy or phenylsulphonyloxy.

$R^8$ very particularly preferably represents hydrogen, represents in each case optionally cyano-, fluorine-, chlorine-, methoxy-, ethoxy-, n- or i-propoxy-, acetyl-, propionyl-, methoxycarbonyl- or ethoxycarbonyl-substituted methyl, ethyl, n- or i-propyl, represents in each case optionally cyano-, fluorine-, chlorine-, methoxy-, ethoxy-, n- or i-propoxy-substituted acetyl, propionyl, methoxycarbonyl or ethoxycarbonyl, represents in each case optionally fluorine- and/or chlorine-substituted methylthio, ethylthio, n- or i-propylthio, n-, i-, s- or t-butylthio, methylsulphinyl, ethylsulphinyl, methylsulphonyl or ethylsulphonyl, represents in each case optionally fluorine-, chlorine- and/or bromine-substituted propenyl, butenyl, propynyl or butynyl, represents in each case optionally fluorine-, chlorine- or methyl-substituted cyclopropyl, cyclopropylcarbonyl or cyclopropylmethyl, represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, s- or i-propoxy-, difluoromethoxy- or trifluoromethoxy-substituted phenyl, benzoyl, phenoxycarbonyl, benzyl, phenylmethylcarbonyl or phenylmethoxycarbonyl.

$R^9$ very particularly preferably represents hydrogen, represents in each case optionally cyano-, fluorine-, chlorine-, methoxy-, ethoxy-, n- or i-propoxy-, acetyl-, propionyl-, methoxycarbonyl- or ethoxycarbonyl-substituted methyl, ethyl, n- or i-propyl, represents in each case optionally cyano-, fluorine-, chlorine-, methoxy-, ethoxy-, n- or i-propoxy-substituted acetyl, propionyl, methoxycarbonyl or ethoxycarbonyl, represents in each case optionally fluorine- and/or chlorine-substituted methylthio, ethylthio, n- or i-propylthio, n-, i-, s- or t-butylthio, methylsulphinyl, ethylsulphinyl, methylsulphonyl or ethylsulphonyl, represents in each case optionally fluorine-, chlorine- and/or bromine-substituted propenyl, butenyl, propynyl or butynyl, represents in each case optionally fluorine-, chlorine- or methyl-substituted cyclopropyl, cyclopropylcarbonyl or cyclopropylmethyl, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, s- or i-propoxy-, difluoromethoxy- or trifluoromethoxy-substituted phenyl, benzoyl, phenoxycarbonyl, benzyl, phenylmethylcarbonyl or phenylmethoxycarbonyl or together with $R^2$ and the nitrogen to which they are attached represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted pyrrolidinyl, oxopyrrolidinyl, pyrrolyl, indolyl, pyrazolyl, oxazolyl, isoxazolyl, dihydropyranyl, piperidinyl, oxopiperidinyl, morpholinyl, thiomorpholinyl, 3-oxomorpholinyl, 3-oxothiomorpholinyl, piperazinyl, imidazolyl, imidazolidinyl, oxo-imidazolidinyl, triazol, triazolinyl, tetrazolinyl or pyridinyl.

$R^{10}$ very particularly preferably represents hydrogen, formyl, represents in each case optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-substituted methyl, ethyl, n- or i-propyl, n-, i-, s- or t-butyl, n-, i-, s- or t-pentyl, represents in each case optionally cyano-, fluorine-, chlorine-, methoxy-, ethoxy-, n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, represents dimethylaminocarbonyl, represents in each case optionally fluorine- and/or chlorine-substituted methylthio, ethylthio, n- or i-propylthio, n-, i-, s- or t-butylthio, methylsulphinyl, ethylsulphinyl, methylsulphonyl or ethylsulphonyl, represents in each case optionally fluorine-, chlorine- and/or bromine-substituted propenyl, butenyl, propynyl or butynyl, represents in each case optionally fluorine-, chlorine- or methyl-substituted cyclopropyl, cyclopropylcarbonyl or cyclopropylmethyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, benzoyl, phenoxycarbonyl, phenylaminocarbonyl, benzyl, phenylmethylcarbonyl or phenylmethoxycarbonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl, heterocyclylcarbonyl or heterocyclylalkyl from the group consisting of furyl, furylcarbonyl, furylmethyl, thienyl, thienylcarbonyl, thienylmethyl, pyrrolidinyl, pyrrolyl, indolyl, pyrrolylmethyl, pyrazolyl, pyrazolylmethyl, isoxazolyl, piperidinyl, morpholinyl, piperazinyl, pyridinyl, pyridinylmethyl.

X very particularly preferably represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl.

Y very particularly preferably represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl or dimethylaminosulphonyl and m very particularly preferably represents the number 0 or 2.

Particular emphasis is given to the compounds of the formulae (I-1) to (I-3):

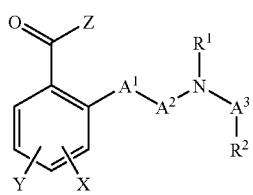

(I-1)

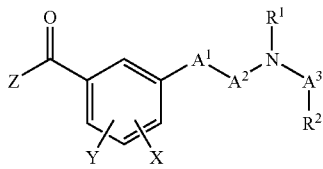

(I-2)

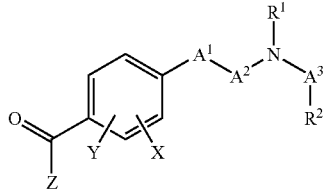

(I-3)

Here, $A^1$, $A^2$, $A^3$, $R^1$, $R^2$, X, Y and Z in each case have the meanings given above as being preferred, particularly preferred or very particularly preferred.

Furthermore, particular emphasis is given to the compounds of the general formulae (I-2A) and (I-2B):

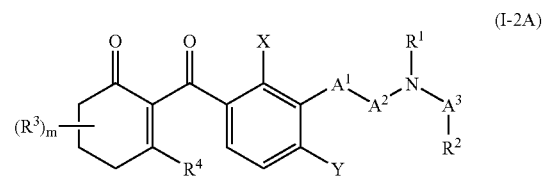

(I-2A)

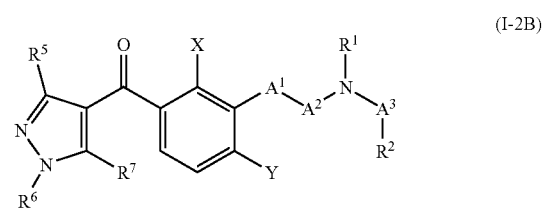

(I-2B)

Here m, $A^1$, $A^2$, $A^3$, $R^1$, $R^2$, $R^3$, $R^4$, $R^5$, $R^6$, $R^7$, X and Y in each case have the meanings given above as being preferred, particularly preferred, or very particularly preferred.

Among the compounds of the formulae (I-1) to (I-3) and (I-2A) and (I-2B), very particular emphasis is given to those in which $A^1$ represents a single bond and $A^2$ represents methylene.

Among the compounds of the formulae (I-1) to (I-3) and (I-2A) and (I-2B), very particular emphasis is furthermore given to those in which $A^1$ represents O (oxygen) and $A^2$ represents ethane-1,2-diyl (dimethylene) or propane-1,3-diyl (trimethylene).

Among the compounds of the formulae (I-1) to (I-3) and (I-2A), very particular emphasis is furthermore also given to those compounds in which m represents zero.

Among the compounds of the formulae (I-1) to (I-3) and (I-2B), very particular emphasis is furthermore also given to those in which $R^5$ represents hydrogen and $R^6$ represents methyl, ethyl, n-, i-propyl, n-, i-, s-, t-butyl.

The radical definitions can be combined with one another as desired, i.e. including combinations between the given preferred ranges. Moreover, individual radical definitions may not apply.

Preference according to the invention is given to the compounds of the formula (I) which contain a combination of the meanings given above as being preferred.

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

The general or preferred radical definitions given above apply both to the end products of the formula (I) and, correspondingly, to the starting materials or intermediates required in each case for the preparation.

The novel substituted aryl ketones of the formula (I) have strong and selective herbicidal activity.

The novel substituted aryl ketones of the formula (I) are obtained by reacting
a) carboxylic acids of the formula (II)

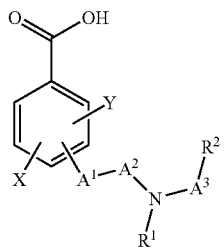 (II)

in which
$A^1, A^2, A^3, R^1, R^2$, X and Y are as defined above
—or alkali metal, alkaline earth metal or ammonium salts thereof—
with compounds of the general formula (III)

 (III)

in which
Z is as defined above, or
b) carboxylic acid derivatives of the formula (IX)

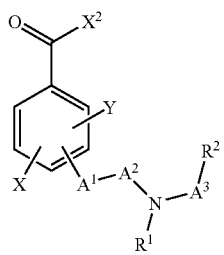 (IX)

in which
$A^1, A^2, A^{31}, R^1, R^2$, X and Y are as defined above and
$X^2$ represents CN or halogen, preferably Cl, Br, I, imidazolyl or triazolyl
with compounds of the formula (III)

 (III)

in which
Z is as defined above, or
c) compounds of the formula (XIII)

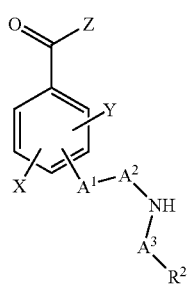 (XIII)

in which
$A^1, A^2, A^3, R^2$, X, Y and Z are as defined above with compounds of the formula (XI)

 (XI)

in which
$R^1$ is as defined above and
$X^1$ represents halogen, arylsulphonate or alkylsulphonate, preferably chlorine, bromine, iodine, mesylate or tosylate, or
d) compounds of the formula (XIV)

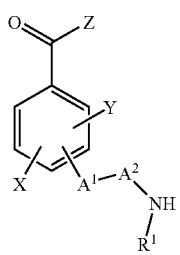 (XIV)

in which
$A^1, A^2, R^1$, X, Y and Z are as defined above
with compounds of the formula (V)

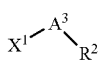 (V)

in which
$A^1$ and $R^2$ are as defined above and
$X^1$ represents halogen or tosylate, preferably chlorine, bromine or tosylate, or
e) compounds of the formula (XV)

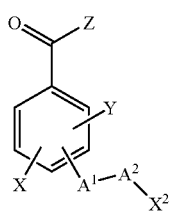 (XV)

in which
$A^1, A^2$, X, Y and Z are as defined above and
$X^2$ represents halogen or tosylate, preferably chlorine, bromine or tosylate
with compounds of the formula (VII)

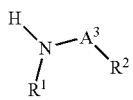 (VII)

in which
$A^3, R^1$ and $R^2$ are as defined above,
if appropriate in the presence of one or more reaction auxiliaries and if appropriate in the presence of one or more diluents.

The starting materials of the general formula (IX) have hitherto not been disclosed and, as novel substances, also form part of the subject-matter of the present application.

The novel carboxylic acid derivatives of the formula (IX) are obtained by reacting f) carboxylic acids of the formula (II)

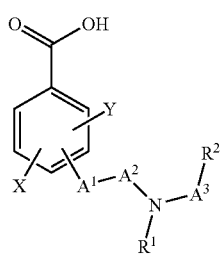

(II)

in which

A$^1$, A$^2$, A$^3$, R$^1$, R$^2$, X and Y are as defined above with suitable activating reagents, if appropriate in the presence of one or more reaction auxiliaries and if appropriate in the presence of one or more diluents.

Except for the compounds 3,4-difluoro-2-(N-methyl-N-methylsulphonyl-aminomethyl)benzoic acid, 2-(N-methyl-N-methylsulphonylaminomethyl)-4-trifluoro-, methylbenzoic acid, 4-fluoro-2-(N-methyl-N-methylsulphonylaminomethyl)benzoic acid, 2-(N-methyl-N-methylsulphonylaminomethyl)benzoic acid, 4-chloro-2-(N-methyl-N-methylsulphonylaminomethyl)benzoic acid, 4-chloro-3-fluoro-2-(N-methyl-N-methylsulphonylaminomethyl)benzoic acid and 4-chloro-3-(N-methyl-N-methylsulphonylaminomethyl)-2-methylthiobenzoic acid (cf. WO-A-95/31446) and 2-chloro-3-(methylsulphonylaminomethyl)-4-methylsulphonylbenzoic acid (cf. WO-A-00/21924), the starting materials of the general formula (II) have hitherto not been disclosed, and, as novel substances, they also form part of the subject-matter of the present application.

Preference is given to compounds of the formula (II) in which A$^1$, A$^2$, R$^1$, R$^2$, X and Y have the meanings already given above in connection with the description of the compounds of the general formula (I) according to the invention as being preferred, particularly preferred, very particularly preferred or most preferred for A$^1$, A$^2$, R$^1$, R$^2$, X and Y, and A$^3$ represents O, S, the grouping

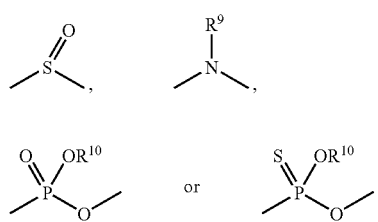

The novel carboxylic acids of the general formula (II) are obtained by reacting g) compounds of the formula (VIII)

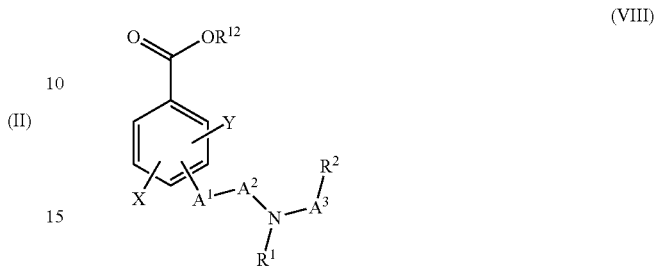

(VIII)

in which

A$^1$, A$^2$, A$^3$, R$^1$, R$^2$, X and Y are as defined above and

R$^{12}$ represents C$_1$-C$_4$-alkyl, in particular methyl, ethyl, n-, i-propyl, n-, s-, i-, t-butyl, represents allyl or benzyl under reductive or alkaline conditions in the presence of one or more reaction auxiliaries and if appropriate in the presence of one or more diluents.

The starting materials of the general formula (VIII) have hitherto not been disclosed and, as novel substances, also form part of the subject-matter of the present application.

The novel carboxylic acids of the general formula (VIE) are obtained by reacting h) compounds of the formula (VI)

(VI)

in which

A$^1$, A$^2$, X and Y are as defined above and

R$^{12}$ represents C$_1$-C$_4$-alkyl, in particular methyl, ethyl, n-, i-propyl, n-, s-, i-, t-butyl, represents allyl or benzyl with compounds of the formula (VII)

(VII)

if appropriate in the presence of one or more reaction auxiliaries and if appropriate in the presence of one or more diluents, or by reacting i) compounds of the formula (IV)

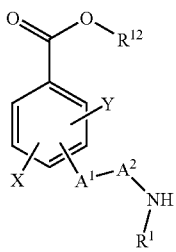

(IV)

in which
A$^1$, A$^2$, R$^1$, X and Y are as defined above and
R$^{12}$ represents C$_1$-C$_4$-alkyl, in particular methyl, ethyl, n-, i-propyl, n-, s-, i-, t-butyl, represents allyl or benzyl
with compounds of the formula (V)

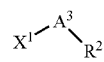

(V)

in which
A$^3$ and R$^2$ are as defined above and
X$^1$ represents halogen (preferably fluorine, chlorine, bromine or iodine, in particular chlorine, bromine or iodine),
if appropriate in the presence of one or more reaction auxiliaries and if appropriate in the presence of one or more diluents,
or by reacting i) compounds of the formula (X)

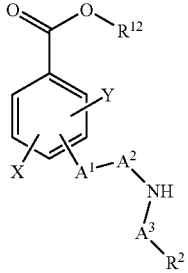

(X)

in which
A$^1$, A$^2$, A$^3$, R$^2$, X and Y are as defined above and
R$^{12}$ represents C$_1$-C$_4$-alkyl, in particular methyl, ethyl, n-, i-propyl, n-, s-, i-, t-butyl, represents allyl or benzyl
with compounds of the formula (XI)

(XI)

in which
R$^1$ is as defined above and
X$^1$ represents halogen (preferably fluorine, chlorine, bromine or iodine, in particular chlorine, bromine or iodine),
if appropriate in the presence of one or more reaction auxiliaries and if appropriate in the presence of one or more diluents,
or by reacting k) compounds of the formula (X)

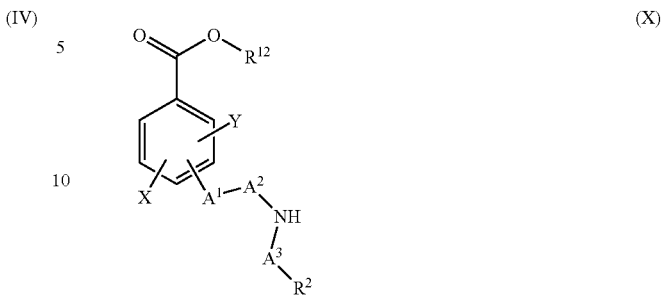

(X)

in which
A$^1$, A$^2$, A$^3$, R$^2$, X and Y are as defined above and
R$^{12}$ represents C$_1$-C$_4$-alkyl, in particular methyl, ethyl, n-, i-propyl, n-, s-, i-, t-butyl
with compounds of the formula (XII)

(XII)

in which
R$^{11'}$ and R$^{11}$ independently of one another represent hydrogen, represent optionally cyano-, halogen-, C$_1$-C$_4$-alkoxy-, C$_1$-C$_4$-alkylthio-, C$_1$-C$_4$-alkylsulphinyl- or C$_1$-C$_4$-alkylsulphonyl-substituted alkyl having 1 to 6 carbon atoms, represent in each case optionally cyano- or halogen-substituted alkenyl or alkynyl having in each case 3 to 6 carbon atoms, represent in each case optionally cyano-, halogen- or C$_1$-C$_4$-alkyl-substituted cycloalkyl or cycloalkylalkyl having in each case 3 to 6 carbon atoms in the cycloalkyl group and, if appropriate, 1 to 4 carbon atoms in the alkyl moiety, or represent in each case optionally nitro-, cyano-, halogen-, C$_1$-C$_4$-alkyl-, C$_1$-C$_4$-haloalkyl-, C$_1$-C$_4$-alkoxy-, C$_1$-C$_4$-haloalkoxy-, C$_1$-C$_4$-alkylthio-, C$_1$-C$_4$-haloalkylthio-, C$_1$-C$_4$-alkylsulphinyl-, C$_1$-C$_4$-haloalkylsulphinyl-, C$_1$-C$_4$-alkylsulphonyl- or C$_1$-C$_4$-haloalkylsulphonyl-substituted aryl or arylalkyl having in each case 6 or 10 carbon atoms in the aryl group and, if appropriate, 1 to 4 carbon atoms in the alkyl moiety,
preferably represent hydrogen, methyl, ethyl, n-Pr, i-Pr, cyclopropyl, n-butyl, i-butyl, cyclobutyl, phenyl, benzyl and tolyl,
in the presence of a reducing agent, preferably a borane or a BH$_3$ adduct,
if appropriate in the presence of one or more reaction auxiliaries and if appropriate in the presence of one or more diluents.

Following the practice of the processes of a) to e) according to the invention, the resulting compounds of the general formula (I) can, if desired, be subjected to subsequent reactions within the scope of the definition of substituents (for example substitution, oxidation or reduction reactions) for conversion into other compounds of the general formula (I) by customary methods.

If appropriate, a plurality of the process steps mentioned above can be combined by dispensing with the isolation of the reaction products and using them directly for the subsequent process step.

Below, process a) according to the invention is illustrated in more detail:

The formula (II) provides a general definition of the carboxylic acids to be used as starting materials. In the formula (II), $A^1, A^2, A^3, R^1, R^2$, X and Y preferably have those meanings which have already been mentioned above, in connection with the description of the compounds of the general formula (I) according to the invention, as being preferred, particularly preferred, very particularly preferred or most preferred for $A^1, A^2, A^3, R^1, R^2$, X and Y. The starting materials of the formula (II) can be obtained, for example, by process g).

The formula (III) provides a general definition of the compounds further to be used as starting materials. In the formula (III), Z preferably has those meanings which have already been mentioned above, in connection with the description of the compounds of the general formula (I) according to the invention, as being preferred, particularly preferred, very particularly preferred or most preferred for Z, $R^3, R^4, R^5, R^6, R^7$. The starting materials of the formula (III) are known or can be prepared by known processes.

For carrying out the process a), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

The process a) according to the invention is, if appropriate, carried out using a dehydrating agent. Suitable dehydrating agents are the customary chemicals suitable for binding water. Examples which may be mentioned are dicyclohexylcarbodiimide, carbonylbisimidazole and propanephosphonic anhydride. Dehydrating agents which may be mentioned as being particularly suitable are dicyclohexylcarbodiimide and propanephosphonic hydride (cf. WO 99/28282).

Process a) according to the invention is, if appropriate, carried out using a rearrangement reagent. Suitable rearrangement reagents are the customary chemicals suitable for rearrangement. Examples which may be mentioned are trimethylsilyl cyanide, potassium cyanide and acetone cyanohydrin.

The process a) for preparing the compounds of the general formula (I) is preferably carried out using one or more diluents. Suitable diluents are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process a), the reaction temperatures can be varied within a relatively wide range. In general, the process is carried out at temperatures between 0° C. and 150° C., preferably between 10° C. and 120° C.

In general, the process a) is carried out under atmospheric pressure. However, the process according to the invention can also be carried out under elevated or reduced pressure—in general between 0.1 bar and 10 bar.

If, for example, the starting materials used in process a) are 4-chloro-3-(ethoxyaminomethyl)benzoic acid and cyclohexane-1,3-dione, the course of the reaction in the process according to the invention can be illustrated by the formula scheme below:

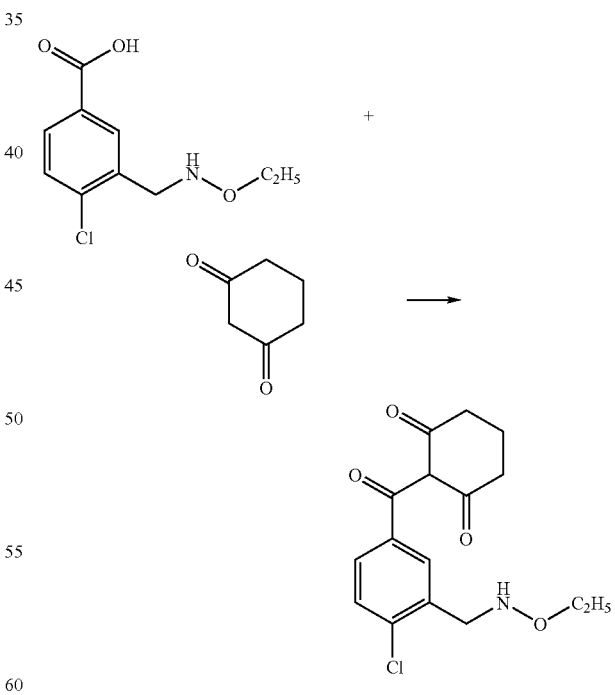

Below, process b) according to the invention is illustrated in more detail:

Formula (IX) provides a general definition of the carboxylic acid derivatives to be used as starting materials. In the formula (IX), $A^1, A^2, A^3, R^1, R^2$, X and Y preferably have those meanings which have already been mentioned above, in connection with the description of the compounds of the general formula (I) according to the invention, as being preferred, particularly preferred, very particularly preferred or most preferred for $A^1$, $A^2$, $A^3$, $R^1$, $R^2$, X and Y. The starting materials of the formula (IX) can be obtained, for example, by process f).

The formula (III) provides a general definition of the compounds further to be used as starting materials. In the formula (III), Z preferably has those meanings which have already been mentioned above, in connection with the description of the compounds of the general formula (I) according to the invention, as being preferred, particularly preferred, very particularly preferred or most preferred for Z, $R^3$, $R^4$, $R^5$, $R^6$, $R^7$. The starting materials of the formula (III) are known or can be prepared by known processes.

For carrying out process b), the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i- s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

The process b) according to the invention is, if appropriate, carried out using a rearrangement reagent. Suitable rearrangement reagents are the customary chemicals suitable for rearrangement. Examples which may be mentioned are trimethylsilyl cyanide, potassium cyanide and acetone cyanohydrin.

Process b) is preferably carried out using one or more diluents. Suitable diluents are especially the solvents mentioned in process a).

When carrying out the process b), the reaction temperatures can be varied within a relatively wide range. In general, the process is carried out at temperatures between 0° C. and 150° C., preferably between 10° C. and 120° C.

The process b) is generally carried out under atmospheric pressure. However, it is also possible to carry out the process according to the invention under elevated or reduced pressure—in general between 0.1 bar and 10 bar.

Below, the process c) according to the invention is illustrated in more detail:

The formula (XIII) provides a general definition of the secondary amines to be used as starting materials. In the formula (XIII), $A^1$, $A^2$, $A^3$, $R^2$, X, Y and Z preferably have those meanings which have already been mentioned above, in connection with the description of the compounds of the general formula (I) according to the invention, as being preferred, particularly preferred, very particularly preferred or most preferred for $A^1$, $A^2$, $A^3$, $R^2$, X, Y and Z. The starting materials of the formula (XIII) are known or can be obtained by known processes.

The formula (XI) provides a general definition of the compounds further to be used as starting materials. In the formula (XI), $R^1$ preferably has those meanings which have already been mentioned above, in connection with the description of the compounds of the general formula (I) according to the invention, as being preferred, particularly preferred, very particularly preferred or most preferred for $R^1$. The starting materials of the formula (XI) are known or can be obtained by known processes.

For carrying out process c), the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods.

Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

The process c) is preferably carried out using one or more diluents. Suitable diluents are especially water and inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out process c), the reaction temperatures can be varied within a relatively wide range. In general, the process is carried out at temperatures between 0° C. and 150° C., preferably between 10° C. and 120° C.

The process c) is generally carried out under atmospheric pressure. However, it is also possible to carry out the process according to the invention under elevated or reduced pressure—in general between 0.1 bar and 10 bar.

Below, the process d) according to the invention is illustrated in more detail:

The formula (XIV) provides a general definition of the secondary amines to be used as starting materials. In the formula (XIV), $A^1$, $A^2$, $R^1$, X, Y and Z preferably have those meanings which have already been mentioned above, in connection with the description of the compounds of the general formula (I) according to the invention, as being preferred, particularly preferred, very particularly preferred or most preferred for $A^1$, $A^2$, $R^1$, X, Y and Z. The starting materials of the formula (XIV) are known or can be prepared by known processes.

The formula (V) provides a general definition of the compounds further to be used as starting materials. In the formula (V), $R^2$ and $A^3$ preferably have those meanings which have already been mentioned above, in connection with the description of the compounds of the general formula (I) according to the invention, as being preferred, particularly preferred, very particularly preferred or most preferred for $R^2$ and $A^3$. The starting materials of the formula (V) are known or can be prepared by known processes.

For carrying out the process d), the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include the compounds mentioned in process c).

The process d) for preparing the compounds of the general formula (I) is preferably carried out using one or more diluents. Suitable diluents are, preferably, the diluents mentioned in process c).

When carrying out the process d), the reaction temperatures can be varied within a relatively wide range. In general, the process is carried out at temperatures between 0° C. and 150° C., preferably between 10° C. and 120° C.

The process d) is generally carried out under atmospheric pressure. However, it is also possible to carry out the process according to the invention under elevated or reduced pressure—in general between 0.1 bar and 10 bar.

Below, process e) according to the invention is illustrated in more detail:

The formula (XV) provides a general definition of the compounds to be used as starting materials. In the formula (XV), $A^1$, $A^2$, X, Y and Z preferably have those meanings which have already been mentioned above, in connection with the description of the compounds of the general formula (I) according to the invention, as being preferred, particularly preferred, very particularly preferred or most preferred for $A^1$, $A^2$, $R^1$, X, Y and Z. The starting materials of the formula (XV) are known or can be prepared by known processes.

The formula (VII) provides a general definition of the amines further to be used as starting materials. In the formula (VII), $R^1$, $R^2$ and $A^3$ preferably have those meanings which have already been mentioned above, in connection with the description of the compounds of the general formula (I) according to the invention, as being preferred, particularly preferred, very particularly preferred or most preferred for $R^1$, $R^2$ and $A^3$. The starting materials of the formula (VII) are known or can be prepared by known processes.

For carrying out the process e), the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods.

Suitable reaction auxiliaries are, in general, the customary inorganic or organic bases or acid acceptors. These preferably include the compounds mentioned in process c).

The process e) for preparing the compounds of the formula (I) is preferably carried out using one or more diluents. Suitable diluents are preferably the diluents mentioned in process c).

When carrying out the process e), the reaction temperatures can be varied within a relatively wide range. In general, the process is carried out at temperatures between 0° C. and 150° C., preferably between 10° C. and 120° C.

The process e) is generally carried out under atmospheric pressure. However, it is also possible to carry out the process according to the invention under elevated or reduced pressure—generally between 0.1 bar and 10 bar.

Below, the process f) according to the invention is illustrated in more detail:

The formula (II) provides a general definition of the carboxylic acids used as starting materials. In the formula (II), $A^1$, $A^2$, $A^3$, $R^1$, $R^2$, X and Y preferably have those meanings which have already been mentioned above, in connection with the description of the compounds of the general formula (I) according to the invention, as being preferred, particularly preferred, very particularly preferred or most preferred for $A^1$, $A^2$, $A^3$, $R^1$, $R^2$, X and Y. The starting materials of the formula (II) can be obtained, for example, by process g).

Suitable activating reagents are halogenating agents, in particular phosphoryl chloride or phosphoryl bromide, sulphuryl chloride, oxalyl chloride, phosgene; cyanating agents, in particular cyanohydrin or hydrocyanic acid; imidazole or imidazole derivatives, such as bisimidazolylcarbonyl, and triazole or triazole derivatives, such as, for example, bistriazolylcarbonyl.

For carrying out the process f), the starting materials are generally employed in approximately equimolar amounts. However, it is also possible to use a relatively large excess of one of the components. The reaction is generally carried out in a suitable diluent in the presence of a reaction auxiliary and the reaction mixture is generally stirred at the required temperature for a number of hours. Work-up is carried out by customary methods.

Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

The process f) for preparing the compounds of the general formula (I) is preferably carried out using one or more diluents. Suitable diluents are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process f), the reaction temperatures can be varied within a relatively wide range. In general, the process is carried out at temperatures between −30° C. and 150° C., preferably between −10° C. and 100° C.

The process f) is generally carried out under atmospheric pressure. However, it is also possible to carry out the process according to the invention under elevated or reduced pressure—in general between 0.1 bar and 10 bar.

Below, the process g) according to the invention is illustrated in more detail:

The formula (VIII) provides a general definition of the carboxylic esters to be used as starting materials. In the formula (VIII), $A^1, A^2, A^3, R^1, R^2$, X and Y preferably have those meanings which have already been mentioned above, in connection with the description of the compounds of the general formula (I) according to the invention, as being preferred, particularly preferred, very particularly preferred or most preferred for $A^1, A^2, A^3, R^1, R^2$, X and Y. The starting materials of the formula (VIII) can be obtained, for example, by process h), i), j), k).

The process g) can be carried out under alkaline, acidic or reductive conditions.

Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

Suitable reaction auxiliaries are furthermore customary hydrogenation catalysts, such as palladium and platinum on heterogeneous supports such as activated carbon or barium sulphate.

Suitable reaction auxiliaries are furthermore reducing agents such as aluminium hydrides and borohydrides, for example potassium aluminium hydride and sodium borohydride.

The process g) for preparing the compounds of the general formula (II) is preferably carried out using one or more diluents. Suitable diluents are especially water and inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process g), the reaction temperatures may be varied within a relatively wide range. In general, the process is carried out at temperatures between 0° C. and 150° C., preferably between 10° C. and 120° C.

The process g) is generally carried out under atmospheric pressure. However, it is also possible to carry out the process according to the invention under elevated or reduced pressure—in general between 0.1 bar and 100 bar, preferably between atmospheric pressure and 20 bar, particularly preferably between atmospheric pressure and 10 bar. If the process g) is carried out under elevated pressure, an elevated hydrogen partial pressure is preferred.

Below, the process h) according to the invention is illustrated in more detail:

The formula (VI) provides a general definition of the compounds to be used as starting materials. In the formula (VI), $A^1, A^2$, X and Y preferably have those meanings which have already been mentioned above, in connection with the description of the compounds of the general formula (I) according to the invention, as being preferred, particularly preferred, very particularly preferred or most preferred for $A^1, A^2$, X and Y. The starting materials of the formula (VI) are known or can be obtained by known processes (cf. WO-A-95/31446, WO-A-01/53275, DE-A-10122445, Preparation Examples).

The formula (VII) provides a general definition of the compounds further to be used as starting materials. In the formula (VII), $A^3$, $R^1$ and $R^2$ preferably have those meanings which have already been mentioned above, in connection with the description of the compounds of the general formula (I) according to the invention, as being preferred, particularly preferred, very particularly preferred or most preferred for $A^3$, $R^1$ and $R^2$. The starting materials of the formula (III) are known or can be prepared by known processes.

For carrying out the process h), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethyl-piperidine, N-methylmorpholine, N-ethylmorpholine, 1,4-diazabicyclo[2.2.2]octane (DABCO), 1,5-diazabicyclo[4.3.0]non-5-ene (DBN) or 1,8-diazabicyclo[5.4.0]-undec-7-ene (DBU).

The process h) for preparing the compounds of the general formula (VIII) is preferably carried out using one or more diluents. Suitable diluents are especially water and inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process h), the reaction temperatures can be varied within a relatively wide range. In general, the process is carried out at temperatures between 0° C. and 150° C., preferably between 10° C. and 120° C.

The process h) is generally carried out under atmospheric pressure. However, it is also possible to carry out the process according to the invention under elevated or reduced pressure—in general between 0.1 bar and 10 bar.

Below, the process i) according to the invention is illustrated in more detail:

The formula (IV) provides a general definition of the compounds to be used as starting materials. In the formula (IV), $A^1$, $A^2$, $R^1$, X and Y preferably have those meanings which have already been mentioned above, in connection with the description of the compounds of the general formula (I) according to the invention, as being preferred, particularly preferred, very particularly preferred or most preferred for $A^1$, $A^2$, $R^1$, X and Y. The starting materials of the formula (IV) are known or can be obtained by known processes (cf. WO-A-95/31446, WO-A-01/53275, DE-A-10122445, Preparation Examples).

The formula (V) provides a general definition of the compounds further to be used as starting materials. In the formula (V), $A^3$ and $R^2$ preferably have those meanings which have already been mentioned above, in connection with the description of the compounds of the general formula (I) according to the invention, as being preferred, particularly preferred, very particularly preferred or most preferred for $A^3$ and $R^2$. The starting materials of the formula (III) are known or can be prepared by known processes.

For carrying out the process i), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include the reaction auxiliaries mentioned in process h).

The process i) for preparing the compounds of the general formula (VIII) is preferably carried out using one or more diluents. Suitable diluents are especially the diluents mentioned in process h).

When carrying out the process i), the reaction temperatures can be varied within a relatively wide range. In general, the process is carried out at temperatures between 0° C. and 150° C., preferably between 10° C. and 120° C.

The process i) is generally carried out under atmospheric pressure. However, it is also possible to carry out the process according to the invention under elevated or reduced pressure—in general between 0.1 bar and 10 bar.

Below, the process j) according to the invention is illustrated in more detail:

The formula (X) provides a general definition of the compounds to be used as starting materials. In the formula (X), $A^1$, $A^2$, $A^3$, $R^2$, X and Y preferably have those meanings which have already been mentioned above, in connection with the description of the compounds of the general formula (I) according to the invention, as being preferred, particularly preferred, very particularly preferred or most preferred for $A^1$, $A^2$, $A^3$, $R^2$, X and Y. The starting materials of the formula (X) are known or can be obtained by known processes (cf. WO-A-95/31446, WO-A-01/53275, DE-A-10122445, Preparation Examples).

The formula (XI) provides a general definition of the compounds further to be used as starting materials. In the formula (XI), $R^1$ preferably has those meanings which have already been mentioned above, in connection with the description of the compounds of the general formula (I) according to the invention, as being preferred, particularly preferred, very particularly preferred or most preferred for $R^1$. The starting materials of the formula (XI) are known or can be prepared by known processes.

For carrying out the process j), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include the reaction auxiliaries mentioned in process h).

The process j) for preparing the compounds of the formula (VIII) is preferably carried out using one or more diluents. Suitable diluents are especially the diluents mentioned in process h).

When carrying out the process j), the reaction temperatures can be varied within a relatively wide range. In general, the process is carried out at temperatures between 0° C. and 150° C., preferably between 10° C. and 120° C.

The process j) is generally carried out under atmospheric pressure. However, it is also possible to carry out the process according to the invention under elevated or reduced pressure—in general between 0.1 bar and 10 bar.

Below, the process k) according to the invention is illustrated in more detail:

The formula (X) provides a general definition of the compounds to be used as starting materials. In the formula (X), $A^1$, $A^2$, $A^3$, $R^2$, X and Y preferably have those meanings which have already been mentioned above, in connection with the description of the compounds of the formula (I) according to the invention, as being preferred, particularly preferred, very particularly preferred or most preferred for $A^1$, $A^2$, $A^3$, $R^2$, X and Y. The starting materials of the formula (X) are known or can be obtained by known processes (cf. WO-A-95/31446, WO-A-01/53275, DE-A-10122445, Preparation Examples).

The formula (XII) provides a general definition of the compounds further to be used as starting materials. In the formula (XII), $R^{11'}$ and $R^{11}$ have those meanings which have already been mentioned above, in connection with the description of the process k), as being preferred, particularly preferred, very particularly preferred or most preferred for $R^{11'}$ and $R^{11}$. The starting materials of the formula (XII) are known or can be prepared by known processes.

For carrying out the process k), the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out by customary methods (cf. the Preparation Examples).

Suitable reaction auxiliaries are, in general, the customary inorganic or organic bases or acid acceptors. These preferably include the reaction auxiliaries mentioned in process h).

The process k) is preferably carried out using one or more diluents. Suitable diluents are especially the diluents mentioned in process h).

When carrying out the process k), the reaction temperatures can be varied within a relatively wide range. In general, the process is carried out at temperatures between –30° C. and 150° C., preferably between –10° C. and 80° C.

The process k) is generally carried out under atmospheric pressure. However, it is also possible to carry out the process according to the invention under elevated or reduced pressure—in general between 0.1 bar and 10 bar.

The process k) is described, for example, in Synlett 1997, 859-861.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

As already mentioned above, it is possible to treat all plants and their parts according to the invention. In a preferred embodiment, wild plant species and cultivars, or those obtained by conventional biological breeding, such as crossing or protoplast fusion, and parts thereof, are treated. In a further preferred embodiment, transgenic plants and cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the cultivars which are in each case commercially available or in use are treated according to the invention. Cultivars are to be understood as meaning plants having certain properties ("traits") and which have been obtained by conventional breeding, by mutagenesis or by recombinant DNA techniques. They can be varieties, bio- or genotypes.

Depending on the plant species or cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention also in combination with other agrochemically active compounds, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or cultivars (i.e. those obtained by genetic engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice) maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to cultivars having these genetic traits or genetic traits still to be developed, which plants will be developed and/or marketed in the future.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example
acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachilor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dyrnron, epropodan, EPTC, esprocarb, ethalfluralin, ethametsulfuron (-methyl), ethofumesate, ethoxyfen, ethoxysulfiron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazbne (-sodium), flufenacet, flufenpyr, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfeuron (-methyl, -sodium), ioxynil, isopropalin, isoproturon, isouron, isoxaben, isoxachlortole, isoxaflutole, isoxapyrifop, ketospiradox, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfueron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxysulam, pentoxazone, pethoxamid, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The plants listed can be treated according to the invention in a particularly advantageous manner with the compounds of the general formula I or the active compound mixtures according to the invention where, in addition to the effective control of the weeds, the abovementioned synergistic effects with the transgenic plants or plant cultivars occur. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

Process a

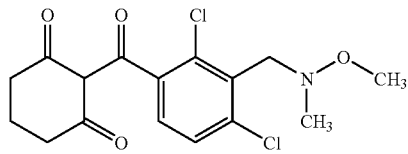

A mixture of 535 mg (4.77 mmol) of 1,3-cyclohexanedione, 1.20 g (4.54 mmol) of 2,4-dichloro-3-(N-methoxy-N-methylaminomethyl)benzoic acid, 1.25 g (5.45 mmol) of dicyclohexylcarbodiimide and 50 ml of acetonitrile is stirred at room temperature (about 20° C.) for 15 hours. 0.92 g (9.09 mmol) of triethylamine and 0.18 g (1.82 mmol) of trimethylsilyl cyanide are then added to this mixture, and the reaction mixture is stirred at room temperature for 15 hours. The mixture is then concentrated under reduced pressure and the residue is stirred with saturated aqueous sodium carbonate solution, diethyl ether is added and the mixture is filtered. The aqueous phase of the filtrate is separated off, acidified with 2N hydrochloric acid and extracted with methylene chloride. The organic extract is washed with water, dried with sodium sulphate and filtered. The filtrate is concentrated under reduced pressure and the residue is purified by preparative HPLC (high performance liquid chromatography).

This gives 0.7 g (43% of theory) of 2-[2,4-dichloro-3-(N-methoxy-N-methylaminomethyl)benzoyl]-1,3-cyclohexanedione. log P=3.04.

Example 2

Process d

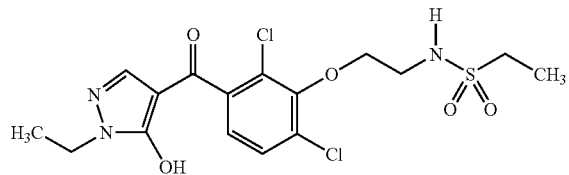

A mixture of 500 mg (1 mmol) of 4-[2,4-dichloro-(3-aminoethoxy)benzoyl]-1-ethyl-5-hydroxypyrazole and 400 mg (3 mmol) of potassium carbonate in 20 ml of dimethyl sulphoxide is stirred at room temperature (about 20° C.) for 1 h. At room temperature, 300 mg (2 mmol) of ethylsulphonyl chloride are then added, and the mixture is stirred at this temperature for 18 h. 40 ml of water are then added. The reaction mixture is extracted three times with 30 ml of dichloromethane. The organic phase is washed twice with 20 ml of water, dried with sodium sulphate and filtered. The filtrate is concentrated under reduced pressure and purified by chromatography (mobile phase: cyclohexane:ethyl acetate=3:7).

This gives 300 mg of 4-[2,4-dichloro-3-(N-ethylsulphonylaminoethoxy)benzoyl]-1-ethyl-5-hydroxypyrazole.

Analogously to Examples 1 and 2, and in accordance with the general description of the preparation process according to the invention, it is also possible, for example, to prepare the compounds of the general formula (I)—or the formulae (I-1), (I-2), (I-3), (I-2A) and (I-2B)—listed in Table 1 below.

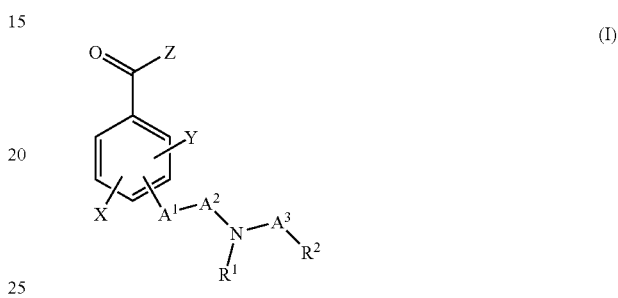

(I)

The abbreviations used in Table 1 are as defined below:

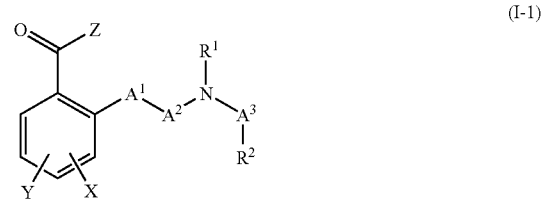

(I-1)

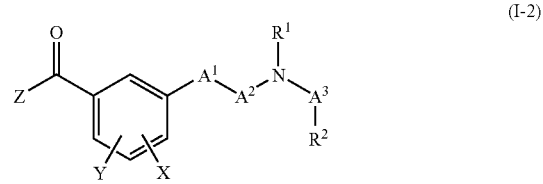

(I-2)

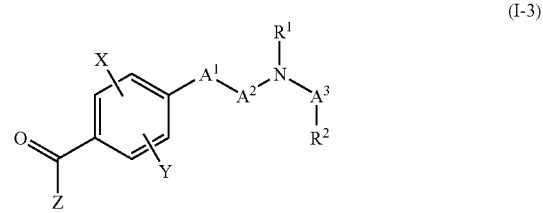

(I-3)

(Z1)

(Z2)

-continued

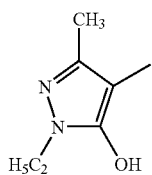
(Z3)

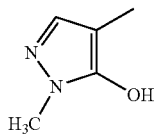
(Z4)

TABLE 1

Examples of compounds of the formula (I)

| Ex. No. | $A^1$ | $A^2$ | $A^3$ | $R^1$ | $R^2$ | (position) X | (position) Y | data | Formula Physical |
|---|---|---|---|---|---|---|---|---|---|
| 1 | — | $CH_2$ | O | $CH_3$ | $CH_3$ | (2)Cl | (2)Cl | Z1 | (I-2) logP = 3.04 |
| 2 | O | $(CH_2)_2$ | $SO_2$ | H | $C_2H_5$ | (2)Cl | (4)Cl | Z2 | (I-2) logP = 1.86[a] |
| 3 | O | $(CH_2)_2$ | $SO_2$ | H | -C6H4-CH3 | (2)Cl | (4)Cl | Z2 | (I-2) logP = 2.74[a] |
| 4 | O | $(CH_2)_2$ | $SO_2$ | H | $C_2H_5$ | (2)Cl | (4)Cl | Z1 | (I-2) logP = 2.36[a] |
| 5 | O | $(CH_2)_2$ | $SO_2$ | H | $CH_3$ | (2)Cl | (4)Cl | Z1 | (I-2) logP = 2.16[a] |
| 6 | O | $(CH_2)_2$ | $SO_2$ | H | $CH_3$ | (2)Cl | (4)Cl | Z2 | (I-2) logP = 1.65[a] |
| 7 | O | $(CH_2)_2$ | $SO_2$ | H | $CH_2Cl$ | (2)Cl | (4)Cl | Z1 | (I-2) logP = 2.57[a] |
| 8 | O | $(CH_2)_2$ | $SO_2$ | H | $CH_2Cl$ | (2)Cl | (4)Cl | Z2 | (I-2) logP = 2.05[a] |
| 9 | O | $(CH_2)_2$ | $SO_2$ | H | $CF_3$ | (2)Cl | (4)Cl | Z1 | (I-2) logP = 3.25[a] |
| 10 | O | $(CH_2)_2$ | $SO_2$ | H | $CF_3$ | (2)Cl | (4)Cl | Z2 | (I-2) logP = 2.72[a] |
| 11 | — | $CH_2$ | O | $CH_3$ | $CH_3$ | (2)Cl | (4)$SO_2CH_3$ | Z2 | (I-2) logP = 1.78[a] |
| 12 | — | $CH_2$ | O | $CH_3$ | $CH_3$ | (2)Cl | (4)$SO_2CH_3$ | Z3 | (I-2) logP = 1.45[a] |
| 13 | O | $(CH_2)_2$ | $SO_2$ | H | $CH_3$ | (2)Cl | (4)$SO_2CH_3$ | Z2 | (I-2) logP = 1.23[a] |
| 14 | O | $(CH_2)_2$ | $SO_2$ | H | $CH_3$ | (2)Cl | (4)$SO_2CH_3$ | Z1 | (I-2) logP = 1.76[a] |
| 15 | O | $(CH_2)_2$ | $SO_2$ | H | $C_2H_5$ | (2)Cl | (4)$SO_2CH_3$ | Z2 | (I-2) |
| 16 | O | $(CH_2)_2$ | $SO_2$ | H | $C_2H_5$ | (2)Cl | (4)$SO_2CH_3$ | Z1 | (I-2) |
| 17 | O | $(CH_2)_2$ | $SO_2$ | H | $CH_3$ | (2)Br | (4)Br | Z2 | (I-2) logP = 1.71[a] |
| 18 | O | $(CH_2)_2$ | $SO_2$ | H | $CH_3$ | (2)Br | (4)Br | Z1 | (I-2) logP = 2.23[a] |
| 19 | O | $(CH_2)_2$ | $SO_2$ | H | $C_2H_5$ | (2)Br | (4)Br | Z2 | (I-2) |
| 20 | O | $(CH_2)_2$ | $SO_2$ | H | $C_2H_5$ | (2)Br | (4)Br | Z1 | (I-2) logP = 2.45[a] |
| 21 | O | $(CH_2)_2$ | $SO_2$ | H | -C6H4-CH3 | (2)Cl | (4)Cl | Z1 | (I-2) |
| 22 | O | $(CH_2)_2$ | $SO_2$ | $SO_2CH_3$ | $CH_3$ | (2)Cl | (4)Cl | Z2 | (I-2) |
| 23 | O | $(CH_2)_2$ | $SO_2$ | $SO_2CH_3$ | $CH_3$ | (2)Cl | (4)Cl | Z1 | (I-2) |
| 24 | O | $(CH_2)_2$ | $SO_2$ | H | $C_3H_7$-i | (2)Cl | (4)Cl | Z2 | (I-2) logP = 2.07[a] |
| 25 | O | $(CH_2)_2$ | $SO_2$ | H | $C_3H_7$-i | (2)Cl | (4)Cl | Z1 | (I-2) logP = 2.50[a] |
| 26 | O | $(CH_2)_2$ | $SO_2$ | H | $CCl_3$ | (2)Cl | (4)Cl | Z2 | (I-2) |
| 27 | O | $(CH_2)_2$ | $SO_2$ | H | $CCl_3$ | (2)Cl | (4)Cl | Z1 | (I-2) |
| 28 | O | $(CH_2)_2$ | $SO_2$ | H | $CH_2CF_3$ | (2)Cl | (4)Cl | Z2 | (I-2) |
| 29 | O | $(CH_2)_2$ | $SO_2$ | H | $CH_2CF_3$ | (2)Cl | (4)Cl | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 30 | O | (CH$_2$)$_2$ | SO$_2$ | CH$_2$SO$_2$CH$_2$Cl | CH$_2$Cl | (2)Cl | (4)Cl | Z2 | (I-2) |
| 31 | O | (CH$_2$)$_2$ | SO$_2$ | CH$_2$SO$_2$CH$_2$Cl | CH$_2$Cl | (2)Cl | (4)Cl | Z1 | (I-2) |
| 32 | O | (CH$_2$)$_2$ | SO$_2$ | H | CH$_2$CH$_2$Cl | (2)Cl | (4)Cl | Z2 | (I-2) |
| 33 | O | (CH$_2$)$_2$ | SO$_2$ | H | CH$_2$CH$_2$Cl | (2)Cl | (4)Cl | Z1 | (I-2) |
| 34 | O | (CH$_2$)$_2$ | SO$_2$ | H | 5-methylthiophen-2-yl | (2)Cl | (4)Cl | Z2 | (I-2) logP = 2.41[a] |
| 35 | O | (CH$_2$)$_2$ | SO$_2$ | H | 5-methylthiophen-2-yl | (2)Cl | (4)Cl | Z1 | (I-2) logP = 2.92[a] |
| 36 | O | (CH$_2$)$_2$ | S | H | C$_4$H$_9$-t | (2)Cl | (4)Cl | Z2 | (I-2) |
| 37 | O | (CH$_2$)$_2$ | S | H | C$_4$H$_9$-t | (2)Cl | (4)Cl | Z1 | (I-2) |
| 38 | O | (CH$_2$)$_2$ | O | H | CH$_3$ | (2)Cl | (4)Cl | Z2 | (I-2) |
| 39 | O | (CH$_2$)$_2$ | O | H | CH$_3$ | (2)Cl | (4)Cl | Z1 | (I-2) |
| 40 | O | (CH$_2$)$_2$ | P(=O)(OC$_2$H$_5$)(CH$_3$) | H | C$_2$H$_5$ | (2)Cl | (4)Cl | Z2 | (I-2) |
| 41 | O | (CH$_2$)$_2$ | P(=O)(OC$_2$H$_5$)(CH$_3$) | H | C$_2$H$_5$ | (2)Cl | (4)Cl | Z1 | (I-2) |
| 42 | O | (CH$_2$)$_2$ | O | SO$_2$CH$_3$ | CH$_3$ | (2)Cl | (4)Cl | Z2 | (I-2) |
| 43 | O | (CH$_2$)$_2$ | O | SO$_2$CH$_3$ | CH$_3$ | (2)Cl | (4)Cl | Z1 | (I-2) |
| 44 | O | (CH$_2$)$_2$ | SO | H | CH$_3$ | (2)Cl | (4)Cl | Z2 | (I-2) |
| 45 | O | (CH$_2$)$_2$ | SO | H | CH$_3$ | (2)Cl | (4)Cl | Z1 | (I-2) |
| 46 | O | (CH$_2$)$_2$ | P(=O)(OC$_2$H$_5$)(CH$_3$) | H | C$_2$H$_5$ | (2)Cl | (4)SO$_2$CH$_3$ | Z2 | (I-2) |
| 47 | O | (CH$_2$)$_2$ | P(=O)(OC$_2$H$_5$)(CH$_3$) | H | C$_2$H$_5$ | (2)Cl | (4)SO$_2$CH$_3$ | Z1 | (I-2) |
| 48 | O | (CH$_2$)$_2$ | SO | H | CH$_3$ | (2)Cl | (4)SO$_2$CH$_3$ | Z2 | (I-2) |
| 49 | O | (CH$_2$)$_2$ | SO | H | CH$_3$ | (2)Cl | (4)SO$_2$CH$_3$ | Z1 | (I-2) |
| 50 | O | (CH$_2$)$_2$ | O | SO$_2$CH$_3$ | CH$_3$ | (2)Cl | (4)SO$_2$CH$_3$ | Z2 | (I-2) |
| 51 | O | (CH$_2$)$_2$ | O | SO$_2$CH$_3$ | CH$_3$ | (2)Cl | (4)SO$_2$CH$_3$ | Z1 | (I-2) |
| 52 | O | (CH$_2$)$_2$ | SO$_2$ | SO$_2$CH$_3$ | CH$_3$ | (2)Cl | (4)SO$_2$CH$_3$ | Z2 | (I-2) |
| 53 | O | (CH$_2$)$_2$ | SO$_2$ | SO$_2$CH$_3$ | CH$_3$ | (2)Cl | (4)SO$_2$CH$_3$ | Z1 | (I-2) |
| 54 | O | (CH$_2$)$_2$ | SO$_2$ | H | C$_3$H$_7$-i | (2)Cl | (4)SO$_2$CH$_3$ | Z2 | (I-2) |
| 55 | O | (CH$_2$)$_2$ | SO$_2$ | H | C$_3$H$_7$-i | (2)Cl | (4)SO$_2$CH$_3$ | Z1 | (I-2) |
| 56 | O | (CH$_2$)$_2$ | SO$_2$ | H | CF$_3$ | (2)Cl | (4)SO$_2$CH$_3$ | Z2 | (I-2) |
| 57 | O | (CH$_2$)$_2$ | SO$_2$ | H | CF$_3$ | (2)Cl | (4)SO$_2$CH$_3$ | Z1 | (I-2) |
| 58 | O | (CH$_2$)$_2$ | SO$_2$ | H | CCl$_3$ | (2)Cl | (4)SO$_2$CH$_3$ | Z2 | (I-2) |
| 59 | O | (CH$_2$)$_2$ | SO$_2$ | H | CCl$_3$ | (2)Cl | (4)SO$_2$CH$_3$ | Z1 | (I-2) |
| 60 | O | (CH$_2$)$_2$ | SO$_2$ | H | CH$_2$CF$_3$ | (2)Cl | (4)SO$_2$CH$_3$ | Z2 | (I-2) |
| 61 | O | (CH$_2$)$_2$ | SO$_2$ | H | CH$_2$CF$_3$ | (2)Cl | (4)SO$_2$CH$_3$ | Z1 | (I-2) |
| 62 | O | (CH$_2$)$_2$ | SO$_2$ | H | CH$_2$Cl | (2)Cl | (4)SO$_2$CH$_3$ | Z2 | (I-2) |
| 63 | O | (CH$_2$)$_2$ | SO$_2$ | H | CH$_2$Cl | (2)Cl | (4)SO$_2$CH$_3$ | Z1 | (I-2) |
| 64 | O | (CH$_2$)$_2$ | SO$_2$ | H | CH$_2$CH$_2$Cl | (2)Cl | (4)SO$_2$CH$_3$ | Z2 | (I-2) |
| 65 | O | (CH$_2$)$_2$ | SO$_2$ | H | CH$_2$CH$_2$Cl | (2)Cl | (4)SO$_2$CH$_3$ | Z1 | (I-2) |

TABLE 1-continued

Examples of compounds of the formula (I)

| Ex. No. | A¹ | A² | A³ | R¹ | R² | (position) X | (position) Y | Physical data | Formula |
|---|---|---|---|---|---|---|---|---|---|
| 66 | O | (CH$_2$)$_2$ | SO$_2$ | H | 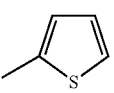 | (2)Cl | (4)SO$_2$CH$_3$ | Z2 | (I-2) |
| 67 | O | (CH$_2$)$_2$ | SO$_2$ | H | 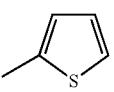 | (2)Cl | (4)SO$_2$CH$_3$ | Z1 | (I-2) |
| 68 | O | (CH$_2$)$_2$ | SO$_2$ | H | C$_4$H$_9$-t | (2)Cl | (4)SO$_2$CH$_3$ | Z2 | (I-2) |
| 69 | O | (CH$_2$)$_2$ | SO$_2$ | H | C$_4$H$_9$-t | (2)Cl | (4)SO$_2$CH$_3$ | Z1 | (I-2) |
| 70 | O | (CH$_2$)$_2$ | O | H | CH$_3$ | (2)Cl | (4)SO$_2$CH$_3$ | Z2 | (I-2) |
| 71 | O | (CH$_2$)$_2$ | O | H | CH$_3$ | (2)Cl | (4)SO$_2$CH$_3$ | Z1 | (I-2) |
| 72 | O | (CH$_2$)$_2$ | O | CH$_3$ | CH$_3$ | (2)Cl | (4)SO$_2$CH$_3$ | Z2 | (I-2) |
| 73 | O | (CH$_2$)$_2$ | O | CH$_3$ | CH$_3$ | (2)Cl | (4)SO$_2$CH$_3$ | Z1 | (I-2) |
| 74 | O | (CH$_2$)$_2$ | O | CH$_3$ | CH$_3$ | (2)Cl | (4)Cl | Z2 | (I-2) |
| 75 | O | (CH$_2$)$_2$ | O | CH$_3$ | CH$_3$ | (2)Cl | (4)Cl | Z1 | (I-2) |
| 76 | O | (CH$_2$)$_2$ | NH | H | 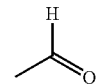 | (2)Cl | (4)Cl | Z2 | (I-2) |
| 77 | O | (CH$_2$)$_2$ | NH | H | 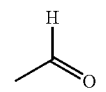 | (2)Cl | (4)Cl | Z1 | (I-2) |
| 78 | O | (CH$_2$)$_2$ | NH | H | 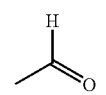 | (2)Cl | (4)SO$_2$CH$_3$ | Z2 | (I-2) |
| 79 | O | (CH$_2$)$_2$ | NH | H | 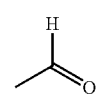 | (2)Cl | (4)SO$_2$CH$_3$ | Z1 | (I-2) |
| 80 | O | (CH$_2$)$_2$ | NH | H | C$_4$H$_9$-t | (2)Cl | (4)Cl | Z2 | (I-2) |
| 81 | O | (CH$_2$)$_2$ | NH | H | C$_4$H$_9$-t | (2)Cl | (4)Cl | Z1 | (I-2) |
| 82 | O | (CH$_2$)$_2$ | NH | H | C$_4$H$_9$-t | (2)Cl | (4)SO$_2$CH$_3$ | Z2 | (I-2) |
| 83 | O | (CH$_2$)$_2$ | NH | H | C$_4$H$_9$-t | (2)Cl | (4)SO$_2$CH$_3$ | Z1 | (I-2) |
| 84 | O | (CH$_2$)$_2$ | NH | H | SO$_2$CH$_3$ | (2)Cl | (4)Cl | Z2 | (I-2) |
| 85 | O | (CH$_2$)$_2$ | NH | H | SO$_2$CH$_3$ | (2)Cl | (4)Cl | Z1 | (I-2) |
| 86 | O | (CH$_2$)$_2$ | NH | H | SO$_2$CH$_3$ | (2)Cl | (4)SO$_2$CH$_3$ | Z2 | (I-2) |
| 87 | O | (CH$_2$)$_2$ | NH | H | SO$_2$CH$_3$ | (2)Cl | (4)SO$_2$CH$_3$ | Z1 | (I-2) |
| 88 | O | (CH$_2$)$_2$ | NH | H | 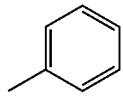 | (2)Cl | (4)Cl | Z2 | (I-2) |
| 89 | O | (CH$_2$)$_2$ | NH | H | 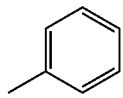 | (2)Cl | (4)Cl | Z1 | (I-2) |
| 90 | O | (CH$_2$)$_2$ | NH | H | 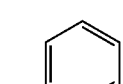 | (2)Cl | (4)SO$_2$CH$_3$ | Z2 | (I-2) |
| 91 | O | (CH$_2$)$_2$ | NH | H | 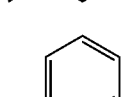 | (2)Cl | (4)SO$_2$CH$_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 92 | O | (CH$_2$)$_2$ | NH | H | COCH$_3$ | (2)Cl | (4)Cl | Z2 | (I-2) |
| 93 | O | (CH$_2$)$_2$ | NH | H | COCH$_3$ | (2)Cl | (4)Cl | Z1 | (I-2) |
| 94 | O | (CH$_2$)$_2$ | NH | H | COCH$_3$ | (2)Cl | (4)SO$_2$CH$_3$ | Z2 | (I-2) |
| 95 | O | (CH$_2$)$_2$ | NH | H | COCH$_3$ | (2)Cl | (4)SO$_2$CH$_3$ | Z1 | (I-2) |
| 96 | O | (CH$_2$)$_2$ | NH | H | COOCH$_3$ | (2)Cl | (4)Cl | Z2 | (I-2) |
| 97 | O | (CH$_2$)$_2$ | NH | H | COOCH$_3$ | (2)Cl | (4)Cl | Z1 | (I-2) |
| 98 | O | (CH$_2$)$_2$ | NH | H | COOCH$_3$ | (2)Cl | (4)SO$_2$CH$_3$ | Z2 | (I-2) |
| 99 | O | (CH$_2$)$_2$ | NH | H | COOCH$_3$ | (2)Cl | (4)SO$_2$CH$_3$ | Z1 | (I-2) |
| 100 | O | (CH$_2$)$_2$ | NH | H | CONH-C$_6$H$_5$ | (2)Cl | (4)Cl | Z2 | (I-2) |
| 101 | O | (CH$_2$)$_2$ | NH | H | CONH-C$_6$H$_5$ | (2)Cl | (4)Cl | Z1 | (I-2) |
| 102 | O | (CH$_2$)$_2$ | NH | H | CONH-C$_6$H$_5$ | (2)Cl | (4)SO$_2$CH$_3$ | Z2 | (I-2) |

TABLE 1-continued

Examples of compounds of the formula (I)

| Ex. No. | A¹ | A² | A³ | R¹ | R² | (position) X | (position) Y | Physical data | Formula |
|---|---|---|---|---|---|---|---|---|---|
| 103 | O | (CH$_2$)$_2$ | NH | H | acetyl-NH-C$_6$H$_5$ | (2)Cl | (4)SO$_2$CH$_3$ | Z1 | (I-2) |
| 104 | O | (CH$_2$)$_2$ | NH | H | 2-acetylfuran | (2)Cl | (4)Cl | Z2 | (I-2) |
| 105 | O | (CH$_2$)$_2$ | NH | H | 2-acetylfuran | (2)Cl | (4)Cl | Z1 | (I-2) |
| 106 | O | (CH$_2$)$_2$ | NH | H | 2-acetylfuran | (2)Cl | (4)SO$_2$CH$_3$ | Z2 | (I-2) |
| 107 | O | (CH$_2$)$_2$ | NH | H | 2-acetylfuran | (2)Cl | (4)SO$_2$CH$_3$ | Z1 | (I-2) |
| 108 | O | (CH$_2$)$_2$ | NH | H | 4-acetylpyridine | (2)Cl | (4)Cl | Z2 | (I-2) |
| 109 | O | (CH$_2$)$_2$ | NH | H | 4-acetylpyridine | (2)Cl | (4)Cl | Z1 | (I-2) |
| 110 | O | (CH$_2$)$_2$ | NH | H | 4-acetylpyridine | (2)Cl | (4)SO$_2$CH$_3$ | Z2 | (I-2) |
| 111 | O | (CH$_2$)$_2$ | NH | H | 4-acetylpyridine | (2)Cl | (4)SO$_2$CH$_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 112 | O | $(CH_2)_2$ | NH | H | C(O)C₆H₅ (acetophenone) | (2)Cl | (4)Cl | Z2 | (I-2) |
| 113 | O | $(CH_2)_2$ | NH | H | C(O)C₆H₅ (acetophenone) | (2)Cl | (4)Cl | Z1 | (I-2) |
| 114 | O | $(CH_2)_2$ | NH | H | C(O)C₆H₅ (acetophenone) | (2)Cl | (4)SO₂CH₃ | Z2 | (I-2) |
| 115 | O | $(CH_2)_2$ | NH | H | C(O)C₆H₅ (acetophenone) | (2)Cl | (4)SO₂CH₃ | Z1 | (I-2) |
| 116 | O | $(CH_2)_2$ | O | H | $C_2H_5$ | (2)Cl | (4)Cl | Z2 | (I-2) |
| 117 | O | $(CH_2)_2$ | O | H | $C_2H_5$ | (2)Cl | (4)Cl | Z1 | (I-2) |
| 118 | O | $(CH_2)_2$ | O | H | $C_2H_5$ | (2)Cl | (4)SO₂CH₃ | Z2 | (I-2) |
| 119 | O | $(CH_2)_2$ | O | H | $C_2H_5$ | (2)Cl | (4)SO₂CH₃ | Z1 | (I-2) |
| 120 | O | $(CH_2)_2$ | O | H | $C_3H_7$-i | (2)Cl | (4)Cl | Z2 | (I-2) |
| 121 | O | $(CH_2)_2$ | O | H | $C_3H_7$-i | (2)Cl | (4)Cl | Z1 | (I-2) |
| 122 | O | $(CH_2)_2$ | O | H | $C_3H_7$-i | (2)Cl | (4)SO₂CH₃ | Z2 | (I-2) |
| 123 | O | $(CH_2)_2$ | O | H | $C_3H_7$-i | (2)Cl | (4)SO₂CH₃ | Z1 | (I-2) |
| 124 | O | $(CH_2)_2$ | O | H | $CH_2CH=CH_2$ | (2)Cl | (4)Cl | Z2 | (I-2) |
| 125 | O | $(CH_2)_2$ | O | H | $CH_2CH=CH_2$ | (2)Cl | (4)Cl | Z1 | (I-2) |
| 126 | O | $(CH_2)_2$ | O | H | $CH_2CH=CH_2$ | (2)Cl | (4)SO₂CH₃ | Z2 | (I-2) |
| 127 | O | $(CH_2)_2$ | O | H | $CH_2CH=CH_2$ | (2)Cl | (4)SO₂CH₃ | Z1 | (I-2) |
| 128 | — | $CH_2$ | O | $CH_3$ | $CH_3$ | (2)Cl | (4)Cl | Z2 | (I-2) |
| 129 | — | $CH_2$ | O | H | $CH_3$ | (2)Cl | (4)Cl | Z1 | (I-2) logP = 2.33[a] |
| 130 | — | $CH_2$ | O | H | $CH_3$ | (2)Cl | (4)Cl | Z2 | (I-2) logP = 1.68[a] |
| 131 | — | $CH_2$ | O | H | $CH_3$ | (2)Cl | (4)SO₂CH₃ | Z1 | (I-2) |
| 132 | — | $CH_2$ | O | H | $CH_3$ | (2)Cl | (4)SO₂CH₃ | Z2 | (I-2) |
| 133 | — | $CH_2$ | O | H | $C_2H_5$ | (2)Cl | (4)Cl | Z1 | (I-2) logP = 2.75[a] |
| 134 | — | $CH_2$ | O | H | $C_2H_5$ | (2)Cl | (4)Cl | Z2 | (I-2) logP = 2.07[a] |
| 135 | — | $CH_2$ | O | H | $C_2H_5$ | (2)Cl | (4)SO₂CH₃ | Z1 | (I-2) |
| 136 | — | $CH_2$ | O | H | $C_2H_5$ | (2)Cl | (4)SO₂CH₃ | Z2 | (I-2) logP = 1.58[a] |
| 137 | — | $CH_2$ | O | H | $C_3H_7$-i | (2)Cl | (4)Cl | Z1 | (I-2) |
| 138 | — | $CH_2$ | O | H | $C_3H_7$-i | (2)Cl | (4)Cl | Z2 | (I-2) |
| 139 | — | $CH_2$ | O | H | $C_3H_7$-i | (2)Cl | (4)SO₂CH₃ | Z1 | (I-2) |
| 140 | — | $CH_2$ | O | H | $C_3H_7$-i | (2)Cl | (4)SO₂CH₃ | Z2 | (I-2) |
| 141 | — | $CH_2$ | O | H | $CH_2CH=CH_2$ | (2)Cl | (4)Cl | Z1 | (I-2) |
| 142 | — | $CH_2$ | O | H | $CH_2CH=CH_2$ | (2)Cl | (4)Cl | Z2 | (I-2) |
| 143 | — | $CH_2$ | O | H | $CH_2CH=CH_2$ | (2)Cl | (4)SO₂CH₃ | Z1 | (I-2) |
| 144 | — | $CH_2$ | O | H | $CH_2CH=CH_2$ | (2)Cl | (4)SO₂CH₃ | Z2 | (I-2) |
| 145 | — | $CH_2$ | O | $CH_3$ | $CH_3$ | (2)Cl | (4)SO₂CH₃ | Z1 | (I-2) logP = 2.49[a] |
| 146 | — | $CH_2$ | O | $CH_3$ | $CH_3$ | (2)Cl | (4)Cl | Z1 | (I-2) |
| 147 | — | $CH_2$ | O | $C_2H_5$ | $CH_3$ | (2)Cl | (4)Cl | Z2 | (I-2) |
| 148 | — | $CH_2$ | O | $C_2H_5$ | $CH_3$ | (2)Cl | (4)Cl | Z1 | (I-2) logP = 3.63[a] |
| 149 | — | $CH_2$ | O | $C_2H_5$ | $CH_3$ | (2)Cl | (4)SO₂CH₃ | Z2 | (I-2) logP = 2.16[a] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 150 | — | $CH_2$ | O | $C_2H_5$ | $CH_3$ | (2)Cl | (4)$SO_2CH_3$ | Z1 | (I-2) logP = 2.87[a] |
| 151 | — | $CH_2$ | O | 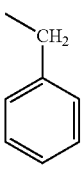 | $CH_3$ | (2)Cl | (4)Cl | Z2 | (I-2) |
| 152 | — | $CH_2$ | O | 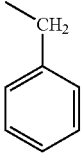 | $CH_3$ | (2)Cl | (4)Cl | Z1 | (I-2) |
| 153 | — | $CH_2$ | O | 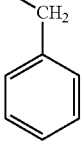 | $CH_3$ | (2)Cl | (4)$SO_2CH_3$ | Z2 | (I-2) logP = 2.82[a] |
| 154 | — | $CH_2$ | O | 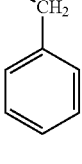 | $CH_3$ | (2)Cl | (4)$SO_2CH_3$ | Z1 | (I-2) |
| 155 | — | $CH_2$ | O | 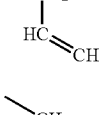 | $CH_3$ | (2)Cl | (4)Cl | Z2 | (I-2) |
| 156 | — | $CH_2$ | O | 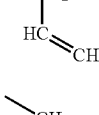 | $CH_3$ | (2)Cl | (4)Cl | Z1 | (I-2) |
| 157 | — | $CH_2$ | O | 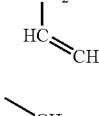 | $CH_3$ | (2)Cl | (4)$SO_2CH_3$ | Z2 | (I-2) logP = 2.29[a] |
| 158 | — | $CH_2$ | O | 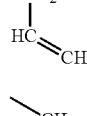 | $CH_3$ | (2)Cl | (4)$SO_2CH_3$ | Z1 | (I-2) logP = 3.01[a] |
| 159 | — | $CH_2$ | O |  | $CH_3$ | (2)Cl | (4)Cl | Z2 | (I-2) |
| 160 | — | $CH_2$ | O |  | $CH_3$ | (2)Cl | (4)Cl | Z1 | (I-2) |

TABLE 1-continued

Examples of compounds of the formula (I)

| Ex. No. | $A^1$ | $A^2$ | $A^3$ | $R^1$ | $R^2$ | (position) X | (position) Y | data | Formula Physical |
|---|---|---|---|---|---|---|---|---|---|
| 161 | — | $CH_2$ | O | 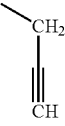 | $CH_3$ | (2)Cl | (4)$SO_2CH_3$ | Z2 | (I-2) |
| 162 | — | $CH_2$ | O |  | $CH_3$ | (2)Cl | (4)$SO_2CH_3$ | Z1 | (I-2) |
| 163 | — | $CH_2$ | O | 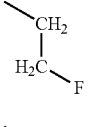 | $CH_3$ | (2)Cl | (4)Cl | Z2 | (I-2) |
| 164 | — | $CH_2$ | O | 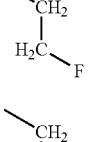 | $CH_3$ | (2)Cl | (4)Cl | Z1 | (I-2) |
| 165 | — | $CH_2$ | O |  | $CH_3$ | (2)Cl | (4)$SO_2CH_3$ | Z2 | (I-2) |
| 166 | — | $CH_2$ | O |  | $CH_3$ | (2)Cl | (4)$SO_2CH_3$ | Z1 | (I-2) |
| 167 | O | $(CH_2)_2$ | $SO_2$ | H | $C_3H_7$-n | (2)Cl | (4)Cl | Z2 | (I-2) logP = 2.15[a)] |
| 168 | O | $(CH_2)_2$ | $SO_2$ | H | $C_3H_7$-n | (2)Cl | (4)Cl | Z1 | (I-2) logP = 2.67[a)] |
| 169 | O | $(CH_2)_2$ | $SO_2$ | H | $C_3H_7$-n | (2)Cl | (4)$SO_2CH_3$ | Z2 | (I-2) |
| 170 | O | $(CH_2)_2$ | $SO_2$ | H | $C_3H_7$-n | (2)Cl | (4)$SO_2CH_3$ | Z1 | (I-2) |
| 171 | O | $(CH_2)_3$ | O | H | $CH_3$ | (2)Cl | (4)Cl | Z2 | (I-2) |
| 172 | O | $(CH_2)_3$ | O | H | $CH_3$ | (2)Cl | (4)Cl | Z1 | (I-2) |
| 173 | O | $(CH_2)_3$ | O | H | $CH_3$ | (2)Cl | (4)$SO_2CH_3$ | Z2 | (I-2) |
| 174 | O | $(CH_2)_3$ | O | H | $CH_3$ | (2)Cl | (4)$SO_2CH_3$ | Z1 | (I-2) |
| 175 | O | $(CH_2)_3$ | O | $CH_3$ | $CH_3$ | (2)Cl | (4)Cl | Z2 | (I-2) |
| 176 | O | $(CH_2)_3$ | O | $CH_3$ | $CH_3$ | (2)Cl | (4)Cl | Z1 | (I-2) |
| 177 | O | $(CH_2)_3$ | O | H | $C_2H_5$ | (2)Cl | (4)Cl | Z2 | (I-2) |
| 178 | O | $(CH_2)_3$ | O | H | $C_2H_5$ | (2)Cl | (4)Cl | Z1 | (I-2) |
| 179 | O | $(CH_2)_3$ | O | H | $C_2H_5$ | (2)Cl | (4)$SO_2CH_3$ | Z2 | (I-2) |
| 180 | O | $(CH_2)_3$ | O | H | $C_2H_5$ | (2)Cl | (4)$SO_2CH_3$ | Z1 | (I-2) |
| 181 | O | $(CH_2)_3$ | O | H | $C_3H_7$-i | (2)Cl | (4)Cl | Z2 | (I-2) |
| 182 | O | $(CH_2)_3$ | O | H | $C_3H_7$-i | (2)Cl | (4)Cl | Z1 | (I-2) |
| 183 | O | $(CH_2)_3$ | O | H | $C_3H_7$-i | (2)Cl | (4)$SO_2CH_3$ | Z2 | (I-2) |
| 184 | O | $(CH_2)_3$ | O | H | $C_3H_7$-i | (2)Cl | (4)$SO_2CH_3$ | Z1 | (I-2) |
| 185 | O | $(CH_2)_3$ | O | H | $CH_2CH=CH_2$ | (2)Cl | (4)Cl | Z2 | (I-2) |
| 186 | O | $(CH_2)_3$ | O | H | $CH_2CH=CH_2$ | (2)Cl | (4)Cl | Z2 | (I-2) |
| 187 | O | $(CH_2)_2$ | O | $C_2H_5$ | $CH_3$ | (2)Cl | (4)Cl | Z2 | (I-2) |
| 188 | O | $(CH_2)_2$ | O | $C_2H_5$ | $CH_3$ | (2)Cl | (4)Cl | Z1 | (I-2) |
| 189 | O | $(CH_2)_2$ | O | $C_2H_5$ | $CH_3$ | (2)Cl | (4)$SO_2CH_3$ | Z2 | (I-2) |
| 190 | O | $(CH_2)_2$ | O | $C_2H_5$ | $CH_3$ | (2)Cl | (4)$SO_2CH_3$ | Z1 | (I-2) |
| 191 | O | $(CH_2)_3$ | O | $C_2H_5$ | $CH_3$ | (2)Cl | (4)Cl | Z2 | (I-2) |
| 192 | O | $(CH_2)_3$ | O | $C_2H_5$ | $CH_3$ | (2)Cl | (4)Cl | Z1 | (I-2) |
| 193 | O | $(CH_2)_3$ | O | $C_2H_5$ | $CH_3$ | (2)Cl | (4)$SO_2CH_3$ | Z2 | (I-2) |
| 194 | O | $(CH_2)_3$ | O | $C_2H_5$ | $CH_3$ | (2)Cl | (4)$SO_2CH_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 195 | — | CH$_2$ | * | H | 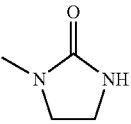 | (2)Cl | (4)Cl | Z2 | (I-2) |
| 196 | — | CH$_2$ | * | H | 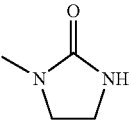 | (2)Cl | (4)Cl | Z1 | (I-2) Fp.: 148° C. |
| 197 | — | CH$_2$ | * | H | 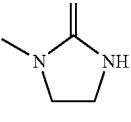 | (2)Cl | (4)SO$_2$CH$_3$ | Z2 | (I-2) |
| 198 | — | CH$_2$ | * | H | 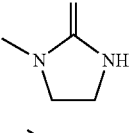 | (2)Cl | (4)SO$_2$CH$_3$ | Z1 | (I-2) |
| 199 | — | CH$_2$ | O | H | 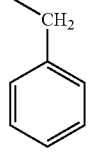 | (2)Cl | (4)SO$_2$CH$_3$ | Z1 | (I-2) logP = 3.04$^{a)}$ |
| 200 | — | CH$_2$ | O | H | 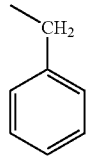 | (2)Cl | (4)SO$_2$CH$_3$ | Z2 | (I-2) logP = 2.31$^{a)}$ |
| 201 | — | CH$_2$ | O | H | 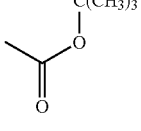 | (2)Cl | (4)SO$_2$CH$_3$ | Z1 | (I-2) |
| 201 | — | CH$_2$ | O | H | 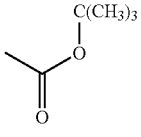 | (2)Cl | (4)SO$_2$CH$_3$ | Z2 | (I-2) |
| 202 | — | CH$_2$ | O | 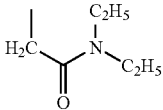 | CH$_3$ | (2)Cl | (4)SO$_2$CH$_3$ | Z1 | (I-2) |
| 203 | — | CH$_2$ | O | 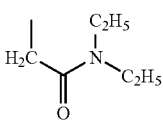 | C$_2$H$_5$ | (2)Cl | (4)SO$_2$CH$_3$ | Z1 | (I-2) |
| 204 | — | CH$_2$ | O | C$_3$H$_7$-i | CH$_3$ | (2)Cl | (4)SO$_2$CH$_3$ | Z1 | (I-2) |

TABLE 1-continued

Examples of compounds of the formula (I)

| Ex. No. | A¹ | A² | A³ | R¹ | R² | (position) X | (position) Y | Physical data | Formula |
|---|---|---|---|---|---|---|---|---|---|
| 205 | — | $CH_2$ | O | $C_3H_7$-i | $C_2H_5$ | (2)Cl | (4)$SO_2CH_3$ | Z1 | (I-2) |
| 206 | — | $CH_2$ | O | (phenyl-C(O)-CH($CH_3$)-) | $CH_3$ | (2)Cl | (4)$SO_2CH_3$ | Z1 | (I-2) |
| 207 | — | $CH_2$ | O | (phenyl-C(O)-CH($CH_3$)-) | $C_2H_5$ | (2)Cl | (4)$SO_2CH_3$ | Z1 | (I-2) |
| 208 | — | $CH_2$ | O | ($CH_3$-C(O)-CH($CH_3$)-) | $CH_3$ | (2)Cl | (4)$SO_2CH_3$ | Z1 | (I-2) |
| 209 | — | $CH_2$ | O | ($CH_3$-C(O)-CH($CH_3$)-) | $C_2H_5$ | (2)Cl | (4)$SO_2CH_3$ | Z1 | (I-2) |
| 210 | — | $CH_2$ | O | (phenyl-CH($CH_3$)-) | $CH_3$ | (2)Cl | (4)$SO_2CH_3$ | Z1 | (I-2) |
| 211 | — | $CH_2$ | O | (phenyl-CH($CH_3$)-) | $C_2H_5$ | (2)Cl | (4)$SO_2CH_3$ | Z1 | (I-2) |
| 212 | — | $CH_2$ | O | ($CH_3$($CH_3$O)N-C(O)-CH($CH_3$)-) | $CH_3$ | (2)Cl | (4)$SO_2CH_3$ | Z1 | (I-2) |
| 213 | — | $CH_2$ | O | ($CH_3$($CH_3$O)N-C(O)-CH($CH_3$)-) | $C_2H_5$ | (2)Cl | (4)$SO_2CH_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 214 | — | $CH_2$ | O | pyridin-2-yl-$CH_2$ | $CH_3$ | (2)Cl | (4)$SO_2CH_3$ | Z1 | (I-2) |
| 215 | — | $CH_2$ | O | pyridin-2-yl-$CH_2$ | $C_2H_5$ | (2)Cl | (4)$SO_2CH_3$ | Z1 | (I-2) |
| 216 | — | $CH_2$ | O | pyridin-3-yl-$CH_2$ | $CH_3$ | (2)Cl | (4)$SO_2CH_3$ | Z1 | (I-2) logP = 1.47[a] |
| 217 | — | $CH_2$ | O | pyridin-3-yl-$CH_2$ | $C_2H_5$ | (2)Cl | (4)$SO_2CH_3$ | Z1 | (I-2) |
| 218 | — | $CH_2$ | O | pyridin-4-yl-$CH_2$ | $CH_3$ | (2)Cl | (4)$SO_2CH_3$ | Z1 | (I-2) |
| 219 | — | $CH_2$ | O | pyridin-4-yl-$CH_2$ | $C_2H_5$ | (2)Cl | (4)$SO_2CH_3$ | Z1 | (I-2) |
| 220 | — | $CH_2$ | O | $(H_3C)(CH_3)N-CH_2$ | $CH_3$ | (2)Cl | (4)$SO_2CH_3$ | Z1 | (I-2) |
| 221 | — | $CH_2$ | O | $(H_3C)(CH_3)N-CH_2$ | $C_2H_5$ | (2)Cl | (4)$SO_2CH_3$ | Z1 | (I-2) |
| 222 | — | $CH_2$ | O | thiazol-2-yl-$CH_2$ | $CH_3$ | (2)Cl | (4)$SO_2CH_3$ | Z1 | (I-2) |
| 223 | — | $CH_2$ | O | thiazol-2-yl-$CH_2$ | $C_2H_5$ | (2)Cl | (4)$SO_2CH_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 224 | — | $CH_2$ | O | $CH_3OCH_2CH(-)$ | $CH_3$ | (2)Cl | (4)$SO_2CH_3$ | Z1 | (I-2) |
| 225 | — | $CH_2$ | O | $CH_3OCH_2CH(-)$ | $C_2H_5$ | (2)Cl | (4)$SO_2CH_3$ | Z1 | (I-2) |
| 226 | — | $CH_2$ | O | $CH_3OCH_2CH_2CH(-)$ | $CH_3$ | (2)Cl | (4)$SO_2CH_3$ | Z1 | (I-2) |
| 227 | — | $CH_2$ | O | $CH_3OCH_2CH_2CH(-)$ | $C_2H_5$ | (2)Cl | (4)$SO_2CH_3$ | Z1 | (I-2) |
| 228 | — | $CH_2$ | O | tetrahydropyran-2-yl-CH(-) | $CH_3$ | (2)Cl | (4)$SO_2CH_3$ | Z1 | (I-2) |
| 229 | — | $CH_2$ | O | tetrahydropyran-2-yl-CH(-) | $C_2H_5$ | (2)Cl | (4)$SO_2CH_3$ | Z1 | (I-2) |
| 230 | O | $(CH_2)_2$ | O | H | $C_6H_5CH_2$ | (2)Cl | (4)$SO_2CH_3$ | Z1 | (I-2) |
| 231 | O | $(CH_2)_2$ | O | H | $C_6H_5CH_2$ | (2)Cl | (4)$SO_2CH_3$ | Z2 | (I-2) |
| 232 | O | $(CH_2)_2$ | O | H | $CH_3C(O)OC(CH_3)_3$ | (2)Cl | (4)$SO_2CH_3$ | Z1 | (I-2) |

TABLE 1-continued

Examples of compounds of the formula (I)

| Ex. No. | $A^1$ | $A^2$ | $A^3$ | $R^1$ | $R^2$ | (position) X | (position) Y | Physical data | Formula |
|---|---|---|---|---|---|---|---|---|---|
| 233 | O | $(CH_2)_2$ | O | H | $C(CH_3)_3$-O-C(=O)-CH_2- (tert-butyl acetate group) | (2)Cl | (4)SO$_2$CH$_3$ | Z2 | (I-2) |
| 234 | O | $(CH_2)_2$ | O | $(C_2H_5)_2N-C(=O)-CH(CH_3)-CH_2-$ | CH$_3$ | (2)Cl | (4)SO$_2$CH$_3$ | Z1 | (I-2) |
| 235 | O | $(CH_2)_2$ | O | $(C_2H_5)_2N-C(=O)-CH(CH_3)-CH_2-$ | C$_2$H$_5$ | (2)Cl | (4)SO$_2$CH$_3$ | Z1 | (I-2) |
| 236 | O | $(CH_2)_2$ | O | $C_3H_7$-i | CH$_3$ | (2)Cl | (4)SO$_2$CH$_3$ | Z1 | (I-2) |
| 237 | O | $(CH_2)_2$ | O | $C_3H_7$-i | C$_2$H$_5$ | (2)Cl | (4)SO$_2$CH$_3$ | Z1 | (I-2) |
| 238 | O | $(CH_2)_2$ | O | Ph-C(=O)-CH(CH$_3$)-CH$_2$- | CH$_3$ | (2)Cl | (4)SO$_2$CH$_3$ | Z1 | (I-2) |
| 239 | O | $(CH_2)_2$ | O | Ph-C(=O)-CH(CH$_3$)-CH$_2$- | C$_2$H$_5$ | (2)Cl | (4)SO$_2$CH$_3$ | Z1 | (I-2) |
| 240 | O | $(CH_2)_2$ | O | CH$_3$-C(=O)-CH(CH$_3$)-CH$_2$- | CH$_3$ | (2)Cl | (4)SO$_2$CH$_3$ | Z1 | (I-2) |
| 241 | O | $(CH_2)_2$ | O | CH$_3$-C(=O)-CH(CH$_3$)-CH$_2$- | C$_2$H$_5$ | (2)Cl | (4)SO$_2$CH$_3$ | Z1 | (I-2) |
| 242 | O | $(CH_2)_2$ | O | Ph-CH(CH$_3$)-CH(CH$_3$)- | CH$_3$ | (2)Cl | (4)SO$_2$CH$_3$ | Z1 | (I-2) |
| 243 | O | $(CH_2)_2$ | O | Ph-CH(CH$_3$)-CH(CH$_3$)- | C$_2$H$_5$ | (2)Cl | (4)SO$_2$CH$_3$ | Z1 | (I-2) |

TABLE 1-continued

Examples of compounds of the formula (I)

| Ex. No. | $A^1$ | $A^2$ | $A^3$ | $R^1$ | $R^2$ | (position) X | (position) Y | Physical data | Formula |
|---|---|---|---|---|---|---|---|---|---|
| 244 | O | (CH$_2$)$_2$ | O | CH$_3$-CH$_2$-C(=O)-N(CH$_3$)-O-CH$_3$ | CH$_3$ | (2)Cl | (4)SO$_2$CH$_3$ | Z1 | (I-2) |
| 245 | O | (CH$_2$)$_2$ | O | CH$_3$-CH$_2$-C(=O)-N(CH$_3$)-O-CH$_3$ | C$_2$H$_5$ | (2)Cl | (4)SO$_2$CH$_3$ | Z1 | (I-2) |
| 246 | O | (CH$_2$)$_2$ | O | 2-pyridyl-CH$_2$- | CH$_3$ | (2)Cl | (4)SO$_2$CH$_3$ | Z1 | (I-2) |
| 247 | O | (CH$_2$)$_2$ | O | 2-pyridyl-CH$_2$- | C$_2$H$_5$ | (2)Cl | (4)SO$_2$CH$_3$ | Z1 | (I-2) |
| 248 | O | (CH$_2$)$_2$ | O | 3-pyridyl-CH$_2$- | CH$_3$ | (2)Cl | (4)SO$_2$CH$_3$ | Z1 | (I-2) |
| 249 | O | (CH$_2$)$_2$ | O | 3-pyridyl-CH$_2$- | C$_2$H$_5$ | (2)Cl | (4)SO$_2$CH$_3$ | Z1 | (I-2) |
| 250 | O | (CH$_2$)$_2$ | O | 4-pyridyl-CH$_2$- | CH$_3$ | (2)Cl | (4)SO$_2$CH$_3$ | Z1 | (I-2) |
| 251 | O | (CH$_2$)$_2$ | O | 4-pyridyl-CH$_2$- | C$_2$H$_5$ | (2)Cl | (4)SO$_2$CH$_3$ | Z1 | (I-2) |
| 252 | O | (CH$_2$)$_2$ | O | (CH$_3$)$_2$N-CH$_2$- | CH$_3$ | (2)Cl | (4)SO$_2$CH$_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 253 | O | (CH$_2$)$_2$ | O | 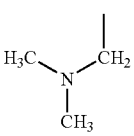 | C$_2$H$_5$ | (2)Cl | (4)SO$_2$CH$_3$ | Z1 | (I-2) |
| 254 | O | (CH$_2$)$_2$ | O | 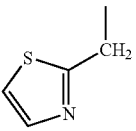 | CH$_3$ | (2)Cl | (4)SO$_2$CH$_3$ | Z1 | (I-2) |
| 255 | O | (CH$_2$)$_2$ | O | 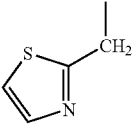 | C$_2$H$_5$ | (2)Cl | (4)SO$_2$CH$_3$ | Z1 | (I-2) |
| 256 | O | (CH$_2$)$_2$ | O | 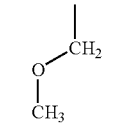 | CH$_3$ | (2)Cl | (4)SO$_2$CH$_3$ | Z1 | (I-2) |
| 257 | O | (CH$_2$)$_2$ | O | 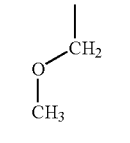 | C$_2$H$_5$ | (2)Cl | (4)SO$_2$CH$_3$ | Z1 | (I-2) |
| 258 | O | (CH$_2$)$_2$ | O | 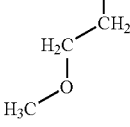 | CH$_3$ | (2)Cl | (4)SO$_2$CH$_3$ | Z1 | (I-2) |
| 259 | O | (CH$_2$)$_2$ | O | 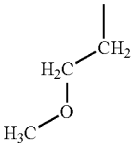 | C$_2$H$_5$ | (2)Cl | (4)SO$_2$CH$_3$ | Z1 | (I-2) |
| 260 | O | (CH$_2$)$_2$ | O | 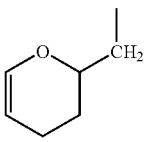 | CH$_3$ | (2)Cl | (4)SO$_2$CH$_3$ | Z1 | (I-2) |
| 261 | O | (CH$_2$)$_2$ | O | 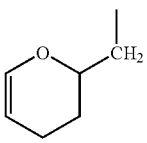 | C$_2$H$_5$ | (2)Cl | (4)SO$_2$CH$_3$ | Z1 | (I-2) |

TABLE 1-continued
Examples of compounds of the formula (I)
| Ex. No. | A¹ | A² | A³ | R¹ | R² | (position) X | (position) Y | data | Formula Physical |
|---|---|---|---|---|---|---|---|---|---|
| 262 | O | (CH₂)₃ | O | H | 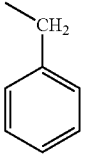 | (2)Cl | (4)SO₂CH₃ | Z1 | (I-2) |
| 263 | O | (CH₂)₃ | O | H | 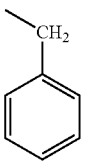 | (2)Cl | (4)SO₂CH₃ | Z2 | (I-2) |
| 264 | O | (CH₂)₃ | O | H | 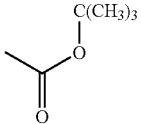 | (2)Cl | (4)SO₂CH₃ | Z1 | (I-2) |
| 265 | O | (CH₂)₃ | O | H | 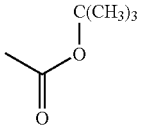 | (2)Cl | (4)SO₂CH₃ | Z2 | (I-2) |
| 266 | O | (CH₂)₃ | O | 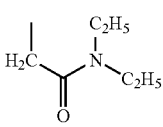 | CH₃ | (2)Cl | (4)SO₂CH₃ | Z1 | (I-2) |
| 267 | O | (CH₂)₃ | O | 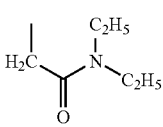 | C₂H₅ | (2)Cl | (4)SO₂CH₃ | Z1 | (I-2) |
| 268 | O | (CH₂)₃ | O | C₃H₇-i | CH₃ | (2)Cl | (4)SO₂CH₃ | Z1 | (I-2) |
| 269 | O | (CH₂)₃ | O | C₃H₇-i | C₂H₅ | (2)Cl | (4)SO₂CH₃ | Z1 | (I-2) |
| 270 | O | (CH₂)₃ | O | 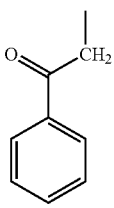 | CH₃ | (2)Cl | (4)SO₂CH₃ | Z1 | (I-2) |
| 271 | O | (CH₂)₃ | O | 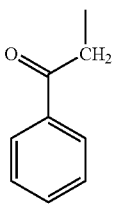 | C₂H₅ | (2)Cl | (4)SO₂CH₃ | Z1 | (I-2) |

TABLE 1-continued

Examples of compounds of the formula (I)

| Ex. No. | $A^1$ | $A^2$ | $A^3$ | $R^1$ | $R^2$ | (position) X | (position) Y | data | Formula Physical |
|---|---|---|---|---|---|---|---|---|---|
| 272 | O | $(CH_2)_3$ | O | CH(CH₃)-C(=O)-CH₃ | $CH_3$ | (2)Cl | (4)$SO_2CH_3$ | Z1 | (I-2) |
| 273 | O | $(CH_2)_3$ | O | CH(CH₃)-C(=O)-CH₃ | $C_2H_5$ | (2)Cl | (4)$SO_2CH_3$ | Z1 | (I-2) |
| 274 | O | $(CH_2)_3$ | O | CH(CH₃)-C₆H₅ | $CH_3$ | (2)Cl | (4)$SO_2CH_3$ | Z1 | (I-2) |
| 278 | O | $(CH_2)_3$ | O | CH(CH₃)-C₆H₅ | $C_2H_5$ | (2)Cl | (4)$SO_2CH_3$ | Z1 | (I-2) |
| 279 | O | $(CH_2)_3$ | O | CH(CH₃)-C(=O)-N(CH₃)(OCH₃) | $CH_3$ | (2)Cl | (4)$SO_2CH_3$ | Z1 | (I-2) |
| 280 | O | $(CH_2)_3$ | O | CH(CH₃)-C(=O)-N(CH₃)(OCH₃) | $C_2H_5$ | (2)Cl | (4)$SO_2CH_3$ | Z1 | (I-2) |
| 281 | O | $(CH_2)_3$ | O | CH(CH₃)-(2-pyridyl) | $CH_3$ | (2)Cl | (4)$SO_2CH_3$ | Z1 | (I-2) |
| 282 | O | $(CH_2)_3$ | O | CH(CH₃)-(2-pyridyl) | $C_2H_5$ | (2)Cl | (4)$SO_2CH_3$ | Z1 | (I-2) |
| 283 | O | $(CH_2)_3$ | O | CH(CH₃)-(3-pyridyl) | $CH_3$ | (2)Cl | (4)$SO_2CH_3$ | Z1 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 284 | O | (CH$_2$)$_3$ | O | 3-pyridyl-CH$_2$- | C$_2$H$_5$ | (2)Cl | (4)SO$_2$CH$_3$ | Z1 | (I-2) |
| 285 | O | (CH$_2$)$_3$ | O | 4-pyridyl-CH$_2$- | CH$_3$ | (2)Cl | (4)SO$_2$CH$_3$ | Z1 | (I-2) |
| 286 | O | (CH$_2$)$_3$ | O | 4-pyridyl-CH$_2$- | C$_2$H$_5$ | (2)Cl | (4)SO$_2$CH$_3$ | Z1 | (I-2) |
| 287 | O | (CH$_2$)$_3$ | O | (CH$_3$)$_2$N-CH$_2$- | CH$_3$ | (2)Cl | (4)SO$_2$CH$_3$ | Z1 | (I-2) |
| 289 | O | (CH$_2$)$_3$ | O | (CH$_3$)$_2$N-CH$_2$- | C$_2$H$_5$ | (2)Cl | (4)SO$_2$CH$_3$ | Z1 | (I-2) |
| 290 | O | (CH$_2$)$_3$ | O | 2-thiazolyl-CH$_2$- | CH$_3$ | (2)Cl | (4)SO$_2$CH$_3$ | Z1 | (I-2) |
| 291 | O | (CH$_2$)$_3$ | O | 2-thiazolyl-CH$_2$- | C$_2$H$_5$ | (2)Cl | (4)SO$_2$CH$_3$ | Z1 | (I-2) |
| 292 | O | (CH$_2$)$_3$ | O | CH$_3$-O-CH$_2$- | CH$_3$ | (2)Cl | (4)SO$_2$CH$_3$ | Z1 | (I-2) |
| 293 | O | (CH$_2$)$_3$ | O | CH$_3$-O-CH$_2$- | C$_2$H$_5$ | (2)Cl | (4)SO$_2$CH$_3$ | Z1 | (I-2) |
| 294 | O | (CH$_2$)$_3$ | O | CH$_3$-O-CH$_2$-CH$_2$- | CH$_3$ | (2)Cl | (4)SO$_2$CH$_3$ | Z1 | (I-2) |

TABLE 1-continued

Examples of compounds of the formula (I)

| Ex. No. | A$^1$ | A$^2$ | A$^3$ | R$^1$ | R$^2$ | (position) X | (position) Y | data | Formula Physical |
|---|---|---|---|---|---|---|---|---|---|
| 295 | O | (CH$_2$)$_3$ | O | 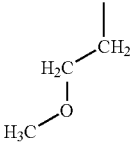 | C$_2$H$_5$ | (2)Cl | (4)SO$_2$CH$_3$ | Z1 | (I-2) |
| 296 | O | (CH$_2$)$_3$ | O | 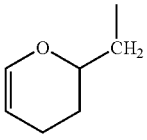 | CH$_3$ | (2)Cl | (4)SO$_2$CH$_3$ | Z1 | (I-2) |
| 297 | O | (CH$_2$) | O | 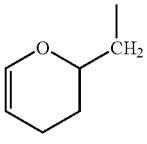 | C$_2$H$_5$ | (2)Cl | (4)SO$_2$CH$_3$ | Z1 | (I-2) |
| 298 | CH$_2$ | — | O | H | CH$_3$ | (2)Cl | (4)CH$_3$SO$_2$ | 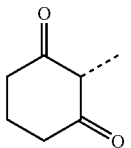 | (I-2) |
| 299 | CH$_2$ | — | O | H | CH$_3$ | (2)Cl | (4)CH$_3$SO$_2$ | Z2 | (I-2) 1.20 |
| 300 | CH$_2$ | — | O | H | CH$_3$ | (2)Cl | (4)CH$_3$SO$_2$ | Z4 | (I-2) |
| 301 | CH$_2$ | — | O | H | CH$_3$ | (2)Cl | (4)CH$_3$SO$_2$ | Z3 | (I-2) |
| 302 | CH$_2$ | — | O | H | CH$_3$ | (2)Cl | (4)CH$_3$SO$_2$ | 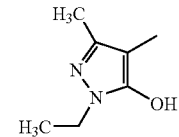 | (I-2) |
| 303 | CH$_2$ | — | O | CH$_3$ | CH$_3$ | (2)Cl | (4)CH$_3$SO$_2$ | 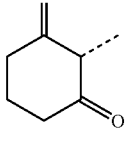 | (I-2) 2.49 |
| 304 | CH$_2$ | — | O | CH$_3$ | CH$_3$ | (2)Cl | (4)CH$_3$SO$_2$ | Z2 | (I-2) 1.78 |
| 305 | CH$_2$ | — | O | CH$_3$ | CH$_3$ | (2)Cl | (4)CH$_3$SO$_2$ | Z4 | (I-2) |
| 306 | CH$_2$ | — | O | CH$_3$ | CH$_3$ | (2)Cl | (4)CH$_3$SO$_2$ | 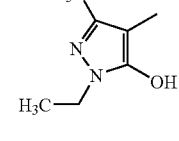 | (I-2) |
| 307 | CH$_2$ | — | O | CH$_3$ | CH$_3$ | (2)Cl | (4)CH$_3$SO$_2$ | Z3 | (I-2) 1.45 |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 308 | $CH_2$ | — | O | $CH_2CH_3$ | $CH_3$ | (2)Cl | (4)$CH_3SO_2$ | 2-methyl-cyclohexane-1,3-dione | (I-2) 2.87 |
| 309 | $CH_2$ | — | O | $CH_2CH_3$ | $CH_3$ | (2)Cl | (4)$CH_3SO_2$ | Z2 | (I-2) 2.16 |
| 310 | $CH_2$ | — | O | $CH_2CH_3$ | $CH_3$ | (2)Cl | (4)$CH_3SO_2$ | Z4 | (I-2) 1.84 |
| 311 | $CH_2$ | — | O | $CH_2CH_3$ | $CH_3$ | (2)Cl | (4)$CH_3SO_2$ | 1-ethyl-3,4-dimethyl-5-hydroxypyrazole | (I-2) |
| 312 | $CH_2$ | — | O | $CH_2CH_3$ | $CH_3$ | (2)Cl | (4)$CH_3SO_2$ | Z3 | (I-2) |
| 313 | $CH_2$ | — | O | $CH_2CH_2F$ | $CH_3$ | (2)Cl | (4)$CH_3SO_2$ | 2-methyl-cyclohexane-1,3-dione | (I-2) |
| 314 | $CH_2$ | — | O | $CH_2CH_2F$ | $CH_3$ | (2)Cl | (4)$CH_3SO_2$ | Z2 | (I-2) |
| 315 | $CH_2$ | — | O | $CH_2CH_2F$ | $CH_3$ | (2)Cl | (4)$CH_3SO_2$ | Z4 | (I-2) |
| 316 | $CH_2$ | — | O | $CH_2CH_2F$ | $CH_3$ | (2)Cl | (4)$CH_3SO_2$ | 1-ethyl-3,4-dimethyl-5-hydroxypyrazole | (I-2) |
| 317 | $CH_2$ | — | O | $CH_2CH_2F$ | $CH_3$ | (2)Cl | (4)$CH_3SO_2$ | Z3 | (I-2) |
| 318 | $CH_2$ | — | O | $CH_2$-cyclopropyl | $CH_3$ | (2)Cl | (4)$CH_3SO_2$ | 2-methyl-cyclohexane-1,3-dione | (I-2) |
| 319 | $CH_2$ | — | O | $CH_2$-cyclopropyl | $CH_3$ | (2)Cl | (4)$CH_3SO_2$ | Z2 | (I-2) |
| 320 | $CH_2$ | — | O | $CH_2$-cyclopropyl | $CH_3$ | (2)Cl | (4)$CH_3SO_2$ | Z4 | (I-2) |
| 321 | $CH_2$ | — | O | $CH_2$-cyclopropyl | $CH_3$ | (2)Cl | (4)$CH_3SO_2$ | 1-ethyl-3,4-dimethyl-5-hydroxypyrazole | (I-2) |
| 322 | $CH_2$ | — | O | $CH_2$-cyclopropyl | $CH_3$ | (2)Cl | (4)$CH_3SO_2$ | Z3 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 323 | $CH_2$ | — | O | $CH_2CHCH_2$ | $CH_3$ | (2)Cl | (4)$CH_3SO_2$ | 2-methyl-cyclohexane-1,3-dione | (I-2) |
| 324 | $CH_2$ | — | O | $CH_2CHCH_2$ | $CH_3$ | (2)Cl | (4)$CH_3SO_2$ | Z2 | (I-2) |
| 325 | $CH_2$ | — | O | $CH_2CHCH_2$ | $CH_3$ | (2)Cl | (4)$CH_3SO_2$ | Z4 | (I-2) |
| 326 | $CH_2$ | — | O | $CH_2CHCH_2$ | $CH_3$ | (2)Cl | (4)$CH_3SO_2$ | Z2 | (I-2) |
| 327 | $CH_2$ | — | O | $CH_2CHCH_2$ | $CH_3$ | (2)Cl | (4)$CH_3SO_2$ | Z3 | (I-2) |
| 328 | $CH_2$ | — | O | $CH_2CCH$ | $CH_3$ | (2)Cl | (4)$CH_3SO_2$ | 2-methyl-cyclohexane-1,3-dione | (I-2) |
| 329 | $CH_2$ | — | O | $CH_2CCH$ | $CH_3$ | (2)Cl | (4)$CH_3SO_2$ | Z2 | (I-2) |
| 330 | $CH_2$ | — | O | $CH_2CCH$ | $CH_3$ | (2)Cl | (4)$CH_3SO_2$ | Z4 | (I-2) |
| 331 | $CH_2$ | — | O | $CH_2CCH$ | $CH_3$ | (2)Cl | (4)$CH_3SO_2$ | 1-ethyl-3,4-dimethyl-5-hydroxy-pyrazole | (I-2) |
| 332 | $CH_2$ | — | O | $CH_2CCH$ | $CH_3$ | (2)Cl | (4)$CH_3SO_2$ | Z3 | (I-2) |
| 333 | $CH_2$ | — | O | $CH_2$Phenyl | $CH_3$ | (2)Cl | (4)$CH_3SO_2$ | 2-methyl-cyclohexane-1,3-dione | (I-2) |
| 334 | $CH_2$ | — | O | $CH_2$Phenyl | $CH_3$ | (2)Cl | (4)$CH_3SO_2$ | Z2 | (I-2) 2.82 |
| 335 | $CH_2$ | — | O | $CH_2$Phenyl | $CH_3$ | (2)Cl | (4)$CH_3SO_2$ | Z4 | (I-2) 2.48 |
| 336 | $CH_2$ | — | O | $CH_2$PhenyI | $CH_3$ | (2)Cl | (4)$CH_3SO_2$ | 1-ethyl-3,4-dimethyl-5-hydroxy-pyrazole | (I-2) |
| 337 | $CH_2$ | — | O | $CH_2$Phenyl | $CH_3$ | (2)Cl | (4)$CH_3SO_2$ | Z3 | (I-2) |
| 338 | $CH_2$ | — | O | $CH_2C(O)N(CH_2CH_3)_2$ | $CH_3$ | (2)Cl | (4)$CH_3SO_2$ | 2-methyl-cyclohexane-1,3-dione | (I-2) |
| 339 | $CH_2$ | — | O | $CH_2C(O)N(CH_2CH_3)_2$ | $CH_3$ | (2)Cl | (4)$CH_3SO_2$ | Z2 | (I-2) |
| 340 | $CH_2$ | — | O | $CH_2C(O)N(CH_2CH_3)_2$ | $CH_3$ | (2)Cl | (4)$CH_3SO_2$ | Z4 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 341 | CH₂ | — | O | CH₂C(O)N(CH₂CH₃)₂ | CH₃ | (2)Cl | (4)CH₃SO₂ | (pyrazole structure with H₃C, N, OH, H₃C-) | (I-2) |
| 342 | CH₂ | — | O | CH₂C(O)N(CH₂CH₃)₂ | CH₃ | (2)Cl | (4)CH₃SO₂ | Z3 | (I-2) |
| 343 | CH₂ | — | O | CH(CH₃)₂ | CH₃ | (2)Cl | (4)CH₃SO₂ | (cyclohexanedione structure) | (I-2) 3.26 |
| 344 | CH₂ | — | O | CH(CH₃)₂ | CH₃ | (2)Cl | (4)CH₃SO₂ | Z2 | (I-2) 2.52 |
| 345 | CH₂ | — | O | CH(CH₃)₂ | CH₃ | (2)Cl | (4)CH₃SO₂ | Z4 | (I-2) 2.16 |
| 346 | CH₂ | — | O | CH(CH₃)₂ | CH₃ | (2)Cl | (4)CH₃SO₂ | (pyrazole structure) | (I-2) |
| 347 | CH₂ | — | O | CH(CH₃)₂ | CH₃ | (2)Cl | (4)CH₃SO₂ | Z3 | (I-2) |
| 348 | CH₂ | — | O | H | CH₂Phenyl | (2)Cl | (4)CH₃SO₂ | (cyclohexanedione structure) | (I-2) 3.04 |
| 349 | CH₂ | — | O | H | CH₂Phenyl | (2)Cl | (4)CH₃SO₂ | Z2 | (I-2) 2.31 |
| 350 | CH₂ | — | O | H | CH₂Phenyl | (2)Cl | (4)CH₃SO₂ | Z4 | (I-2) |
| 351 | CH₂ | — | O | H | CH₂Phenyl | (2)Cl | (4)CH₃SO₂ | (pyrazole structure) | (I-2) |
| 352 | CH₂ | — | O | H | CH₂Phenyl | (2)Cl | (4)CH₃SO₂ | Z3 | (I-2) |
| 353 | O | (CH₂)₂ | SO₂ | H | CH₃ | (2)Cl | (4)Cl | Z4 | (I-2) logP = 1.36[a] |
| 354 | O | (CH₂)₂ | SO₂ | H | CH₃ | (2)Cl | (4)Cl | Z2 | (I-2) logP = 1.54[a] |
| 355 | O | (CH₂)₂ | SO₂ | H | CH₃ | (2)Cl | (4)Cl | Z3 | (I-2) logP = 1.32[a] |
| 356 | O | (CH₂)₂ | SO₂ | CH₃ | (p-tolyl structure) | (2)Cl | (4)Cl | Z2 | (I-2) |
| 357 | O | (CH₂)₂ | SO₂ | H | CH₃ | (2)Br | (4)Br | (bicyclic diketone OH structure) | (I-2) logP = 2.52[a] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 358 | O | (CH$_2$)$_2$ | SO$_2$ | H | C$_2$H$_5$ | (2)CH$_3$ | (4)Cl | Z2 | (I-2) logP = 2.03[a) |
| 359 | O | (CH$_2$)$_2$ | SO$_2$ | H | C$_2$H$_5$ | (2)CH$_3$ | (4)Cl | Z1 | (I-2) logP = 2.33[a) |
| 360 | O | (CH$_2$)$_2$ | SO$_2$ | H | CH$_3$ | (2)CH$_3$ | (4)Cl | Z2 | (I-2) logP = 1.82[a) |
| 361 | O | (CH$_2$)$_2$ | SO$_2$ | H | CH$_3$ | (2)CH$_3$ | (4)Cl | Z1 | (I-2) logP = 2.13[a) |
| 362 | O | (CH$_2$)$_2$ | SO$_2$ | H | C$_2$H$_5$ | (2)CH$_3$ | (4)Br | Z2 | (I-2) logP = 2.09[a) |
| 363 | O | (CH$_2$)$_2$ | SO$_2$ | H | C$_2$H$_5$ | (2)CH$_3$ | (4)Br | Z4 | (I-2) logP = 1.77[a) |
| 364 | O | (CH$_2$)$_2$ | SO$_2$ | H | C$_2$H$_5$ | (2)CH$_3$ | (4)Br | Z1 | (I-2) logP = 2.41[a) |
| 365 | O | (CH$_2$)$_2$ | SO$_2$ | H | CH$_3$ | (2)CH$_3$ | (4)Br | Z2 | (I-2) logP = 1.89[a) |
| 366 | O | (CH$_2$)$_2$ | SO$_2$ | H | CH$_3$ | (2)CH$_3$ | (4)Br | Z4 | (I-2) logP = 1.56[a) |
| 367 | O | (CH$_2$)$_2$ | SO$_2$ | H | CH$_3$ | (2)CH$_3$ | (4)Br | Z1 | (I-2) logP = 2.19[a) |
| 368 | O | (CH$_2$)$_2$ | SO$_2$ | H | CH$_3$ | (2)Cl | (4)CH$_3$SO$_2$ | Z4 | (I-2) logP = 0.95[a) |
| 369 | — | CH$_2$ | O | C$_2$H$_5$ | CH$_3$ | (2)Cl | (4)CH$_3$SO$_2$ | Z4 | (I-2) logP = 1.84[a) |
| 370 | — | CH$_2$ | O | C$_3$H$_7$-i | CH$_3$ | (2)Cl | (4)CH$_3$SO$_2$ | Z2 | (I-2) logP = 2.52[a) |
| 371 | — | CH$_2$ | O | C$_3$H$_7$-i | CH$_3$ | (2)Cl | (4)CH$_3$SO$_2$ | Z4 | (I-2) logP = 2.16[a) |
| 372 | — | CH$_2$ | O | CH$_2$Phenyl | CH$_3$ | (2)Cl | (4)CH$_3$SO$_2$ | Z4 | (I-2) logP = 2.54[a) |
| 373 | — | CH$_2$ | O | 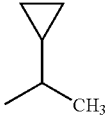 | CH$_3$ | (2)Cl | (4)C$_3$SO$_2$ | Z2 | (I-2) logP = 2.94[a) |
| 374 | — | CH$_2$ | O |  | CH$_3$ | (2)Cl | (4)CH$_3$SO$_2$ | Z4 | (I-2) logP = 2.53[a) |
| 375 | — | CH$_2$ | O |  | CH$_3$ | (2)Cl | (4)CH$_3$SO$_2$ | Z1 | (I-2) |
| 376 | — | CH$_2$ | O | 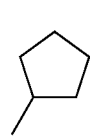 | CH$_3$ | (2)Cl | (4)CH$_3$SO$_2$ | Z1 | (I-2) |
| 377 | — | CH$_2$ | O | 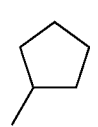 | CH$_3$ | (2)Cl | (4)CH$_3$SO$_2$ | 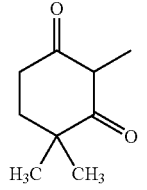 | (I-2) logP = 4.65[a) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 378 | — | CH$_2$ | O | 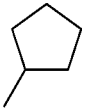 | CH$_3$ | (2)Cl | (4)CH$_3$SO$_2$ | Z4 | (I-2) logP = 2.59[a)] |
| 379 | — | CH$_2$ | O | 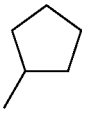 | CH$_3$ | (2)Cl | (4)CH$_3$SO$_2$ | Z2 | (I-2) logP = 2.99[a)] |
| 380 | — | CH$_2$ | O |  | CH$_3$ | (2)Cl | (4)CH$_3$SO$_2$ | Z1 | (I-2) logP = 3.31[a)] |
| 381 | — | CH$_2$ | O |  | CH$_3$ | (2)Cl | (4)CH$_3$SO$_2$ | Z2 | (I-2) logP = 2.58[a)] |
| 382 | — | CH$_2$ | O | 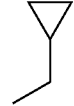 | CH$_3$ | (2)Cl | (4)CH$_3$SO$_2$ | Z4 | (I-2) logP = 2.22[a)] |
| 383 | — | CH$_2$ | O | 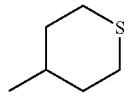 | CH$_3$ | (2)Cl | (4)CH$_3$SO$_2$ | Z1 | (I-2) logP = 3.33[a)] |
| 384 | — | CH$_2$ | O | 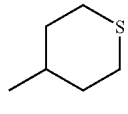 | CH$_3$ | (2)Cl | (4)CH$_3$SO$_2$ | Z2 | (I-2) logP = 2.59[a)] |
| 385 | — | CH$_2$ | O | CH$_3$ | CH$_3$ | (2)Cl | (4)CH$_3$SO$_2$ | 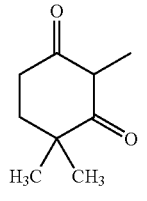 | (I-2) logP = 3.25[a)] |
| 386 | — | CH$_2$ | O | 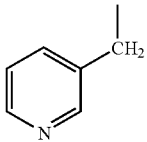 | CH$_3$ | (2)Cl | (4)CH$_3$SO$_2$ | Z4 | (I-2) logP = 0.64[a)] |
| 387 | — | CH$_2$ | O | 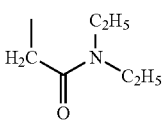 | CH$_3$ | (2)Cl | (4)CH$_3$SO$_2$ | 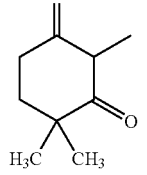 | (I-2) logP = 3.12[a)] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 388 | — | $CH_2$ | O | $CH_3CH(C_2H_5)C(O)N(C_2H_5)_2$ (1-methylpropanoyl diethylamide group) | $CH_3$ | (2)Cl | (4)$CH_3SO_2$ | Z4 | (I-2) logP = 1.59[a)] |
| 389 | — | $CH_2$ | O | $CH_3CH(C_2H_5)C(O)N(C_2H_5)_2$ | $CH_3$ | (2)Cl | (4)$CH_3SO_2$ | Z2 | (I-2) logP = 1.85[a)] |
| 390 | — | $CH_2$ | O | $C_2H_5$ | $C_2H_5$ | (2)Cl | (4)$CH_3SO_2$ | Z1 | (I-2) logP = 3.22[a)] |
| 391 | — | $CH_2$ | O | $C_2H_5$ | $C_2H_5$ | (2)Cl | (4)$CH_3SO_2$ | 2,2-dimethyl-1,3-cyclohexanedione | (I-2) logP = 4.08[a)] |
| 392 | — | $CH_2$ | O | $C_3H_7$-i | $C_2H_5$ | (2)Cl | (4)$CH_3SO_2$ | Z2 | (I-2) logP = 2.89[a)] |
| 393 | — | $CH_2$ | O | $CH_3$ | $C_3H_7$-i | (2)Cl | (4)$CH_3SO_2$ | Z1 | (I-2) logP = 3.14[a)] |
| 394 | — | $CH_2$ | O | tetrahydrothiopyran-4-yl | $CH_3$ | (2)Cl | (4)$CH_3SO_2$ | Z4 | (I-2) logP = 2.24[a)] |
| 395 | — | $CH_2$ | O | $CH_3$ | $C_3H_7$-i | (2)Cl | (4)$CH_3SO_2$ | Z2 | (I-2) logP = 2.33[a)] |
| 396 | — | $CH_2$ | O | $CH_3CH(CH_3)C(O)N(CH_3)_2$ | $CH_3$ | (2)Cl | (4)$CH_3SO_2$ | Z1 | (I-2) logP = 1.93[a)] |
| 397 | — | $CH_2$ | O | $CH_3$ | cyclopentyl | (2)Cl | (4)$CH_3SO_2$ | Z2 | (I-2) logP = 2.87[a)] |
| 398 | — | $CH_2$ | O | $CH_3$ | cyclopentyl | (2)Cl | (4)$CH_3SO_2$ | Z1 | (I-2) logP = 3.69[a)] |
| 399 | — | $CH_2$ | O | $C_3H_7$-i | $C_3H_7$-i | (2)Cl | (4)$CH_3SO_2$ | 2,2-dimethyl-1,3-cyclohexanedione | (I-2) logP = 4.80[a)] |
| 400 | — | $CH_2$ | O | $C_3H_7$-i | $C_3H_7$-i | (2)Cl | (4)$CH_3SO_2$ | Z4 | (I-2) logP = 2.81[a)] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 401 | — | CH$_2$ | O | H | 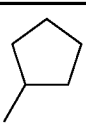 | (2)Cl | (4)CH$_3$SO$_2$ | Z1 | (I-2) logP = 3.07$^{a)}$ |
| 402 | — | CH$_2$ | O | C$_2$H$_5$ | C$_3$H$_7$-i | (2)Cl | (4)CH$_3$SO$_2$ | Z1 | (I-2) logP = 3.52$^{a)}$ |
| 403 | — | CH$_2$ | O | C$_2$H$_5$ | C$_3$H$_7$-i | (2)Cl | (4)CH$_3$SO$_2$ | 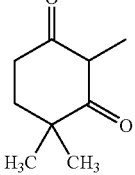 | (I-2) logP = 4.36$^{a)}$ |
| 404 | — | CH$_2$ | O | C$_2$H$_5$ | C$_3$H$_7$-i | (2)Cl | (4)CH$_3$SO$_2$ | Z2 | (I-2) logP = 2.79$^{a)}$ |
| 405 | — | CH$_2$ | O | C$_2$H$_5$ | CH$_3$ | (2)Cl | (4)CH$_3$SO$_2$ | 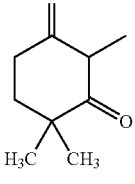 | (I-2) logP = 3.70$^{a)}$ |
| 406 | — | CH$_2$ | O | C$_2$H$_5$ | CH$_3$ | (2)Cl | (4)CH$_3$SO$_2$ | 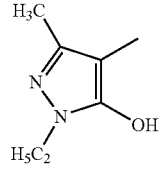 | (I-2) logP = 2.04$^{a)}$ |
| 407 | — | CH$_2$ | O | C$_2$H$_5$ | CH$_3$ | (2)Cl | (4)CH$_3$SO$_2$ | 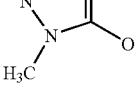 | (I-2) logP = 1.76$^{a)}$ |
| 408 | — | CH$_2$ | O | 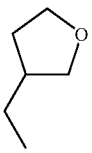 | CH$_3$ | (2)Cl | (4)CH$_3$SO$_2$ | Z1 | (I-2) logP = 2.50$^{a)}$ |
| 409 | — | CH$_2$ | O | 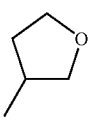 | CH$_3$ | (2)Cl | (4)CH$_3$SO$_2$ | Z1 | (I-2) logP = 2.32$^{a)}$ |
| 410 | — | CH$_2$ | O | 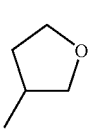 | CH$_3$ | (2)Cl | (4)CH$_3$SO$_2$ | Z2 | (I-2) logP = 1.70$^{a)}$ |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 411 | — | $CH_2$ | O | 3-(tetrahydro-2H-pyran-3-yl) | $CH_3$ | (2)Cl | (4)$CH_3SO_2$ | Z1 | (I-2) logP = 2.74[a] |
| 412 | — | $CH_2$ | O | 3-(tetrahydro-2H-pyran-3-yl) | $CH_3$ | (2)Cl | (4)$CH_3SO_2$ | Z2 | (I-2) logP = 2.01[a] |
| 413 | — | $CH_2$ | O | $CH_3$ | $C_2H_5$ | (2)Cl | (4)$CH_3SO_2$ | Z2 | (I-2) logP = 2.09[a] |
| 414 | — | $CH_2$ | O | $CH_3$ | $C_2H_5$ | (2)Cl | (4)$CH_3SO_2$ | Z4 | (I-2) logP = 1.71[a] |
| 415 | — | $CH_2$ | O | 3-ethyl-tetrahydrofuran-3-yl | $C_2H_5$ | (2)Cl | (4)$CH_3SO_2$ | Z1 | (I-2) logP = 2.84[a] |
| 416 | — | $CH_2$ | O | 3-ethyl-tetrahydrofuran-3-yl | $C_2H_5$ | (2)Cl | (4)$CH_3SO_2$ | Z2 | (I-2) logP = 2.11[a] |
| 417 | — | $CH_2$ | O | 3-ethyl-tetrahydrofuran-3-yl | cyclopentyl | (2)Cl | (4)$CH_3SO_2$ | Z2 | (I-2) logP = 2.76[a] |
| 418 | — | $CH_2$ | O | $C_3H_7$-i | $C_2H_5$ | (2)Cl | (4)$CH_3SO_2$ | Z1 | (I-2) logP = 3.66[a] |
| 419 | — | $CH_2$ | O | $N,N$-dimethyl-isobutyramide | $CH_3$ | (2)Cl | (4)$CH_3SO_2$ | 4,4-dimethyl-2-methyl-cyclohexane-1,3-dione | (I-2) logP = 2.58[a] |
| 420 | — | $CH_2$ | O | $C_3H_7$-i | $C_3H_7$-i | (2)Cl | (4)$CH_3SO_2$ | Z1 | (I-2) logP = 3.99[a] |
| 421 | — | $CH_2$ | O | $C_3H_7$-i | $C_3H_7$-i | (2)Cl | (4)$CH_3SO_2$ | Z2 | (I-2) logP = 3.25[a] |
| 422 | — | $CH_2$ | O | H | cyclopentyl | (2)Cl | (4)$CH_3SO_2$ | Z2 | (I-2) logP = 2.31[a] |
| 423 | — | $CH_2$ | O | 3-ethyl-tetrahydrofuran-3-yl | $CH_3$ | (2)Cl | (4)$CH_3SO_2$ | Z2 | (I-2) logP = 1.97[a] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 424 | — | CH$_2$ | O | CH$_3$ | C$_2$H$_5$ | (2)Cl | (4)CH$_3$SO$_2$ | Z1 | (I-2) logP = 2.82[a) |
| 425 | — | CH$_2$ | O | CH$_3$ | C$_2$H$_5$ | (2)Cl | (4)CH$_3$SO$_2$ | 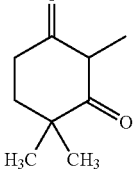 | (I-2) logP = 3.65[a) |
| 426 | — | CH$_2$ | O | 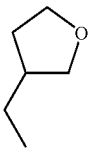 | 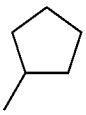 | (2)Cl | (4)CH$_3$SO$_2$ | Z1 | (I-2) logP = 3.53[a) |
| 427 | — | CH$_2$ | O | 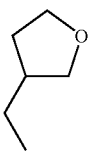 | C$_2$H$_5$ | (2)Cl | (4)CH$_3$SO$_2$ | Z4 | (I-2) logP = 1.90[a) |
| 428 | — | CH$_2$ | O | 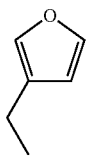 | CH$_3$ | (2)Cl | (4)CH$_3$SO$_2$ | Z1 | (I-2) logP = 3.10[a) |
| 429 | — | CH$_2$ | O | CH$_3$ | 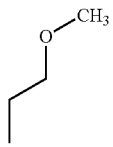 | (2)Cl | (4)CH$_3$SO$_2$ | Z1 | (I-2) logP = 2.43[a) |
| 430 | — | CH$_2$ | O | 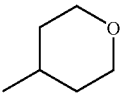 | CH$_3$ | (2)Cl | (4)CH$_3$SO$_2$ | Z1 | (I-2) logP = 2.51[a) |
| 431 | — | CH$_2$ | O | CH$_3$ | 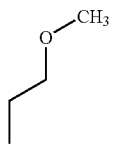 | (2)Cl | (4)CH$_3$SO$_2$ | Z2 | (I-2) logP = 1.80[a) |
| 432 | — | CH$_2$ | O | CH$_3$ | 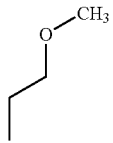 | (2)Cl | (4)CH$_3$SO$_2$ | 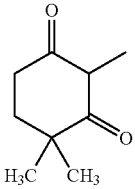 | (I-2) logP = 3.22[a) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 433 | — | $CH_2$ | O | $CH_3$ | propyl-O-$CH_3$ | (2)Cl | (4)$CH_3SO_2$ | Z4 | (I-2) logP = 1.51[a] |
| 434 | — | $CH_2$ | O | $CH_3$ | tetrahydrofuran-3-ylethyl | (2)Cl | (4)$CH_3SO_2$ | Z1 | (I-2) logP = 2.67[a] |
| 435 | — | $CH_2$ | O | $CH_3$ | tetrahydrofuran-3-ylethyl | (2)Cl | (4)$CH_3SO_2$ | Z2 | (I-2) logP = 2.03[a] |
| 436 | — | $CH_2$ | O | $CH_3$ | tetrahydrofuran-3-ylethyl | (2)Cl | (4)$CH_3SO_2$ | 4,4-dimethyl-2-methylcyclohexane-1,3-dione | (I-2) logP = 3.49[a] |
| 437 | — | $CH_2$ | O | $CH_3$ | tetrahydrofuran-3-ylethyl | (2)Cl | (4)$CH_3SO_2$ | Z4 | (I-2) logP = 1.73[a] |
| 438 | — | $CH_2$ | O | $CH_3$ | tetrahydropyran-2-ylethyl | (2)Cl | (4)$CH_3SO_2$ | Z1 | (I-2) logP = 3.04[a] |
| 439 | — | $CH_2$ | O | $CH_3$ | tetrahydropyran-2-ylethyl | (2)Cl | (4)$CH_3SO_2$ | Z2 | (I-2) logP = 2.35[a] |
| 440 | — | $CH_2$ | O | $CH_3$ | tetrahydropyran-2-ylethyl | (2)Cl | (4)$CH_3SO_2$ | Z4 | (I-2) logP = 2.01[a] |
| 441 | — | $CH_2$ | O | furan-3-yl | $CH_3$ | (2)Cl | (4)$CH_3SO_2$ | Z2 | (I-2) logP = 2.39[a] |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 442 | — | CH$_2$ | O | H | 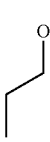 | (2)Cl | (4)CH$_3$SO$_2$ | Z1 | (I-2) logP = 3.07$^{a)}$ |
| 443 | — | CH$_2$ | O | CH$_3$ |  | (2)Cl | (4)CH$_3$SO$_2$ | Z2 | (I-2) logP = 2.41$^{a)}$ |
| 444 | — | CH$_2$ | O | CH$_3$ |  | (2)Cl | (4)CH$_3$SO$_2$ | Z1 | (I-2) logP = 3.14$^{a)}$ |
| 445 | — | CH$_2$ | O | CH$_3$ | 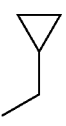 | (2)Cl | (4)CH$_3$SO$_2$ | Z2 | (I-2) logP = 2.05$^{a)}$ |
| 446 | — | CH$_2$ | O | 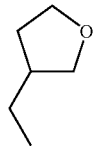 | C$_2$H$_5$ | (2)Cl | (4)CH$_3$SO$_2$ | 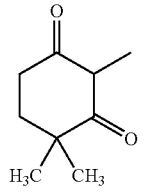 | (I-2) logP = 3.60$^{a)}$ |
| 447 | — | CH$_2$ | O | H | C$_2$H$_5$ | (2)OCH$_3$ | (4)Cl | Z1 | (I-2) logP = 2.20$^{a)}$ |
| 448 | — | CH$_2$ | O | H | C$_2$H$_5$ | (2)OCH$_3$ | (4)Cl | Z2 | (I-2) logP = 3.60$^{a)}$ |
| 449 | — | CH$_2$ | O | H | C$_2$H$_5$ | (2)Cl | (4)Cl | 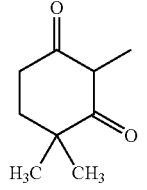 | (I-2) logP = 3.64$^{a)}$ |
| 450 | — | CH$_2$ | O | H | C$_2$H$_5$ | (2)Cl | (4)Cl | Z4 | (I-2) logP = 1.67$^{a)}$ |
| 451 | — | CH$_2$ | O | C$_2$H$_5$ | C$_2$H$_5$ | (2)Cl | (4)CH$_3$SO$_2$ | Z2 | (I-2) logP = 2.44$^{a)}$ |
| 452 | — | CH$_2$ | SO$_2$ | CH$_3$ | CH$_3$ | (2)Cl | (4)CH$_3$SO$_2$ | Z2 | (I-2) logP = 1.25$^{a)}$ |
| 453 | — | CH$_2$ | SO$_2$ | CH$_3$ | CH$_3$ | (2)Cl | (4)CH$_3$SO$_2$ | Z4 | (I-2) logP = 0.99$^{a)}$ |
| 454 | — | CH$_2$ | SO$_2$ | CH$_3$ | CH$_3$ | (2)Cl | (4)CH$_3$SO$_2$ | Z1 | (I-2) logP = 1.84$^{a)}$ |
| 455 | — | CH$_2$ | SO$_2$ | CH$_3$ | CH$_3$ | (2)Cl | (4)CH$_3$SO$_2$ | 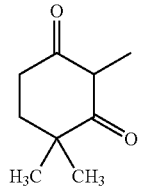 | (I-2) logP = 2.43$^{a)}$ |
| 456 | — | CH$_2$ | SO$_2$ | CH$_3$ | CH$_3$ | (2)Cl | (4)Cl | Z2 | (I-2) |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 457 | — | CH$_2$ | SO$_2$ | CH$_3$ | CH$_3$ | (2)Cl | (4)Cl | Z4 | (I-2) logP = 1.72$^{a)}$ |
| 458 | — | CH$_2$ | SO$_2$ | CH$_3$ | CH$_3$ | (2)Cl | (4)Cl | Z1 | (I-2) logP = 1.44$^{a)}$ |
| 459 | — | CH$_2$ | SO$_2$ | CH$_3$ | CH$_3$ | (2)Cl | (4)Cl | 2-methyl-6,6-dimethyl-cyclohexane-1,3-dione | (I-2) logP = 2.32$^{a)}$ |
| 460 | — | CH$_2$ | SO$_2$ | CH$_2$CH=CH$_2$ | CH$_3$ | (2)Cl | (4)CH$_3$SO$_2$ | Z1 | (I-2) logP = 3.01$^{a)}$ |
| 461 | — | CH$_2$ | SO$_2$ | CH$_2$CH=CH$_2$ | CH$_3$ | (2)Cl | (4)CH$_3$SO$_2$ | Z2 | (I-2) logP = 2.17$^{a)}$ |
| 462 | — | CH$_2$ | SO$_2$ | C$_2$H$_5$ | CH$_3$ | (2)OCH$_3$ | (4)Cl | Z2 | (I-2) logP = 1.63$^{a)}$ |
| 463 | — | CH$_2$ | SO$_2$ | C$_2$H$_5$ | CH$_3$ | (2)OCH$_3$ | (4)Cl | Z4 | (I-2) logP = 2.12$^{a)}$ |
| 464 | — | CH$_2$ | SO$_2$ | C$_2$H$_5$ | CH$_3$ | (2)OCH$_3$ | (4)Cl | Z1 | (I-2) logP = 1.80$^{a)}$ |
| 465 | — | CH$_2$ | SO$_2$ | C$_2$H$_5$ | CH$_3$ | (2)OCH$_3$ | (4)Cl | 2-methyl-6,6-dimethyl-cyclohexane-1,3-dione | (I-2) logP = 2.47$^{a)}$ |
| 466 | — | CH$_2$ | SO$_2$ | C$_2$H$_5$ | CH$_3$ | (2)Cl | (4)CH$_3$SO$_2$ | 2-methyl-6,6-dimethyl-cyclohexane-1,3-dione | (I-2) logP = 3.21$^{a)}$ |
| 467 | — | CH$_2$ | SO$_2$ | C$_2$H$_5$ | CH$_3$ | (2)Cl | (4)CH$_3$SO$_2$ | Z1 | (I-2) logP = 2.64$^{a)}$ |
| 468 | — | CH$_2$ | SO$_2$ | C$_2$H$_5$ | CH$_3$ | (2)Cl | (4)CH$_3$SO$_2$ | Z2 | (I-2) logP = 2.02$^{a)}$ |
| 469 | — | CH$_2$ | SO$_2$ | C$_2$H$_5$ | CH$_3$ | (2)Cl | (4)CH$_3$SO$_2$ | Z4 | (I-2) logP = 1.48$^{a)}$ |
| 470 | — | CH$_2$ | SO$_2$ | CH$_3$ | CH$_3$ | (2)OCH$_3$ | (4)Cl | Z2 | (I-2) logP = 1.22$^{a)}$ |
| 471 | — | CH$_2$ | SO$_2$ | CH$_3$ | CH$_3$ | (2)OCH$_3$ | (4)Cl | Z4 | (I-2) logP = 1.86$^{a)}$ |
| 472 | — | CH$_2$ | SO$_2$ | CH$_3$ | CH$_3$ | (2)OCH$_3$ | (4)Cl | Z1 | (I-2) logP = 1.55$^{a)}$ |
| 473 | — | CH$_2$ | SO$_2$ | CH$_3$ | CH$_3$ | (2)OCH$_3$ | (4)Cl | 2-methyl-6,6-dimethyl-cyclohexane-1,3-dione | (I-2) logP = 2.20$^{a)}$ |

TABLE 1-continued

Examples of compounds of the formula (I)

| Ex. No. | A¹ | A² | A³ | R¹ | R² | (position) X | (position) Y | data | Formula Physical |
|---|---|---|---|---|---|---|---|---|---|
| 474 | — | $CH_2$ | $SO_2$ | $C_2H_5$ | $CH_3$ | (2)$OCH_3$ | (4)Cl | 5-methylcyclohexane-1,3-dione (2-methyl substituted) | (I-2) logP = 2.81[a] |
| 475 | — | $CH_2$ | $SO_2$ | $C_2H_5$ | $CH_3$ | (2)Cl | (4)$CH_3SO_2$ | 5-methylcyclohexane-1,3-dione (2-methyl substituted) | (I-2) logP = 2.32[a] |
| 476 | — | $CH_2$ | $SO_2$ | $CH_3$ | $CH_3$ | (2)$OCH_3$ | (4)Cl | 5-methylcyclohexane-1,3-dione (2-methyl substituted) | (I-2) logP = 2.56[a] |
| 477 | — | $CH_2$ | O | $CH_3$ | $CH_3$ | (2)$OCH_3$ | (4)Cl | Z1 | (I-2) logP = 2.63[a] |
| 478 | — | $CH_2$ | O | $CH_3$ | $CH_3$ | (2)$OCH_3$ | (4)Cl | Z4 | (I-2) logP = 1.90[a] |
| 479 | — | $CH_2$ | O | $CH_3$ | $CH_3$ | (2)$OCH_3$ | (4)Cl | Z2 | (I-2) logP = 2.35[a] |
| 480 | — | $CH_2$ | O | $C_2H_5$ | $CH_3$ | (2)Cl | (4)Cl | Z4 | (I-2) logP = 2.46[a] |
| 481 | — | $CH_2$ | O | $C_2H_5$ | $CH_3$ | (2)Cl | (4)Cl | 4,4-dimethyl-2-methylcyclohexane-1,3-dione | (I-2) logP = 4.95[a] |
| 482 | — | $CH_2$ | O | $CH_3$ | $CH_3$ | (2)$OCH_3$ | (4)Cl | 5-methyl-2-methylcyclohexane-1,3-dione | (I-2) logP = 3.09[a] |
| 483 | — | $CH_2$ | O | $C_2H_5$ | $CH_3$ | (2)$OCH_3$ | (4)Cl | Z1 | (I-2) logP = 3.19[a] |
| 484 | — | $CH_2$ | O | $C_2H_5$ | $CH_3$ | (2)$OCH_3$ | (4)Cl | 4,4-dimethyl-2-methylcyclohexane-1,3-dione | (I-2) logP = 2.30[a] |
| 485 | — | $CH_2$ | O | $C_2H_5$ | $CH_3$ | (2)$OCH_3$ | (4)Cl | Z2 | (I-2) logP = 2.97[a] |
| 486 | — | $CH_2$ | O | $C_2H_5$ | $CH_3$ | (2)$OCH_3$ | (4)Cl | Z4 | (I-2) logP = 2.44[a] |
| 487 | — | $CH_2$ | $SO_2$ | $CH_3$ | $CH_3$ | (4)$CF_3$ | — | Z1 | (I-1) logP = 2.56[a] |
| 488 | — | $CH_2$ | $SO_2$ | $CH_3$ | $CH_3$ | (4)$CF_3$ | — | Z2 | (I-1) logP = 2.14[a] |

\* -$A^3$-$R^2$ together denote the radical listed in column $R^2$

The log P values given in the table were determined in accordance with EEC Directive 79/831 Annex V.A8 by HPLC (High Performance Liquid Chromatography) using a reversed-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—the corresponding measurement results are marked a) in Table 1.

(b) Mobile phases for the determination in the neutral range: 0.01 molar aqueous phosphate buffer solution, acetonitrile; linear gradient from 10% acetonitrile to 90% acetonitrile—the corresponding measurement results are marked b) in Table 1.

Calibration was carried out using unbranched alkan-2-ones (having 3 to 16 carbon atoms) with known log P values (determination of the log P values by the retention times using linear interpolation between two successive alkanones).

The lambda max values were determined in the maxima of the chromatographic signals using the UV spectra from 200 nm to 400 nm.

Starting Materials of the Formula (II)

Example (II-1)

Process g

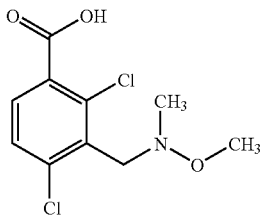

A mixture of 2.0 g (7.2 mmol) of methyl 2,4-dichloro-3-(N-methoxy-N-methylaminomethyl)benzoate, 0.32 g (7.9 mmol) of sodium hydroxide, 10 ml of water and 90 ml of tetrahydrofuran is stirred at room temperature (approximately 20° C.) for 4 hours and then concentrated under reduced pressure. The residue is shaken with water and ethyl acetate, the aqueous phase is separated off and the pH of the solution is adjusted to about 3.5 by addition of 1N hydrochloric acid. The mixture is then shaken with ethyl acetate and the organic phase is separated off, dried with sodium sulphate and filtered. The filtrate is concentrated under reduced pressure, the residue is digested with hexane and the resulting crystalline product is isolated by filtration with suction.

This gives 1.35 g (68% of theory, purity of product 95.9%) of 2,4-dichloro-3-(N-methoxy-N-methylaminomethyl)benzoic acid. log P=1.99.

Example (II-2)

Process g

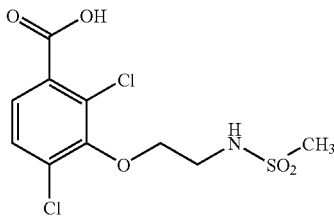

A mixture of 0.85 g (2.4 mmol) of ethyl 2,4-dichloro-3-(2-methylsulphonylaminoethoxy)benzoate, 10 ml of ethanol and 1.5 g of 10% strength aqueous sodium hydroxide solution is stirred at room temperature (approximately 20° C.) for 3 hours and then digested with 60 ml of diethyl ether. The aqueous phase is separated off and the organic phase is shaken with 10 ml of water. The combined aqueous phases are acidified with conc. hydrochloric acid and then extracted twice with in each case 30 ml of methylene chloride. The combined organic extracts are dried with sodium sulphate and filtered. From the filtrate, the solvent is carefully distilled off under reduced pressure.

This gives 0.56 g (69% of theory, purity of the product 96%) of 2,4-dichloro-3-(2-methylsulphonylaminoethoxy)benzoic acid. log P=1.36

Example II-3

Process g

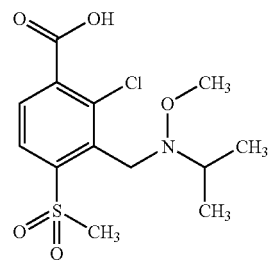

1.90 g (5.4 mmol) of methyl 2-chloro-4-methylsulphonyl-3-(N-methoxy-N-(1-methylethyl)aminomethyl)benzoate are initially charged in 20 ml of tetrahydrofuran. At room temperature (approximately 20° C.) a solution of 0.22 g (5.4 mmol) of sodium hydroxide in 20 ml of water is added dropwise. The reaction mixture is stirred at room temperature for 16 hours. The tetrahydrofuran is then removed under reduced pressure and the aqueous solution is washed with diethyl ether. The aqueous phase is then acidified with hydrochloric acid and extracted repeatedly with ethyl acetate. The combined ethyl acetate phases are dried over sodium sulphate and concentrated under reduced pressure.

This gives 1.50 g (82% of theory, purity of the product 87% according to HPLC) of 2-chloro-4-methylsulphonyl-3-(N-methoxy-N-(1-methyl ethyl) aminomethyl)benzoic acid as a light-yellow solid. log P=2.09 (acidic)

Analogously to Examples (II-1) and (II-2), it is also possible, for example, to prepare the compounds of the formula (II) listed in Table 2 below.

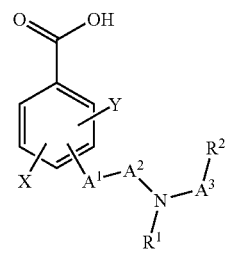

(II)

TABLE 2
Examples of the compounds of the formula II
| Ex. No. | (position-) ⟋A¹⟍A²⟋N⟍A³⟋R² \| R¹ | (position-) X | (position-) Y | Physical data |
|---|---|---|---|---|
| II-4 | 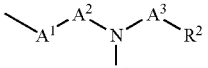 (3) | (2) Cl | (4) Cl | logP = 1.58 [a)] |
| II-5 | 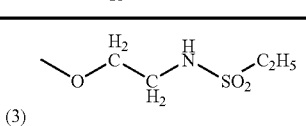 (3) | (2) Cl | (4) Cl | |
| II-6 | 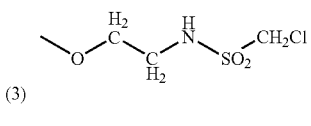 (3) | (2) Cl | (4) Cl | logP = 2.43 [a)] |
| II-7 | 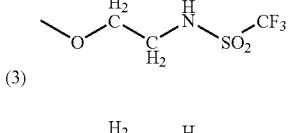 (3) | (2) Cl | (4) SO$_2$CH$_3$ | logP = 0.81 [a)] |
| II-8 | 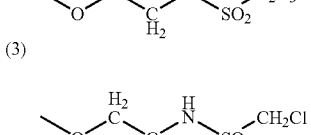 (3) | (2) Cl | (4) SO$_2$CH$_3$ | |
| II-9 | 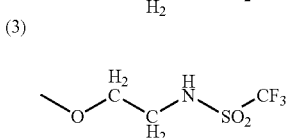 (3) | (2) Cl | (4) SO$_2$CH$_3$ | |
| II-10 | 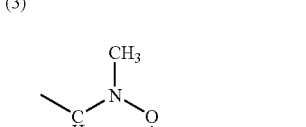 (3) | (2) Cl | (4) SO$_2$CH$_3$ | |
| II-11 | 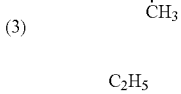 (3) | (2) Cl | (4) Cl | logP = 2.51 |
| II-12 | 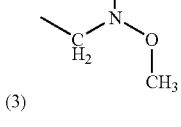 (3) | (2) Cl | (4) SO$_2$CH$_3$ | |
| II-13 | 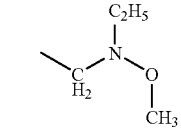 (3) | (2) Cl | (4) Cl | logP = 2.51 |

TABLE 2-continued

Examples of the compounds of the formula II

| Ex. No. | (position-) $A^1-A^2-N(R^1)-A^3-R^2$ | (position-) X | (position-) Y | Physical data |
|---|---|---|---|---|
| II-14 | (3) -CH$_2$-N(C$_2$H$_5$)-O-C$_2$H$_5$ | (2) Cl | (4) SO$_2$CH$_3$ | logP = 2.04 |
| II-15 | (3) -CH$_2$-N(CH$_3$)-O-C$_2$H$_5$ | (2) Cl | (4) Cl | |
| II-16 | (3) -CH$_2$-N(CH$_3$)-O-C$_2$H$_5$ | (2) Cl | (4) SO$_2$CH$_3$ | |
| II-17 | (3) -CH$_2$-N(CH$_2$C$_6$H$_5$)-O-CH$_3$ | (2) Cl | (4) Cl | |
| II-18 | (3) -CH$_2$-N(CH$_2$C$_6$H$_5$)-O-CH$_3$ | (2) Cl | (4) SO$_2$CH$_3$ | |
| II-19 | (3) -CH$_2$-N(CH$_2$CH$_2$F)-O-CH$_3$ | (2) Cl | (4) Cl | |
| II-20 | (3) -CH$_2$-N(CH$_2$CH$_2$F)-O-CH$_3$ | (2) Cl | (4) SO$_2$CH$_3$ | |

TABLE 2-continued

Examples of the compounds of the formula II

| Ex. No. | (position-) R¹ on A¹–A²–N(–A³–R²) | (position-) X | (position-) Y | Physical data |
|---|---|---|---|---|
| II-21 | (3) N(CH₂CH=CH₂)(CH₂CH₃)(OCH₃) | (2) Cl | (4) Cl | |
| II-22 | (3) N(CH₂CH=CH₂)(CH₂CH₃)(OCH₃) | (2) Cl | (4) SO₂CH₃ | |
| II-23 | (3) N(CH₂C≡CH)(CH₂CH₃)(OCH₃) | (2) Cl | (4) Cl | |
| II-24 | (3) N(CH₂C≡CH)(CH₂CH₃)(OCH₃) | (2) Cl | (4) SO₂CH₃ | |
| II-25 | (3) CH₃O-CH₂-CH₂-N(SO₂-n-C₃H₇) | (2) Cl | (4) Cl | logP = 1.86 [a] |
| II-26 | (3) CH₃O-CH₂-CH₂-N(SO₂-n-C₃H₇) | (2) Cl | (4) SO₂CH₃ | |
| II-27 | (3) CH₃O-CH₂-CH₂-N(SO₂-2-thienyl) | (2) Cl | (4) Cl | logP = 2.13 [a] |
| II-28 | (3) CH₃O-CH₂-CH₂-N(SO₂-2-thienyl) | (2) Cl | (4) SO₂CH₃ | |

TABLE 2-continued

Examples of the compounds of the formula II $$\diagdown_{A^1}\diagup^{A^2}\diagdown_N\diagup^{A^3}\diagdown_{R^2}$$
         |
         R¹
(position-)

| Ex. No. | R¹ (position-) | X (position-) | Y (position-) | Physical data |
|---|---|---|---|---|
| II-29 | ethyl-NH-imidazolidinone (3) | (2) Cl | (4) Cl | Fp.: 223° C. |
| II-30 | CH₃O-CH₂-CH₂-N(H)-SO₂-C₃H₇-i (3) | (2) Cl | (4) Cl | logP = 1.50 [a] |
| II-31 | CH₃O-CH₂-CH₂-N(H)-SO₂-C₃H₇-i (3) | (2) Cl | (4) SO₂CH₃ | |
| II-32 | ethyl-NH-imidazolidinone (3) | (2) Cl | (4) SO₂CH₃ | Fp.: 243° C. |
| II-33 | -CH₂-N(H)-O-CH₃ (3) | (2) Cl | (4) Cl | logP = 1.38 |
| II-34 | -CH₂-N(H)-O-CH₂CH₃ (3) | (2) Cl | (4) Cl | logP = 1.76 |
| II-35 | -CH₂-N(CH₃)-O-CH₃ (3) | (2) Cl | (4) Cl | logP = 1.99 |
| II-36 | -CH₂-N(H)-O-CH₂CH₃ (3) | (2) Cl | (4) SO₂Me | logP = 0.98 |
| II-37 | -CH₂-N(H)-O-CH₂CH₃ (3) | (2) OCH₃ | (4) Cl | logP = 1.44 |
| II-38 | CH₃CH₂-N(H)-O-CH₃ (3) | (2) Cl | (4) SO₂Me | logP$_{acidic}$ = 0.58 |

TABLE 2-continued

Examples of the compounds of the formula II

| Ex. No. | (position-) R¹ on A¹-A²-N(R¹)-A³-R² | (position-) X | (position-) Y | Physical data |
|---|---|---|---|---|
| II-39 | (3) Et-N(CH₃)-O-CH₃ | (2) Cl | (4) SO₂Me | $\log P_{acidic} = 1.77$ |
| II-40 | (3) Et-N(CH₂CH₃)-O-CH₃ | (2) Cl | (4) SO₂Me | $\log P_{acidic} = 1.77$ |
| II-41 | (3) Et-N(CH₂Ph)-O-CH₃ | (2) Cl | (4) SO₂Me | $\log P_{acidic} = 2.43$ |
| II-42 | (3) Et-N(CH(CH₃)₂)-O-CH₃ | (2) Cl | (4) SO₂Me | $\log P_{acidic} = 2.09$ |
| II-43 | (3) Et-NH-O-CH₂Ph | (2) Cl | (4) SO₂Me | $\log P_{acidic} = 1.99$ |
| II-44 | (3) MeO-CH₂-CH₂-NH-SO₂-CH₃ | (2) CH₃ | (4) Cl | $\log P_{acidic} = 1.82$ |
| II-45 | (3) MeO-CH₂-CH₂-NH-SO₂-C₂H₅ | (2) CH₃ | (4) Cl | $\log P_{acidic} = 1.69$ |
| II-46 | (3) MeO-CH₂-CH₂-NH-SO₂-CH₃ | (2) CH₃ | (4) Br | $\log P_{acidic} = 1.56$ |
| II-47 | (3) MeO-CH₂-CH₂-NH-SO₂-C₂H₅ | (2) CH₃ | (4) Br | $\log P_{acidic} = 1.76$ |
| II-48 | (3) MeO-CH₂-CH₂-NH-SO₂-CH₃ | (2) Cl | (4) SO₂Me | $\log P_{acidic} = 0.74$ |

TABLE 2-continued

Examples of the compounds of the formula II

| Ex. No. | (position-) R¹ on A¹-A²-N-A³-R² structure | (position-) X | (position-) Y | Physical data |
|---|---|---|---|---|
| II-49 | (3) -CH₂-O-CH₂-CH₂-NH-SO₂-CH₃ | (2) Br | (4) Br | $logP_{acidic} = 1.43$ |
| II-50 | (3) -CH₂-N(CH₃)-O-CH₂-cyclopropyl | (2) Cl | (4) SO₂Me | $logP_{acidic} = 2.00$ |
| II-51 | (3) -CH₂-N(OCH₃)-CH₂-cyclopropyl with ethyl | (2) Cl | (4) SO₂Me | $logP_{acidic} = 2.18$ |
| II-52 | (3) -N(ethyl)(OCH₃)-CH₂-CH=CH₂ | (2) Cl | (4) SO₂Me | $logP_{acidic} = 1.91$ |
| II-53 | (3) -N(ethyl)(OCH₃)-CH₂-C(=O)-N(C₂H₅)₂ | (2) Cl | (4) SO₂Me | $logP_{acidic} = 1.51$ |
| II-54 | (3) -N(ethyl)(OCH₃)-CH(CH₃)-cyclopropyl | (2) Cl | (4) SO₂Me | $logP_{acidic} = 2.50$ |
| II-55 | (3) -N(ethyl)(OCH₃)-cyclopentyl | (2) Cl | (4) SO₂Me | $logP_{acidic} = 2.53$ |
| II-56 | (3) -N(ethyl)(OCH₃)-C(=O)-CH₃ | (2) Cl | (4) SO₂Me | $logP_{acidic} = 0.72$ |

TABLE 2-continued

Examples of the compounds of the formula II (position-) $\diagdown_{A^1}\diagup^{A^2}\diagdown_{N}\diagup^{A^3}\diagdown_{R^2}$ | | |
| --- | --- | --- |
| Ex. No. | $R^1$ | (position-) X | (position-) Y | Physical data |
| II-57 | [N-ethyl-N-methoxy-4-yl-tetrahydrothiopyran] (3) | (2) Cl | (4) SO$_2$Me | logP$_{acidic}$ = 2.20 |
| II-58 | [N-ethyl-N-methoxy-CH$_2$-pyridin-2-yl] (3) | (2) Cl | (4) SO$_2$Me | logP$_{acidic}$ = 0.34 |
| II-59 | [N-ethyl-N-methoxy-CH$_2$-pyridin-3-yl] (3) | (2) Cl | (4) SO$_2$Me | logP$_{acidic}$ = 0.36 |
| II-60 | [N-ethyl-N-ethoxy-CH$_3$] (3) | (2) Cl | (4) SO$_2$Me | logP$_{acidic}$ = 1.66 |
| II-61 | [N-ethyl-N-ethoxy-CH(CH$_3$)$_2$] (3) | (2) Cl | (4) SO$_2$Me | logP$_{acidic}$ = 2.41 |
| II-62 | [N-methyl-N-isopropoxy-ethyl] (3) | (2) Cl | (4) SO$_2$Me | logP$_{acidic}$ = 1.96 |
| II-63 | [N-ethyl-N-isopropoxy-ethyl] (3) | (2) Cl | (4) SO$_2$Me | logP$_{acidic}$ = 2.30 |
| II-64 | [N-ethyl-N-isopropoxy-isopropyl] (3) | (2) Cl | (4) SO$_2$Me | logP$_{acidic}$ = 2.71 |

TABLE 2-continued

Examples of the compounds of the formula II

| Ex. No. | (position-) R¹ on A¹-A²-N(R¹)-A³-R² | (position-) X | (position-) Y | Physical data |
|---|---|---|---|---|
| II-65 | (3) ethyl-NH-O-cyclopentyl | (2) Cl | (4) SO$_2$Me | logP$_{acidic}$ = 1.88 |
| II-66 | (3) ethyl-N(CH$_3$)-O-cyclopentyl | (2) Cl | (4) SO$_2$Me | logP$_{acidic}$ = 2.36 |
| II-67 | (3) ethyl-N(OCH$_3$)-C(O)-cyclopropyl | (2) Cl | (4) SO$_2$Me | logP$_{acidic}$ = 1.25 |
| II-68 | (3) ethyl-N(OCH$_3$)-CH$_2$-C(O)-N(CH$_3$)$_2$ | (2) Cl | (4) SO$_2$Me | logP$_{acidic}$ = 0.99 |
| II-69 | (3) ethyl-N(OCH$_3$)-CH$_2$-(tetrahydrofuran-3-yl) | (2) Cl | (4) SO$_2$Me | logP$_{acidic}$ = 1.52 |
| II-70 | (3) ethyl-N(OC$_2$H$_5$)-CH$_2$-(tetrahydrofuran-3-yl) | (2) Cl | (4) SO$_2$Me | logP$_{acidic}$ = 1.71 |
| II-71 | (3) ethyl-N(O-cyclopentyl)-CH$_2$-(tetrahydrofuran-3-yl) | (2) Cl | (4) SO$_2$Me | logP$_{acidic}$ = 2.28 |
| II-72 | (3) ethyl-N(OCH$_3$)-CH$_2$-(furan-3-yl) | (2) Cl | (4) SO$_2$Me | logP$_{acidic}$ = 2.04 |

TABLE 2-continued

Examples of the compounds of the formula II

| Ex. No. | (position-) R¹ on A¹-A²-N(R¹)-A³-R² | (position-) X | (position-) Y | Physical data |
|---|---|---|---|---|
| II-73 | (3) ethyl-N(OCH₃)-tetrahydrofuran-3-yl | (2) Cl | (4) SO₂Me | $\log P_{acidic} = 1.33$ |
| II-74 | (3) ethyl-N(OCH₃)-tetrahydropyran-3-yl | (2) Cl | (4) SO₂Me | $\log P_{acidic} = 1.64$ |
| II-75 | (3) ethyl-N(OCH₃)-tetrahydropyran-4-yl | (2) Cl | (4) SO2Me | $\log P_{acidic} = 1.49$ |
| II-76 | (3) ethyl-N(CH₃)-O-CH₂CH₂-O-CH₃ | (2) Cl | (4) SO2Me | $\log P_{acidic} = 1.40$ |
| II-77 | (3) ethyl-N(H)-O-CH₂CH₂-O-C₆H₅ | (2) Cl | (4) SO2Me | $\log P_{acidic} = 2.09$ |
| II-78 | (3) ethyl-N(CH₃)-O-CH₂CH₂-O-C₆H₅ | (2) Cl | (4) SO2Me | $\log P_{acidic} = 2.43$ |
| II-79 | (3) ethyl-N(CH₃)-O-CH₂-(tetrahydrofuran-2-yl) | (2) Cl | (4) SO2Me | $\log P_{acidic} = 1.63$ |
| II-80 | (3) ethyl-N(CH₃)-O-CH₂-(tetrahydropyran-2-yl) | (2) Cl | (4) SO2Me | $\log P_{acidic} = 1.91$ |
| II-81 | (3) ethyl-N(H)-O-CH₃ | (2) Cl | (4) Cl | $\log P_{acidic} = 1.38$ |

TABLE 2-continued

Examples of the compounds of the formula II (position-)

```
    \A¹—A²    A³
         \N/   \R²
          |
          R¹
```

| Ex. No. | R¹ structure | (position-) X | (position-) Y | Physical data |
|---|---|---|---|---|
| II-82 | N(CH₃)(CH₂-)OCH₃ at (3) | (2) OCH₃ | (4) Cl | logP$_{acidic}$ = 1.81 |
| II-83 | N(C₂H₅)(CH₂-)OCH₃ at (3) | (2) OCH₃ | (4) Cl | logP$_{acidic}$ = 2.29 |
| II-84 | N(SO₂CH₃)(CH₃)(CH₂-) at (3) | (2) Cl | (4) Cl | logP$_{acidic}$ = 1.45 |
| II-85 | N(SO₂CH₃)(CH₃)(CH₂-) at (3) | (2) Cl | (4) SO2Me | logP$_{acidic}$ = 0.77 |
| II-86 | N(SO₂CH₃)(C₂H₅)(CH₂-) at (3) | (2) OCH₃ | (4) Cl | logP$_{acidic}$ = 1.73 |
| II-87 | N(SO₂CH₃)(CH₂CH=CH₂)(CH₂-) at (3) | (2) Cl | (4) SO2Me | logP$_{acidic}$ = 1.28 |
| II-88 | N(SO₂CH₃)(C₂H₅)(CH₂-) at (3) | (2) Cl | (4) SO2Me | logP$_{acidic}$ = 1.10 |
| II-89 | N(SO₂CH₃)(CH₃)(CH₂-) at (3) | (2) OCH₃ | (4) Cl | logP$_{acidic}$ = 1.49 |

Starting Materials of the Formula (VIII)

Example (VIII-1)

Process h

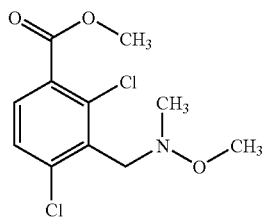

A mixture of 14.9 g (50 mmol) of methyl 3-bromomethyl-2,4-dichlorobenzoate, 3.05 g (50 mmol) of N,O-dimethylhydroxylamine, 2.0 g (50 mmol) of sodium hydride (60% in mineral oil) and 100 ml of acetonitrile is stirred at room temperature (approximately 20° C.) for 18 hours, 200 ml of water are added carefully and the mixture is then diluted with methylene chloride to about double its original volume. After shaking, the organic phase is separated off, washed with water, dried with sodium sulphate and filtered. The filtrate is concentrated under reduced pressure and the residue is purified by column chromatography (silica gel, hexane/ethyl acetate, vol.: 1:1).

This gives 2.1 g (14% of theory, purity of product 91.2%) of methyl 2,4-dichloro-3-(N-methoxy-N-methylaminomethyl)benzoate. log P=3.08.

Example (VIII-2)

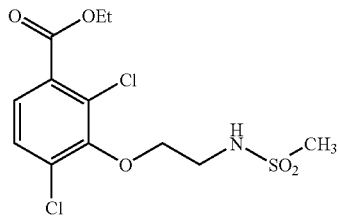

Step 1

A mixture of 4.8 g (20.4 mmol) of ethyl 2,4-dichloro-3-hydroxybenzoate, 11.6 g (36.8 mmol) of O-t-butyl N-[2-[(4-methylphenyl)sulphonyloxy]ethyl]carbamate, 5.6 g (40 mmol) of potassium carbonate and 140 ml of acetonitrile is stirred at 75° C. for 15 hours. At room temperature, 200 ml of water are then added, and the mixture is shaken twice with methylene chloride. The combined organic phases are dried with sodium sulphate and filtered. From the filtrate, the volatile components are carefully distilled off under reduced pressure.

This gives 8.0 g (84% of theory, purity of the product 81%) of ethyl 2,4-dichloro-3-[2-[(t-butoxycarbonyl)amino]ethoxy]benzoate. log P=3.79

Step 2

At room temperature (approximately 20° C.), 52 g (455 mmol) of trifluoroacetic acid are added dropwise with stirring to 12.3 g (32.5 mmol) of ethyl 2,4-dichloro-3-[2-[(t-butoxycarbonyl)amino]ethoxy]benzoate. The mixture is stirred at room temperature for 15 minutes and then poured into 200 ml of ice-water. The mixture is then extracted twice with in each case 150 ml of methylene chloride and the combined organic phases are dried with sodium sulphate and filtered. The filtrate is concentrated under reduced pressure, the residue is digested with petroleum ether/diethyl ether and the resulting crystalline product is isolated by filtration with suction.

This gives 7.3 g (79% of theory, purity of the product 98%) of ethyl 3-(2-aminoethoxy)-2,4-dichlorobenzoate. log P=1.08

Step 3 (Process i)

2.0 g (7.2 mmol) of ethyl 3-(2-aminoethoxy)-2,4-dichlorobenzoate are dissolved in 24 ml of tetrahydrofuran, and 0.29 g (7.2 mmol) of sodium hydride (60%) is added. The mixture is stirred at room temperature (approximately 20° C.) for 60 minutes, 0.82 g (7.2 mmol) of methanesulphonyl chloride is then added and the mixture is stirred at room temperature for another 30 minutes. 50 ml of water are then added, and the mixture is extracted twice with in each case, 50 ml of ethyl acetate. The combined organic phases are dried using sodium sulphate and filtered. From the filtrate, the solvent is carefully distilled off under reduced pressure.

This gives 0.75 g (25% of theory, purity of the product 86%) of ethyl 2,4-dichloro-3-(2-methylsulphonylaminoethoxy)benzoate. log P=2.35

Example (VIII-3)

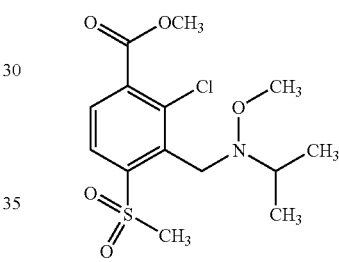

Step 1

At room temperature, 55.20 g (0.40 mol) of potassium carbonate are added to a solution of 33.41 g (0.40 mol) of O-methylhydroxylamine hydrochloride in 100 ml of acetonitrile. The mixture is stirred at room temperature for 30 minutes, and a solution of 68.32 g (0.20 mol) of methyl 3-bromomethyl-2-chloro-4-methylsulphonylbenzoate in 100 ml of acetonitrile is then added, and the mixture is stirred at room temperature for another 18 hours. For work-up, the solvent is removed from the reaction mixture using a rotary evaporator and the residue is partitioned between water and dichloromethane. The organic phase is separated off, dried over sodium sulphate and concentrated under reduced pressure. The residue is triturated with diethyl ether and filtered. This gives 36.6 g (55% of theory, purity of the product 92% according to LC/MS) of methyl 2-chloro-4-methylsulphonyl-3-(N-methoxyaminomethyl)-benzoate as a solid residue.

Step 2 (Process k)

At room temperature, 4.00 g (13.0 mmol) of methyl 2-chloro-4-methylsulphonyl-3-(N-methoxyaminomethyl)benzoate, 0.76 g (13.0 mmol) of acetone and 3.27 g (13.0 mmol) of pyridinium p-toluenesulphonate are initially charged in a mixture of 50 ml of methanol and 15 ml of tetrahydrofuran under an atmosphere of protective gas. At room temperature, 1.3 ml (1.21 g, 13.0 mmol) of pyridine/borane complex are added dropwise from a syringe, and the mixture is stirred at room temperature for another 16 hours.

For work-up, ethyl acetate is added to the reaction mixture, which is then washed successively with 2 N aqueous hydrochloric acid solution and saturated aqueous sodium bicarbonate solution and saturated aqueous sodium chloride solution. The organic phase is then dried over sodium sulphate and concentrated under reduced pressure. This gives 3.10 g (68% of theory, purity of the product 90% according to HPLC) of methyl 2-chloro-4-methylsulphonyl-3 N-methoxy-N-(1-methylethyl)aminomethyl)benzoate as a yellow, highly viscous oil. log P=3.13 (acidic)

Analogously to Examples (VIII-1)-(VIII-3), it is also possible to prepare, for example, the compounds of the formula (VIII) listed in Table 3 below

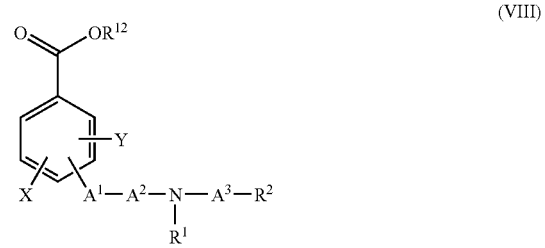

(VIII)

TABLE 3

Examples of the compounds of the formula (VIII)

| Ex. No. | (structure with $A^1, A^2, N, A^3, R^2, R^1$) | $R^{12}$ | (position) X | (position) Y | Physical data |
|---|---|---|---|---|---|
| VIII-4 | CH₂—NH—(imidazolidinone) (3) | CH₃ | (2) Cl | (4) Cl | M.p.: 164° C. |
| VIII-5 | CH₂—NH—(imidazolidinone) (3) | CH₃ | (2) Cl | (4) SO₂CH₃ | logP = 1.24 |
| VIII-6 | —CH(H)—N(H)—O—CH₃ (3) | CH₃ | (2) Cl | (4) Cl | logP = 2.26 |
| VIII-7 | —CH(H)—N(H)—O—CH₂CH₃ (3) | CH₃ | (2) Cl | (4) Cl | logP = 2.77 |
| VIII-8 | —CH(H)—N(CH₃)—O—CH₃ (3) | CH₃ | (2) Cl | (4) Cl | logP = 3.08 |
| VIII-9 | —CH(H)—N(CH₂CH₃)—O—CH₃ (3) | CH₃ | (2) Cl | (4) Cl | logP = 3.72 |
| VIII-10 | —CH(H)—N(H)—O—CH₃ (3) | CH₃ | (2) Cl | (4) SO₂Me | logP = 1.69 |

TABLE 3-continued
Examples of the compounds of the formula (VIII)
| Ex. No. | (position) A¹\A²\N—A³—R² / R¹ | R¹² | (position) X | (position) Y | Physical data |
|---|---|---|---|---|---|
| VIII-11 | 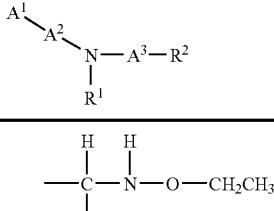 (3) | $CH_3$ | (2) Cl | (4) $SO_2Me$ | logP = 2.05 |
| VIII-12 | 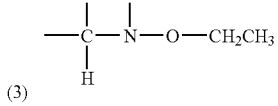 (3) | $CH_3$ | (2) Cl | (4) $SO_2Me$ | logP = 3.06 |
| VIII-13 | 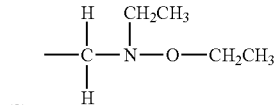 (3) | $CH_3$ | (2) OMe | (4) Cl | logP = 2.27 |
| VIII-14 | 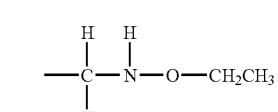 (3) | $C_2H_5$ | (2) Cl | (4) Cl | logP = 2.24 |
| VIII-15 | 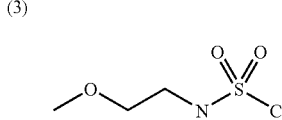 (3) | $C_2H_5$ | (2) Cl | (4) Cl | logP = 2.61 |
| VIII-16 |  (3) | $C_2H_5$ | (2) Cl | (4) Cl | logP = 2.80 |
| VIII-17 | 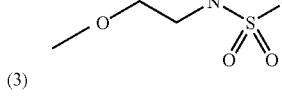 (3) | $C_2H_5$ | (2) Cl | (4) Cl | logP = 3.08 |
| VIII-18 | 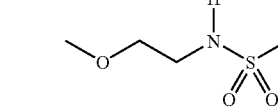 (3) | $C_2H_5$ | (2) Cl | (4) Cl | logP = 3.20 |
| VIII-19 | 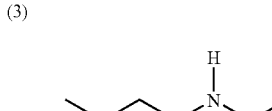 (3) | $C_2H_5$ | (2) Cl | (4) Cl | logP = 2.92 |

TABLE 3-continued

Examples of the compounds of the formula (VIII)

| Ex. No. | R¹ (position) | R¹² | X (position) | Y (position) | Physical data |
|---|---|---|---|---|---|
| VIII-20 | 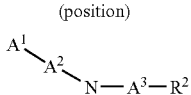 (3) | $C_2H_5$ | (2) Cl | (4) Cl | logP = 2.86 |
| VIII-21 | 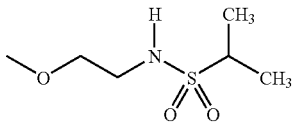 (3) | $CH_3$ | (2) Cl | (4) $SO_2Me$ | $logP_{acidic}$ = 1.69 |
| VIII-22 | 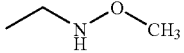 (3) | $CH_3$ | (2) Cl | (4) $SO_2Me$ | $logP_{acidic}$ = 2.31 |
| VIII-23 | 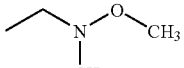 (3) | $CH_3$ | (2) Cl | (4) $SO_2Me$ | $logP_{acidic}$ = 2.74 |
| VIII-24 | 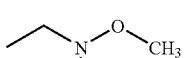 (3) | $CH_3$ | (2) Cl | (4) $SO_2Me$ | $logP_{acidic}$ = 3.42 |
| VIII-25 |  (3) | $CH_3$ | (2) Cl | (4) $SO_2Me$ | $logP_{acidic}$ = 3.13 |
| VIII-26 | 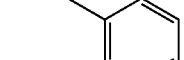 (3) | $CH_3$ | (2) $CH_3$ | (4) Cl | $logP_{acidic}$ = 2.14 |
| VIII-27 | 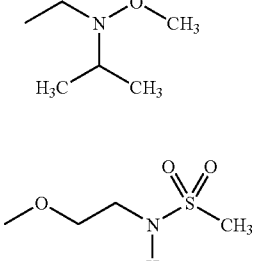 (3) | $CH_3$ | (2) $CH_3$ | (4) Cl | $logP_{acidic}$ = 2.37 |
| VIII-28 | 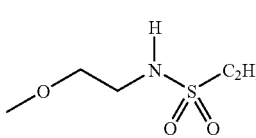 (3) | $CH_3$ | (2) $CH_3$ | (4) Br | $logP_{acidic}$ = 2.20 |

TABLE 3-continued

Examples of the compounds of the formula (VIII)

| Ex. No. | (position) A¹−A²−N−A³−R² \| R¹ | R¹² | (position) X | (position) Y | Physical data |
|---|---|---|---|---|---|
| VIII-29 | (3) methoxyethyl-N(H)-SO₂-C₂H₅ | CH₃ | (2) CH₃ | (4) Br | logP$_{acidic}$ = 2.46 |
| VIII-30 | (3) methoxyethyl-N(H)-SO₂-CH₃ | CH₃ | (2) Cl | (4) SO₂Me | logP$_{acidic}$ = 1.56 |
| VIII-31 | (3) methoxyethyl-N(H)-SO₂-C₂H₅ | CH₃ | (2) Cl | (4) SO₂Me | logP$_{acidic}$ = 1.75 |
| VIII-32 | (3) methoxyethyl-N(H)-SO₂-CH₃ | CH₃ | (2) Br | (4) Br | logP$_{acidic}$ = 2.13 |
| VIII-33 | (3) CH(H)(H)-N(CH₃)-O-CH₂-cyclopropyl | CH₃ | (2) Cl | (4) SO₂Me | logP$_{acidic}$ = 2.98 |
| VIII-34 | (3) ethyl-N(O-CH₃)-CH₂-cyclopropyl | CH₃ | (2) Cl | (4) SO₂Me | logP$_{acidic}$ = 3.18 |
| VIII-35 | (3) ethyl-N(O-CH₃)-CH₂-CH=CH₂ | CH₃ | (2) Cl | (4) SO₂Me | logP$_{acidic}$ = 2.87 |
| VIII-36 | (3) ethyl-N(O-CH₃)-CH₂-C(=O)-N(C₂H₅)₂ | CH₃ | (2) Cl | (4) SO₂Me | logP$_{acidic}$ = 2.28 |

TABLE 3-continued

Examples of the compounds of the formula (VIII)

| Ex. No. | R¹ (position on A¹A²N–A³–R²) | R¹² | X (position) | Y (position) | Physical data |
|---|---|---|---|---|---|
| VIII-37 | N-ethyl, N-methoxy, 1-cyclopropylethyl (3) | $CH_3$ | (2) Cl | (4) $SO_2Me$ | $logP_{acidic} = 3.58$ |
| VIII-38 | N-ethyl, N-methoxy, cyclopentyl (3) | $CH_3$ | (2) Cl | (4) $SO_2Me$ | $logP_{acidic} = 3.67$ |
| VIII-39 | N-ethyl, N-methoxy, acetyl (3) | $CH_3$ | (2) Cl | (4) $SO_2Me$ | $logP_{acidic} = 1.58$ |
| VIII-40 | N-ethyl, N-methoxy, tetrahydrothiopyran-4-yl (3) | $CH_3$ | (2) Cl | (4) $SO_2Me$ | $logP_{acidic} = 3.20$ |
| VIII-41 | N-ethyl, N-methoxy, (pyridin-2-yl)methyl (3) | $CH_3$ | (2) Cl | (4) $SO_2Me$ | $logP_{acidic} = 1.17$ |
| VIII-42 | N-ethyl, N-methoxy, (pyridin-3-yl)methyl (3) | $CH_3$ | (2) Cl | (4) $SO_2Me$ | $logP_{acidic} = 1.16$ |
| VIII-43 | N-ethyl, N-ethoxy, methyl (3) | $CH_3$ | (2) Cl | (4) $SO_2Me$ | $logP_{acidic} = 2.64$ |
| VIII-44 | N-ethyl, N-ethoxy, isopropyl (3) | $CH_3$ | (2) Cl | (4) $SO_2Me$ | $logP_{acidic} = 3.52$ |

TABLE 3-continued

Examples of the compounds of the formula (VIII)

| Ex. No. | R¹ (position) | R¹² | X (position) | Y (position) | Physical data |
|---|---|---|---|---|---|
| VIII-45 | 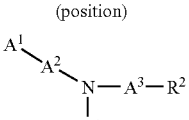 (3) | CH₃ | (2) Cl | (4) SO₂Me | logP$_{acicic}$ = 2.97 |
| VIII-46 | 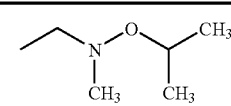 (3) | CH₃ | (2) Cl | (4) SO₂Me | logP$_{acidic}$ = 3.39 |
| VIII-47 | 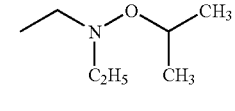 (3) | CH₃ | (2) Cl | (4) SO₂Me | logP$_{acidic}$ = 3.86 |
| VIII-48 | 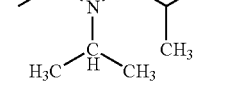 (3) | CH₃ | (2) Cl | (4) SO₂Me | logP$_{acidic}$ = 2.93 |
| VIII-49 | 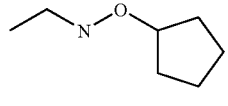 (3) | CH₃ | (2) Cl | (4) SO₂Me | logP$_{acidic}$ = 3.48 |
| VIII-50 | 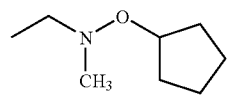 (3) | CH₃ | (2) Cl | (4) SO₂Me | logP$_{acidic}$ = 2.60 |
| VIII-51 | 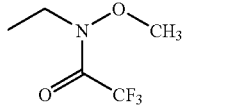 (3) | CH₃ | (2) Cl | (4) SO₂Me | logP$_{acidic}$ = 2.21 |
| VIII-52 | 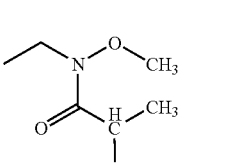 (3) | CH₃ | (2) Cl | (4) SO₂Me | logP$_{acidic}$ = 2.02 |
| VIII-53 | 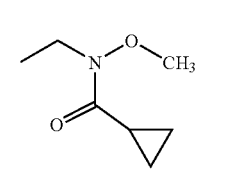 (3) | CH₃ | (2) Cl | (4) SO₂Me | logP$_{acidic}$ = 1.74 |

TABLE 3-continued

Examples of the compounds of the formula (VIII)

| Ex. No. | (position) A¹–A²–N–A³–R² \| R¹ | R¹² | (position) X | (position) Y | Physical data |
|---|---|---|---|---|---|
| VIII-54 | Ethyl-N(OCH₃)-CH₂-(tetrahydrofuran-3-yl) (3) | CH₃ | (2) Cl | (4) SO₂Me | logP$_{acidic}$ = 2.35 |
| VIII-55 | Ethyl-N(OC₂H₅)-CH₂-(tetrahydrofuran-3-yl) (3) | CH₃ | (2) Cl | (4) SO₂Me | logP$_{acidic}$ = 2.60 |
| VIII-56 | Ethyl-N(O-cyclopentyl)-CH₂-(tetrahydrofuran-3-yl) (3) | CH₃ | (2) Cl | (4) SO₂Me | logP$_{acidic}$ = 3.30 |
| VIII-57 | Ethyl-N(OCH₃)-CH₂-(furan-3-yl) (3) | CH₃ | (2) Cl | (4) SO₂Me | logP$_{acidic}$ = 2.91 |
| VIII-58 | Ethyl-N(OCH₃)-(tetrahydrofuran-3-yl) (3) | CH₃ | (2) Cl | (4) SO₂Me | logP$_{acidic}$ = 2.17 |
| VIII-59 | Ethyl-N(OCH₃)-(tetrahydropyran-3-yl) (3) | CH₃ | (2) Cl | (4) SO₂Me | logP$_{acidic}$ = 2.55 |
| VIII-60 | Ethyl-N(OCH₃)-(tetrahydropyran-4-yl) (3) | CH₃ | (2) Cl | (4) SO₂Me | logP$_{acidic}$ = 2.38 |
| VIII-61 | Ethyl-N(OCH₂CH₂OCH₃)(CH₃) (3) | CH₃ | (2) Cl | (4) SO₂Me | logP$_{acidic}$ = 2.26 |

TABLE 3-continued

Examples of the compounds of the formula (VIII)

| Ex. No. | R¹ (position) | R¹² | X (position) | Y (position) | Physical data |
|---|---|---|---|---|---|
| VIII-62 | Et-NH-O-CH₂CH₂-O-C₆H₅ (3) | CH₃ | (2) Cl | (4) SO₂Me | logP$_{acidic}$ = 2.93 |
| VIII-63 | Et-N(CH₃)-O-CH₂CH₂-O-C₆H₅ (3) | CH₃ | (2) Cl | (4) SO₂Me | logP$_{acidic}$ = 3.37 |
| VIII-64 | Et-N(CH₃)-O-CH₂-(tetrahydrofuran-2-yl) (3) | CH₃ | (2) Cl | (4) SO₂Me | logP$_{acidic}$ = 2.51 |
| VIII-65 | Et-N(CH₃)-O-CH₂-(tetrahydropyran-2-yl) (3) | CH₃ | (2) Cl | (4) SO₂Me | logP$_{acidic}$ = 2.87 |
| VIII-66 | —CH(CH₃)—N(H)—O—CH₃ (3) | CH₃ | (2) OCH₃ | (4) Cl | logP$_{acidic}$ = 2.76 |
| VIII-67 | —CH(C₂H₅)—N(H)—O—CH₃ (3) | CH₃ | (2) OCH₃ | (4) Cl | logP$_{acidic}$ = 3.43 |
| VIII-68 | Et-N(CH₃)-SO₂-CH₃ (3) | CH₃ | (2) Cl | (4) Cl | logP$_{acidic}$ = 2.15 |
| VIII-69 | Et-N(CH₃)-SO₂-CH₃ (3) | CH₃ | (2) Cl | (4) SO₂Me | logP$_{acidic}$ = 1.65 |
| VIII-70 | Et-N(CH₃)-SO₂-CH₃ (3) | CH₃ | (2) OCH₃ | (4) Cl | logP$_{acidic}$ = 2.09 |

TABLE 3-continued

Examples of the compounds of the formula (VIII)

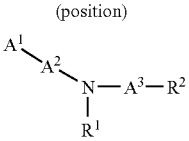

| Ex. No. | $R^1$ | $R^{12}$ | (position) X | (position) Y | Physical data |
|---|---|---|---|---|---|
| VIII-71 | 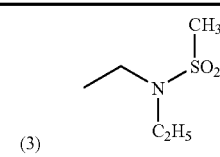 (3) | $CH_3$ | (2) $OCH_3$ | (4) Cl | $logP_{acidic} = 2.38$ |
| VIII-72 | 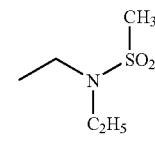 (3) | $CH_3$ | (2) Cl | (4) $SO_2Me$ | $logP_{acidic} = 1.88$ |
| VIII-73 | 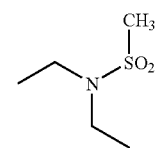 (3) | $CH_3$ | (2) Cl | (4) $SO_2Me$ | $logP_{acidic} = 2.03$ |

USE EXAMPLES

Example A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three weeks, the degree of damage to the plants is rated in % damage in comparison to the development of the untreated control. The figures denote:

0%=no effect (like untreated control)
100%=total destruction

In this test, for example, the compounds according to Preparation Examples 2, 4, 5 and 6 exhibit strong activity against weeds, and some of them are tolerated well by crop plants, such as, for example, maize and soya beans.

Example B

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)
100%=total destruction

In this test, for example, the compounds of Preparation Examples 2, 3, 4 and 5 exhibit strong activity against weeds, and some of them are tolerated well by crop plants, such as, for example, maize and wheat.

What is claimed is:

1. A compound of formula (I)

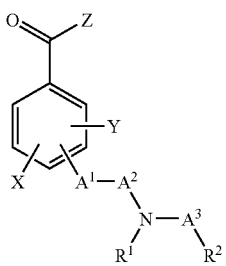

in which

A¹ represents O or S, or represents a group

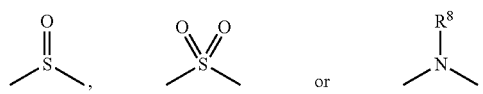

where

R⁸ represents hydrogen; represents optionally substituted alkyl, alkylcarbonylalkyl, alkoxycarbonylalkyl, alkylthio, alkylsulphinyl, alkylsulphonyl, alkenyl, alkenylcarbonylalkyl, alkenyloxycarbonylalkyl, alkynyl, alkynylcarbonylalkyl, alkynyloxycarbonylalkyl, cycloalkyl, cycloalkylcarbonylalkyl, cycloalkyloxycarbonylalkyl, cycloalkylalkyl, cycloalkylalkylcarbonylalkyl, cycloalkylalkoxycarbonylalkyl, aryl, arylcarbonylalkyl, aryloxycarbonylalkyl, arylalkyl, arylalkylcarbonylalkyl, or arylalkoxycarbonylalkyl, A² represents alkanediyl, alkenediyl, or alkynediyl, A³ represents O or S or represents a group

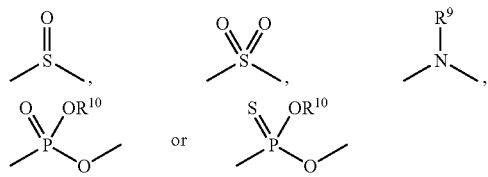

where

R⁹ represents hydrogen; or represents optionally substituted alkyl, alkylcarbonyl, alkoxycarbonyl, alkylthio, alkylsulphinyl, alkylsulphonyl, alkenyl, alkenylcarbonyl, alkenyloxycarbonyl, alkynyl, alkynylcarbonyl, alkynyloxycarbonyl, cycloalkyl, cycloalkylcarbonyl, cycloalkyloxycarbonyl, cycloalkylalkyl, cycloalkylalkylcarbonyl, cycloalkylalkoxycarbonyl, aryl, arylcarbonyl, aryloxycarbonyl, arylalkyl, arylalkylcarbonyl, arylalkoxycarbonyl, heterocyclyl, heterocyclylcarbonyl, or heterocyclylalkyl; or R⁹ together with R² and the nitrogen to which they are attached represent an optionally substituted heterocycle, and R¹⁰ represents hydrogen; represents formyl; or represents optionally substituted alkyl, alkylcarbonyl, alkoxycarbonyl, alkylaminocarbonyl, dialkylaminocarbonyl, alkenyl, alkenylcarbonyl, alkenyloxycarbonyl, alkynyl, alkynylcarbonyl, alkynyloxycarbonyl, cycloalkyl, cycloalkylcarbonyl, cycloalkyloxycarbonyl, cycloalkylaminocarbonyl, cycloalkylalkyl, aryl, arylcarbonyl, aryloxycarbonyl, arylaminocarbonyl, arylalkyl, arylalkylcarbonyl, arylalkoxycarbonyl, heterocyclyl, heterocyclylcarbonyl, or heterocyclylalkyl, R¹ represents hydrogen; or represents optionally substituted alkyl, alkylthio, alkylsulphinyl, alkylsulphonyl, alkenyl, alkynyl, cycloalkyl, cycloalkylalkyl, aryl, arylalkyl, arylcarbonylalkyl, heterocyclyl, or heterocyclylalkyl, R² represents hydrogen; represents formyl; or represents optionally substituted alkyl, alkylcarbonyl, alkoxycarbonyl, alkylaminocarbonyl, dialkylaminocarbonyl, alkenyl, alkenylcarbonyl, alkenyloxycarbonyl, alkynyl, alkynylcarbonyl, alkynyloxycarbonyl, cycloalkyl, cycloalkylcarbonyl, cycloalkyloxycarbonyl, cycloalkylaminocarbonyl, cycloalkylalkyl, aryl, arylcarbonyl, aryloxycarbonyl, arylaminocarbonyl, arylalkyl, arylalkylcarbonyl, arylalkoxycarbonyl, heterocyclyl, heterocyclylcarbonyl, or heterocyclylalkyl, X represents hydrogen, nitro, cyano, carboxyl, carbamoyl, thiocarbamoyl, or halogen; or represents optionally substituted alkyl, alkoxy, alkylthio, alkylsulphinyl, alkylsulphonyl, alkylamino, dialkylamino, or dialkylaminosulphonyl, Y represents hydrogen, nitro, cyano, carboxyl, carbamoyl, thiocarbamoyl, or halogen; or represents optionally substituted alkyl, alkoxy, alkylthio, alkylsulphinyl, alkylsulphonyl, alkylamino, dialkylamino, or dialkylaminosulphonyl, and Z represents one of the groups

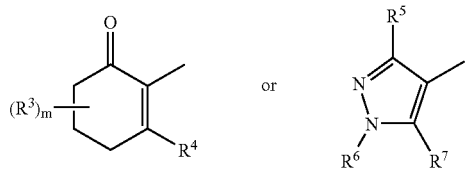

where m represents the numbers 0 to 6,

R³ represents hydrogen or halogen; or represents optionally substituted alkyl, alkylthio, or aryl; or when m represents 2, R³ together with a second R³ optionally represent oxygen or alkanediyl, R⁴ represents hydroxyl, formyloxy, or halogen; or represents optionally substituted alkoxy, cycloalkoxy, alkylthio, cycloalkylthio, alkylsulphinyl, alkylsulphonyl, alkylcarbonyloxy, alkoxycarbonyloxy, alkylaminocarbonyloxy, alkylsulphonyloxy, alkenyloxy, alkynyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, arylalkylsulphonyl, or heterocyclyl that contains at least one nitrogen atom and is attached via nitrogen, R⁵ represents hydrogen, cyano, carbamoyl, thiocarbamoyl, or halogen; or represents optionally substituted alkyl, alkoxy, alkylthio, alkylsulphinyl, alkylsulphonyl, alkoxycarbonyl, or cycloalkyl, R⁶ represents hydrogen; or represents optionally substituted alkyl, alkenyl, alkynyl, cycloalkyl, cycloalkylalkyl, aryl, or arylalkyl, and $R^7$ represents hydroxyl or formyloxy; or represents optionally substituted alkoxy, cycloalkyl, alkylcarbonyloxy, alkoxycarbonyloxy, alkoxycarbonylalkoxy, alkylaminocarbonyloxy, alkylsulphonyloxy, alkenyloxy, alkynyloxy, arylalkoxy, arylcarbonyloxy, arylcarbonylalkoxy, arylsulphonyloxy, or aminocarbonyloxy.

2. A compound according to claim 1 in which $A^2$ represents alkanediyl having 1 to 6 carbon atoms or represents alkenediyl or alkynediyl having in each case 2 to 6 carbon atoms;

$R^1$ represents hydrogen; represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, di($C_1$-$C_4$-alkyl)amino-, di($C_1$-$C_4$-alkyl)amino-carbonyl-, or N—($C_1$-$C_4$-alkoxy)-N—($C_1$-$C_4$-alkyl)aminocarbonyl-substituted alkyl having 1 to 6 carbon atoms; represents optionally halogen-substituted alkylthio, alkylsulphinyl, or alkylsulphonyl having in each case 1 to 6 carbon atoms; represents optionally halogen-substituted alkenyl or alkynyl having in each case 2 to 6 carbon atoms; represents optionally cyano-, halogen-, or $C_1$-$C_4$-alkyl-substituted cycloalkyl, cycloalkylalkyl having in each case 3 to 6 carbon atoms in the cycloalkyl groups and, if appropriate, 1 to 4 carbon atoms in the alkyl moiety; represents optionally cyano-, nitro-, halogen-, $C_1$-$C_4$-alkyl-, $C_1$-$C_4$-haloalkyl-, $C_1$-$C_4$-alkoxy-, or $C_1$-$C_4$-haloalkoxy-substituted aryl, arylalkyl, or arylcarbonylalkyl having in each case 6 or 10 carbon atoms in the aryl groups and, if appropriate, 1 to 4 carbon atoms in the alkyl moiety; or represents optionally nitro-, cyano-, halogen-, $C_1$-$C_4$-alkyl-, $C_1$-$C_4$-haloalkyl-, $C_1$-$C_4$-alkoxy-, or $C_1$-$C_4$-haloalkoxy-substituted heterocyclyl or heterocyclylalkyl where in each case the heterocyclyl grouping contains up to 10 carbon atoms and at least one heteroatom selected from the group consisting of N (but at most 5 N atoms), O (but at most 2 O atoms), S (but at most 2 S atoms), SO, and $SO_2$, and optionally contains one group selected from the group consisting of oxo (C═O), thioxo (C═S), imino (C═NH), cyanoimino (C═N—CN), and nitroimino (C═N—$NO_2$);

$R^2$ represents hydrogen; represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, or di($C_1$-$C_4$-alkyl)aminocarbonyl-substituted alkyl having 1 to 6 carbon atoms; represents optionally cyano-, halogen- or $C_1$-$C_4$-alkoxy-substituted alkylcarbonyl, alkoxycarbonyl, or alkylaminocarbonyl having in each case 1 to 6 carbon atoms in the alkyl groups; represents dialkylaminocarbonyl having in each case 1 to 4 carbon atoms in the alkyl groups; represents optionally halogen-substituted alkenyl, alkenylcarbonyl, alkenyloxycarbonyl, alkynyl, alkynylcarbonyl, or alkynyloxycarbonyl having in each case 3 to 6 carbon atoms in the alkenyl or alkynyl groups; represents optionally cyano-, halogen-, or $C_1$-$C_4$-alkyl-substituted cycloalkyl, cycloalkylcarbonyl, cycloalkyloxycarbonyl, cycloalkylalkyl, cycloalkylalkylcarbonyl, or cycloalkylalkoxycarbonyl having in each case 3 to 6 carbon atoms in the cycloalkyl groups and, if appropriate, 1 to 4 carbon atoms in the alkyl moiety; represents optionally nitro-, cyano-, halogen-, $C_1$-$C_4$-alkyl-, $C_1$-$C_4$-haloalkyl-, $C_1$-$C_4$-alkoxy-, or $C_1$-$C_4$-haloalkoxy-substituted aryl, arylcarbonyl, aryloxycarbonyl, arylaminocarbonyl, arylalkyl, arylalkylcarbonyl, arylalkoxycarbonyl, or arylalkylaminocarbonyl having in each case 6 or 10 carbon atoms in the aryl groups and, if appropriate, 1 to 4 carbon atoms in the alkyl moiety; or represents optionally nitro-, cyano-, halogen-, $C_1$-$C_4$-alkyl-, $C_1$-$C_4$-haloalkyl-, $C_1$-$C_4$-alkoxy-, or $C_1$-$C_4$-haloalkoxy-substituted heterocyclyl, heterocyclylcarbonyl, or heterocyclylalkyl, where the heterocyclyl group contains in each case up to 10 carbon atoms and at least one heteroatom selected from the group consisting of N (but at most 5 N atoms), O (but at most 2 O atoms), S (but at most 2 S atoms), SO, and $SO_2$, and optionally contains one group selected from the group consisting of oxo (C═O), thioxo (C═S), imino (C═NH), cyanoimino (C═N—CN), and nitroimino (C═N—$NO_2$);

$R^3$ represents hydrogen or halogen; represents optionally cyano-, halogen-, $C_1$-$C_4$-alkoxy-, $C_1$-$C_4$-alkylthio-, $C_1$-$C_4$-alkylsulphinyl, or $C_1$-$C_4$-alkylsulphonyl-substituted alkyl or alkylthio having in each case 1 to 6 carbon atoms; or represents phenyl; or when m represents 2, $R^3$ together with a second $R^3$ optionally represents oxygen or alkanediyl having 3 to 5 carbon atoms;

$R^4$ represents hydroxyl, formyloxy, or halogen; represents optionally cyano-, halogen-, $C_1$-$C_4$-alkoxy-, $C_1$-$C_4$-alkylsulphinyl-, or $C_1$-$C_4$-alkylsulphonyl-substituted alkoxy, alkylthio, alkylsulphinyl, alkylsulphonyl, alkylcarbonyloxy, alkoxycarbonyloxy, alkylaminocarbonyloxy, or alkylsulphonyloxy having in each case 1 to 6 carbon atoms; represents optionally halogen-substituted alkenyloxy or alkynyloxy having in each case 3 to 6 carbon atoms; represents optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-haloalkylthio-, $C_1$-$C_4$-haloalkylsulphinyl-, $C_1$-$C_4$-alkylsulphonyl-, or $C_1$-$C_4$-haloalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, or arylalkylsulphonyl having in each case 6 or 10 carbon atoms in the aryl group and, if appropriate, 1 to 4 carbon atoms in the alkyl moiety; represents optionally cyano-, halogen-, oxo-, hydroxyl-, $C_1$-$C_4$-alkoxy-, or $C_1$-$C_4$-alkyl-substituted heterocyclyl having 5 or 6 ring atoms comprising at least 1 nitrogen atom and optionally up to 2 oxygen atoms, up to 2 sulphur atoms, and 3 additional nitrogen atoms, where in total not more than 4 heteroatoms are present and where the heterocycle is attached via the nitrogen;

$R^5$ represents hydrogen, cyano, carbamoyl, thiocarbamoyl, or halogen; represents optionally cyano-, halogen-, $C_1$-$C_4$-alkoxy-, $C_1$-$C_4$-alkylsulphinyl-, or $C_1$-$C_4$-alkylsulphonyl-substituted alkyl, alkoxy, alkylthio, alkylsulphinyl, alkylsulphonyl, or alkoxycarbonyl having in each case 1 to 6 carbon atoms in the alkyl groups; or represents optionally cyano-, halogen-, or $C_1$-$C_4$-alkyl-substituted cycloalkyl having 3 to 6 carbon atoms;

$R^6$ represents hydrogen; represents optionally cyano-, halogen-, $C_1$-$C_4$-alkoxy-, $C_1$-$C_4$-alkylthio-, $C_1$-$C_4$-alkylsulphinyl-, or $C_1$-$C_4$-alkylsulphonyl-substituted alkyl having 1 to 6 carbon atoms; represents optionally cyano- or halogen-substituted alkenyl or alkynyl having in each case 3 to 6 carbon atoms; represents optionally cyano-, halogen-, or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety; or represents optionally nitro-, cyano-, halogen-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$- alkylsulphonyl-, or $C_1$-$C_4$-haloalkylsulphonyl-substituted aryl or arylalkyl having in each case 6 or 10 carbon atoms in the aryl group and, if appropriate, 1 to 4 carbon atoms in the alkyl moiety;

$R^7$ represents hydroxyl or formyloxy; represents optionally alkyl-, cyano-, halogen-, or $C_1$-$C_4$-alkoxy-substituted alkoxy, alkylcarbonyloxy, alkoxycarbonyloxy, alkoxycarbonylalkoxy, alkylaminocarbonyloxy, or alkylsulphonyloxy having in each case 1 to 6 carbon atoms in the alkyl groups; represents optionally cyano- or halogen-substituted alkenyloxy or alkynyloxy having in each case 3 to 6 carbon atoms; or represents optionally nitro-, cyano-, halogen-, $C_1$-$C_4$-alkyl-, $C_1$-$C_4$-haloalkyl-, $C_1$-$C_4$-alkoxy-, haloalkoxy-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, or $C_1$-$C_4$-haloalkylsulphonyl-substituted arylalkoxy, arylcarbonyloxy, arylcarbonylalkoxy, or arylsulphonyloxy having in each case 6 or 10 carbon atoms in the aryl group and, if appropriate, 1 to 4 carbon atoms in the alkyl moiety;

$R^8$ represents hydrogen; represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, or di($C_1$-$C_4$-alkyl)aminocarbonyl-substituted alkyl having 1 to 6 carbon atoms; represents optionally cyano-, halogen-, or $C_1$-$C_4$-alkoxy-substituted alkylcarbonyl or alkoxycarbonyl having in each case 1 to 6 carbon atoms in the alkyl groups; represents optionally halogen-substituted alkylthio, alkylsulphinyl, or alkylsulphonyl having in each case 1 to 6 carbon atoms; represents optionally halogen-substituted alkenyl, alkenylcarbonyl, alkenyloxycarbonyl, alkynyl, alkynylcarbonyl, or alkynyloxycarbonyl having in each case 2 to 6 carbon atoms in the alkenyl or alkynyl groups; represents optionally cyano-, halogen-, or $C_1$-$C_4$-alkyl-substituted cycloalkyl, cycloalkylcarbonyl, cycloalkyloxycarbonyl, cycloalkylalkyl, cycloalkylalkylcarbonyl, or cycloalkylalkoxycarbonyl having in each case 3 to 6 carbon atoms in the cycloalkyl groups and, if appropriate, 1 to 4 carbon atoms in the alkyl moiety; or represents optionally cyano-, nitro-, halogen-, $C_1$-$C_4$-alkyl-, $C_1$-$C_4$-haloalkyl-, $C_1$-$C_4$-alkoxy-, or $C_1$-$C_4$-haloalkoxy-substituted aryl, arylcarbonyl, aryloxycarbonyl, arylalkyl, arylalkylcarbonyl, or arylalkoxycarbonyl having in each case 6 or 10 carbon atoms in the aryl groups and, if appropriate, 1 to 4 carbon atoms in the alkyl moiety;

$R^9$ represents hydrogen; represents optionally hydroxyl-, amino-, cyano-, carbamoyl-, halogen-, $C_1$-$C_4$-alkoxy-, $C_1$-$C_4$-alkyl-carbonyl-, $C_1$-$C_4$-alkoxy-carbonyl-, $C_1$-$C_4$-alkylaminocarbonyl, or di($C_1$-$C_4$-alkyl)aminocarbonyl-substituted alkyl having 1 to 6 carbon atoms; represents optionally cyano-, halogen-, or $C_1$-$C_4$-alkoxy-substituted alkylcarbonyl or alkoxycarbonyl having in each case 1 to 6 carbon atoms in the alkyl groups; represents optionally halogen-substituted alkylthio, alkylsulphinyl, or alkylsulphonyl having in each case 1 to 6 carbon atoms; represents optionally halogen-substituted alkenyl, alkenylcarbonyl, alkenyloxycarbonyl, alkynyl, alkynylcarbonyl, or alkynyloxycarbonyl having in each case 2 to 6 carbon atoms in the alkenyl or alkynyl groups; represents optionally cyano-, halogen-, or $C_1$-$C_4$-alkyl-substituted cycloalkyl, cycloalkylcarbonyl, cycloalkyloxycarbonyl, cycloalkylalkyl, cycloalkylalkylcarbonyl, or cycloalkylalkoxycarbonyl having in each case 3 to 6 carbon atoms in the cycloalkyl groups and, if appropriate, 1 to 4 carbon atoms in the alkyl moiety; represents optionally cyano-, nitro-, halogen-, $C_1$-$C_4$-alkyl-, $C_1$-$C_4$-haloalkyl-, $C_1$-$C_4$-alkoxy-, or $C_1$-$C_4$-haloalkoxy-substituted aryl, arylcarbonyl, aryloxycarbonyl, arylalkyl, arylalkylcarbonyl, or arylalkoxycarbonyl having in each case 6 or 10 carbon atoms in the aryl groups and, if appropriate, 1 to 4 carbon atoms in the alkyl moiety; or represents optionally nitro-, cyano-, halogen-, $C_1$-$C_4$-alkyl-, $C_1$-$C_4$-haloalkyl-, $C_1$-$C_4$-alkoxy-, or $C_1$-$C_4$-haloalkoxy-substituted heterocyclyl, heterocyclylcarbonyl, or heterocyclylalkyl, where in each case the heterocyclyl grouping contains up to 10 carbon atoms and at least one heteroatom selected from the group consisting of N (but at most 5 N atoms), O (but at most 2 O atoms), S (but at most 2 S atoms), SO, and $SO_2$, and optionally contains one group selected from the group consisting of oxo (C=O), thioxo (C=S), imino (C=NH), cyanoimino (C=N—CN), and nitroimino (C=N—$NO_2$); or $R^9$ together with $R^2$ and the nitrogen to which they are attached represent an optionally nitro-, cyano-, halogen-, $C_1$-$C_4$-alkyl-, $C_1$-$C_4$-haloalkyl-, $C_1$-$C_4$-alkoxy-, or $C_1$-$C_4$-haloalkoxy-substituted heterocycle that contains 1 nitrogen atom and 1 to 10 carbon atoms and optionally one further heteroatom selected from the group consisting of N (but at most 4 further N atoms), O (but at most 2 O atoms), S (but at most 2 S atoms), SO, and SO.sub.2, and optionally contains one group selected from the group consisting of oxo (C=O), thioxo (C=S), imino (C=NH), cyanoimino (C=N—CN), and nitroimino (C=N—$NO_2$);

$R^{10}$ represents hydrogen or formyl; represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, or di-($C_1$-$C_4$-alkyl)aminocarbonyl-substituted alkyl having 1 to 6 carbon atoms;

X represents hydrogen, nitro, cyano, carboxyl, carbamoyl, thiocarbamoyl, or halogen; or represents optionally cyano-, halogen-, $C_1$-$C_4$-alkoxy-, $C_1$-$C_4$-alkylthio-, $C_1$-$C_4$-alkylsulphinyl-, or $C_1$-$C_4$-alkylsulphonyl-substituted alkyl, alkoxy, alkylthio, alkylsulphinyl, alkylsulphonyl, alkylamino, dialkylamino, or dialkylaminosulphonyl having in each case 1 to 6 carbon atoms in the alkyl groups;

Y represents hydrogen, nitro, cyano, carboxyl, carbamoyl, thiocarbamoyl, or halogen; or represents optionally cyano-, halogen-, $C_1$-$C_4$-alkoxy-, $C_1$-$C_4$-alkylsulphinyl-, or $C_1$-$C_4$-alkylsulphonyl-substituted alkyl, alkoxy, alkylthio, alkylsulphinyl, alkylsulphonyl, alkylamino, dialkylamino, or dialkylaminosulphonyl having in each case 1 to 6 carbon atoms in the alkyl groups; and m represents the numbers 0, 1, 2, or 3.

3. A compound according to claim 1 in which $A^2$ represents methylene (—$CH_2$—), ethane-1,1-diyl (—CH($CH_3$)—), ethane-1,2-diyl (dimethylene, —$CH_2CH_2$—), propane-1,1-diyl(—CH($C_2H_5$)—), propane-1,2-diyl(—CH($CH_3$)$CH_2$—), propane-1,3-diyl (—$CH_2CH_2CH_2$—), butane-1,3-diyl(—CH($CH_3$)$CH_2CH_2$—), butane-1,4-diyl(—$CH_2CH_2CH_2CH_2$—), ethenediyl, propenediyl, butenediyl, ethynediyl, propynediyl, or butynediyl;

$R^1$ represents hydrogen; represents optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylamino-, diethylamino-, dimethylaminocarbonyl-, diethylaminocarbonyl-, or N-methoxy-N-methylamino-carbonyl-substituted methyl, ethyl, n- or i-propyl, n-, i-, or s-butyl, or n-, i-, or s-pentyl; represents optionally fluorine- and/or chlorine-substituted methylthio, ethylthio, n- or i-propylthio, n-, s-, or t-butylthio, methylsulphinyl, ethylsulphinyl, n- or i-propylsulphinyl, methylsulphonyl, ethylsulphonyl, or n- or i-propylsulphonyl; represents optionally fluorine-, chlorine-, and/or bromine-substituted propenyl, butenyl, propynyl, or butyryl; represents optionally cyano-, fluorine-, chlorine-, methyl-, or ethyl-substituted cyclopropyl, cyclobutyl, cyclopentyl, cyclohexyl, cyclopropylmethyl, cyclobutylmethyl, cyclopentylmethyl, or cyclohexylmethyl; represents optionally cyano-, nitro-, fluorine-, chlorine-, bromine-, methyl-, ethyl-, n- or i-propyl-, n-, s-, or t-butyl-, trifluoromethyl-, methoxy-, ethoxy-, s- or i-propoxy-, n-, s-, or t-butoxy-, difluoromethoxy-, or trifluoromethoxy-substituted phenyl, benzoyl, benzyl, phenylethyl, or phenylcarbonylmethyl; or represents optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, or trifluoromethoxy-substituted heterocyclyl or heterocyclylalkyl selected from the group consisting of furyl, furylmethyl, thienyl, thienylmethyl, pyrrolidinyl, oxopyrrolidinyl, pyrrolyl, indolyl, pyrrolylmethyl, pyrazolyl, pyrazolylmethyl, oxazolyl, oxazolylmethyl, isoxazolyl, thiazolyl, thiazolylmethyl, dihydropyranyl, dihydropyranylmethyl, piperidinyl, oxopiperidinyl, morpholinyl, piperazinyl, pyridinyl, pyridinylcarbonyl, and pyridinylmethyl;

$R^2$ represents hydrogen; represents optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl-, or diethylaminocarbonyl-substituted methyl, ethyl, n- or i-propyl, n-, s-, or t-butyl, or n-, s-, or t-pentyl; represents optionally cyano-, fluorine-, chlorine-, methoxy-, ethoxy-, or n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, or n- or i-propylaminocarbonyl; represents dimethylaminocarbonyl, diethylaminocarbonyl, or dipropylaminocarbonyl; represents optionally fluorine-, chlorine-, and/or bromine-substituted propenyl, butenyl, propenylcarbonyl, butenylcarbonyl, propenyloxycarbonyl, butenyloxycarbonyl, propenylaminocarbonyl, butenylaminocarbonyl, propynyl, butynyl, propynylcarbonyl, butynylcarbonyl, propynyloxycarbonyl, or butynyloxycarbonyl; represents optionally cyano-, fluorine-, chlorine-, methyl-, or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropyloxycarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, or cyclohexylmethoxycarbonyl; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, or trifluoromethoxy-substituted phenyl, naphthyl, benzoyl, phenoxycarbonyl, phenylaminocarbonyl, benzyl, phenylethyl, phenylmethylcarbonyl, or phenylmethoxycarbonyl; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, or trifluoromethoxy-substituted furyl, furylcarbonyl, furylmethyl, thienyl, thienylcarbonyl, thienylmethyl, pyrrolidinyl, oxopyrrolidinyl, pyrrolyl, indolyl, pyrrolylmethyl, pyrazolyl, pyrazolylcarbonyl, pyrazolylmethyl, oxazolyl, oxazolylmethyl, isoxazolyl, isoxazolylcarbonyl, thiazolyl, thiazolylmethyl, 2-oxo-1,3-diazacyclopentyl (2-oxoimidazolidinyl), piperidinyl, oxopiperidinyl, 2-oxo-1,3-diazacyclohexyl, morpholinyl, thiomorpholinyl, 3-oxomorpholinyl, 3-oxothiomorpholinyl, piperazinyl, pyridinyl, pyridinylcarbonyl, or pyridinylmethyl;

$R^3$ represents hydrogen, fluorine, chlorine, or bromine; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, n-, i-, s-, or t-butyl, methylthio, ethylthio, n- or i-propylthio, or n-, i-, s-, or t-butylthio; or represents phenyl, or when m represents 2, $R^3$ together with a second $R^3$ optionally represents oxygen, propane-1,3-diyl, or butane-1,4-diyl;

$R^4$ represents hydroxyl, formyloxy, fluorine, or chlorine; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl; represents optionally cyano-, oxo-, fluorine-, chlorine-, methyl-, ethyl-, methoxy-, ethoxy-, methylthio-, or ethylthio-substituted pyrrolyl, pyrrolinyl, pyrrolidinyl, pyrazolyl, pyrazolinyl, pyrazolidinyl, imidazolyl, imidazolinyl, imidazolidinyl, triazolyl, triazolinyl, triazolidinyl, tetrazolyl, tetrazolinyl, tetrazolidinyl, oxazolyl, oxazolinyl, oxazolidinyl, isoxazolyl, isoxazolinyl, isoxazolidinyl, thiazolyl, thiazolinyl, thiazolidinyl, thiadiazolyl, indolyl, piperidinyl, piperazinyl, oxazinyl, thiazinyl, or morpholinyl;

R⁵ represents hydrogen, cyano, carbamoyl, thiocarbamoyl, fluorine, chlorine, or bromine; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, n-, s-, or t-butyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, or n- or i-propoxycarbonyl; or represents optionally cyano-, fluorine-, chlorine-, methyl-, or ethyl-substituted cyclopropyl, cyclobutyl, cyclopentyl, or cyclohexyl;

R⁶ represents hydrogen; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, or n-, s-, or t-butyl; represents optionally cyano-, fluorine-, chlorine-, or bromine-substituted propenyl, butenyl, propynyl, or butynyl; represents optionally cyano-, fluorine-, chlorine-, methyl-, or ethyl-substituted cyclopropyl, cyclobutyl, cyclopentyl, cyclohexyl, cyclopropylmethyl, cyclobutylmethyl, cyclopentylmethyl, or cyclohexylmethyl; or represents optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, n-, s-, or t-butylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyl or phenylmethyl;

R⁷ represents hydroxyl or formyloxy; represents optionally alkyl-, cyano-, fluorine-, chlorine-, methoxy-, ethoxy-, or n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, ethoxycarbonyl methoxy, methoxycarbonylmethoxy, methylsulphonyloxy, ethylsulphonyloxy, or n- or i-propylsulphonyloxy; represents optionally cyano-, fluorine-, chlorine-, or bromine-substituted propenyloxy, butenyloxy, propynyloxy, or butynyloxy; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substitute-d phenylmethoxy, phenylcarbonyloxy, phenylcarbonylmethoxy, or phenylsulphonyloxy;

R⁸ represents hydrogen; represents optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl-, or diethylaminocarbonyl-substituted methyl, ethyl, n- or i-propyl, n-, i-, or s-butyl, or n-, i-, or s-pentyl; represents optionally cyano-, fluorine-, chlorine-, methoxy-, ethoxy-, or n- or i-propoxy-substituted acetyl, propionyl, n- or i-butyroyl, methoxycarbonyl, ethoxycarbonyl, or n- or i-propoxycarbonyl; represents optionally fluorine- and/or chlorine-substituted methylthio, ethylthio, n- or i-propylthio, n-, s-, or t-butylthio, methylsulphinyl, ethylsulphinyl, n- or i-propylsulphinyl, methylsulphonyl, ethylsulphonyl, or n- or i-propylsulphonyl; represents optionally fluorine-, chlorine-, and/or bromine-substituted propenyl, butenyl, propenylcarbonyl, butenylcarbonyl, propenyloxycarbonyl, butenyloxycarbonyl, propynyl, butynyl, propynylcarbonyl, butynylcarbonyl, propynyloxycarbonyl, or butynyloxycarbonyl; represents optionally cyano-, fluorine-, chlorine-, methyl-, or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropyloxycarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, or cyclohexylmethoxycarbonyl; or represents optionally cyano-, nitro-, fluorine-, chlorine-, bromine-, methyl-, ethyl-, n- or i-propyl-, n-, i-, s-, or t-butyl-, trifluoromethyl-, methoxy-, ethoxy-, s- or i-propoxy-, n-, i-, s-, or t-butoxy-, difluoromethoxy-, or trifluoromethoxy-substituted phenyl, benzoyl, phenoxycarbonyl, benzyl, phenylethyl, phenylmethylcarbonyl, or phenylmethoxycarbonyl;

R⁹ represents hydrogen; represents optionally hydroxyl-, amino-, cyano-, carbamoyl-, fluorine-, chlorine-, methoxy-, ethoxy-, n- or i-propoxy-, acetyl-, propionyl-, n- or i-butyroyl-, methoxycarbonyl-, ethoxycarbonyl-, n- or i-propoxycarbonyl-, methylaminocarbonyl-, ethylaminocarbonyl-, n- or i-propylaminocarbonyl-, dimethylaminocarbonyl-, or diethylaminocarbonyl-substituted methyl, ethyl, n- or i-propyl, n-, i-, or s-butyl, n-, i-, or s-pentyl; represents optionally cyano-, fluorine-, chlorine-, methoxy-, ethoxy-, or n- or i-propoxy-substituted acetyl, propionyl, n- or i-butyroyl, methoxycarbonyl, ethoxycarbonyl, or n- or i-propoxycarbonyl; represents optionally fluorine- and/or chlorine-substituted methylthio, ethylthio, n- or i-propylthio, n-, i-, s-, or t-butylthio, methylsulphinyl, ethylsulphinyl, n- or i-propylsulphinyl, methylsulphonyl, ethylsulphonyl, or n- or i-propylsulphonyl; represents optionally fluorine-, chlorine-, and/or bromine-substituted propenyl, butenyl, propenylcarbonyl, butenylcarbonyl, propenyloxycarbonyl, butenyloxycarbonyl, propynyl, butynyl, propynylcarbonyl, butynylcarbonyl, propynyloxycarbonyl, or butynyloxycarbonyl; represents optionally cyano-, fluorine-, chlorine-, methyl-, or ethyl-substituted cyclopropyl, cyclobutyl, cyclopentyl, cyclohexyl, cyclopropylcarbonyl, cyclobutylcarbonyl, cyclopentylcarbonyl, cyclohexylcarbonyl, cyclopropyloxycarbonyl, cyclobutyloxycarbonyl, cyclopentyloxycarbonyl, cyclohexyloxycarbonyl, cyclopropylmethyl, cyclobutylmethyl, cyclopentylmethyl, cyclohexylmethyl, cyclopropylmethylcarbonyl, cyclobutylmethylcarbonyl, cyclopentylmethylcarbonyl, cyclohexylmethylcarbonyl, cyclopropylmethoxycarbonyl, cyclobutylmethoxycarbonyl, cyclopentylmethoxycarbonyl, or cyclohexylmethoxycarbonyl; represents optionally cyano-, nitro-, fluorine-, chlorine-, bromine-, methyl-, ethyl-, n- or i-propyl-, n-, s-, or t-butyl-, trifluoromethyl-, methoxy-, ethoxy-, s- or i-propoxy-, n-, s-, or t-butoxy-, difluoromethoxy-, or trifluoromethoxy-substituted phenyl, benzoyl, phenoxycarbonyl, benzyl, phenylethyl, phenylmethylcarbonyl, or phenylmethoxycarbonyl; or represents optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, or trifluoromethoxy-substituted heterocyclyl, heterocyclylcarbonyl and heterocyclylalkyl selected from the group consisting of furyl, furylcarbonyl, furylmethyl, thienyl, thienylcarbonyl, thienylmethyl, pyrrolidinyl, oxopyrrolidinyl, pyrrolyl, indolyl, pyrrolylmethyl, pyrazolyl, pyrazolylcarbonyl, pyrazolylmethyl, oxazolyl, oxazolylmethyl, isoxazolyl, isoxazolylcarbonyl, thiazolyl, thiazolylmethyl, piperidinyl, oxopiperidinyl, morpholinyl, piperazinyl, pyridinyl, pyridinylcarbonyl, and pyridinylmethyl; or R.sup.9 together with R.sup.2 and the nitrogen to which they are attached represent optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, or trifluoromethoxy-substituted pyrrolidinyl, oxopyrrolidinyl, pyrrolyl, indolyl, pyrazolyl, oxazolyl, isoxazolyl, dihydropyranyl, piperidinyl, thiomorpholinyl, 3-oxomorpholinyl, 3-oxothiomorpholinyl, oxopiperidinyl, morpholinyl, piperazinyl, imidazolyl, imidazolidinyl, oxoimidazolidinyl, triazol, triazolinyl, tetrazolinyl, or pyridinyl;

$R^{10}$ represents hydrogen or formyl; represents optionally cyano-, halogen-, $C_1$-$C_4$-alkoxy-, $C_1$-$C_4$-alkyl-carbonyl-, $C_1$-$C_4$-alkoxycarbonyl-, $C_1$-$C_4$-alkylaminocarbonyl-, or di($C_1$-$C_4$-alkyl)aminocarbonyl-substituted alkyl having 1 to 6 carbon atoms;

X represents hydrogen, nitro, cyano, carboxyl, carbamoyl, thiocarbamoyl, fluorine, chlorine, bromine, or iodine; or represents optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, s-, or t-butyl, methoxy, ethoxy, n- or i-propoxy, n-, s-, or t-butoxy, methylthio, ethylthio, n- or i-propylthio, n-, s-, or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, s-, or t-butylamino, dimethylamino, diethylamino, dimethylaminosulphonyl, or diethylaminosulphonyl;

Y represents hydrogen, nitro, cyano, carboxyl, carbamoyl, thiocarbamoyl, fluorine, chlorine, bromine, or iodine; or represents optionally cyano-, fluorine-, chlorine-, methoxy-, ethoxy-, methylthio-, ethylthio-, methylsulphinyl-, ethylsulphinyl-, methylsulphonyl-, or ethylsulphonyl-substituted methyl, ethyl, n- or i-propyl, n-, s-, or t-butyl, methoxy, ethoxy, n- or i-propoxy, n-, s-, or t-butoxy, methylthio, ethylthio, n- or i-propylthio, n-, s-, or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, s-, or t-butylamino, dimethylamino, diethylamino, dimethylaminosulphonyl, or diethylaminosulphonyl; and m represents the numbers 0, 1, or 2.

4. A compound according to claim 1 in which $A^2$ represents methylene (—$CH_2$—), ethane-1,1-diyl (—$CH(CH_3)$—), ethane-1,2-diyl (dimethylene, —$CH_2CH_2$—), propane-1,2-diyl(—$CH(CH_3)CH_2$—), or propane-1,3-diyl (—$CH_2CH_2CH_2$—);

$R^1$ represents hydrogen; represents optionally cyano-, fluorine-, chlorine-, methoxy-, ethoxy-, n- or i-propoxy-, acetyl-, propionyl-, methoxycarbonyl-, or ethoxycarbonyl-substituted methyl, ethyl, or n- or i-propyl; represents optionally cyano-, fluorine-, chlorine-, methoxy-, ethoxy-, or n- or i-propoxy-substituted acetyl, propionyl, methoxycarbonyl, or ethoxycarbonyl; represents optionally fluorine- and/or chlorine-substituted methylthio, ethylthio, n- or i-propylthio, n-, s-, or t-butylthio, methylsulphinyl, ethylsulphinyl, methylsulphonyl, or ethylsulphonyl; represents optionally fluorine-, chlorine-, and/or bromine-substituted propenyl, butenyl, propynyl, or butynyl; represents optionally fluorine-, chlorine-, or methyl-substituted cyclopropyl, cyclopropylcarbonyl, or cyclopropylmethyl; or represents optionally cyano-, nitro-, fluorine-, chlorine-, bromine-, methyl-, ethyl-, n- or i-propyl-, n-, i-, s-, or t-butyl-, trifluoromethyl-, methoxy-, ethoxy-, s- or i-propoxy-, difluoromethoxy-, or trifluoromethoxy-substituted phenyl, benzoyl, phenoxycarbonyl, benzyl, phenylmethylcarbonyl, or phenylmethoxycarbonyl;

$R^2$ represents hydrogen; represents optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, or n- or i-propoxycarbonyl-substituted methyl, ethyl, n- or i-propyl, n-, i-, s-, or t-butyl, or n-, i-, s-, or t-pentyl; represents optionally cyano-, fluorine-, chlorine-, methoxy-, ethoxy-, or n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, or n- or i-propylaminocarbonyl; represents dimethylaminocarbonyl; represents optionally fluorine- and/or chlorine-substituted methylthio, ethylthio, n- or i-propylthio, n-, i-, s-, or t-butylthio, methylsulphinyl, ethylsulphinyl, methylsulphonyl, or ethylsulphonyl; represents optionally fluorine-, chlorine-, and/or bromine-substituted propenyl, butenyl, propynyl, or butynyl; represents optionally fluorine-, chlorine-, or methyl-substituted cyclopropyl, cyclopropylcarbonyl, or cyclopropylmethyl; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, or trifluoromethoxy-substituted phenyl, benzoyl, phenoxycarbonyl, phenylaminocarbonyl, benzyl, phenylethylcarbonyl, or phenylmethoxycarbonyl; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, or trifluoromethoxy-substituted heterocyclyl, heterocyclylcarbonyl or heterocyclylalkyl selected from the group consisting of furyl, furylcarbonyl, furylmethyl, thienyl, thienylcarbonyl, thienylmethyl, pyrrolidinyl, pyrrolyl, indolyl, pyrrolylmethyl, pyrazolyl, pyrazolylmethyl, isoxazolyl, piperidinyl, morpholinyl, thiomorpholinyl, 3-oxo-morpholinyl, 3-oxothiomorpholinyl, piperazinyl, pyridinyl, and pyridinylmethyl;

$R^3$ represents hydrogen; represents optionally fluorine- and/or chlorine-substituted methyl, ethyl, n- or i-propyl, methylthio, ethylthio, or n- or i-propylthio; or represents phenyl; or when m represents 2, R.sup.3 together with a second R.sup.3 optionally represents oxygen, propane-1,3-diyl, or butane-1,4-diyl;

$R^4$ represents hydroxyl; represents formyloxy; represents optionally fluorine- and/or chlorine-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine- and/or chlorine-substituted propenyloxy, butenyloxy, propynyloxy, or butynyloxy; represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, or trifluoromethoxy-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl; represents optionally cyano-, oxo-, fluorine-, chlorine-, methyl-, ethyl-, methoxy-, ethoxy-, methylthio-, or ethylthio-substituted pyrrolyl, pyrrolinyl, pyrrolidinyl, pyrazolyl, pyrazolinyl, pyrazolidinyl, imidazolyl, imidazolinyl, imidazolidinyl, triazolyl, triazolinyl, triazolidinyl, tetrazolyl, tetrazolinyl, tetrazolidinyl, oxazolyl, oxazolinyl, oxazolidinyl, isoxazolyl, isoxazolidinyl, isoxazolidinyl, thiazolyl, thiazolinyl, thiazolidinyl, thiadiazolyl, indolyl, piperidinyl, piperazinyl, oxazinyl, thiazinyl, or morpholinyl;

$R^5$ represents hydrogen, cyano, fluorine, or chlorine; represents optionally fluorine- and/or chlorine-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, or n- or i-propoxycarbonyl; or represents optionally cyano-, fluorine-, chlorine-, or methyl-substituted cyclopropyl;

$R^6$ represents hydrogen; represents optionally cyano-, fluorine-, chlorine-, methoxy-, or ethoxy-substituted methyl, ethyl, n- or i-propyl, n-, s-, or t-butyl; represents optionally fluorine- or chlorine-substituted propenyl, butenyl, propynyl, or butynyl; represents optionally fluorine-, chlorine-, or methyl-substituted cyclopropyl, cyclobutyl, cyclopentyl, or cyclohexyl; or represents optionally fluorine-, chlorine-, bromine-, methyl-, ethyl-, n- or i-propyl-, trifluoromethyl-, methoxy-, ethoxy-, n- or i-propoxy-, difluoromethoxy-, or trifluoromethoxy-substituted phenyl or phenylmethyl;

$R^7$ represents hydroxyl; represents formyloxy; represents optionally alkyl-, cyano-, fluorine-, chlorine-, methoxy-, ethoxy-, or n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, ethoxycarbonylmethoxy, methoxycarbonylmethoxy, methylsulphonyloxy, ethylsulphonyloxy, or n- or i-propylsulphonyloxy; represents optionally fluorine- and/or chlorine-substituted propenyloxy, butenyloxy, propynyloxy, or butynyloxy; or represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, or trifluoromethoxy-substituted phenylmethoxy, phenylcarbonyloxy, phenylcarbonylmethoxy, or phenylsulphonyloxy;

$R^8$ represents hydrogen; represents optionally cyano-, fluorine-, chlorine-, methoxy-, ethoxy-, n- or i-propoxy-, acetyl-, propionyl-, methoxycarbonyl-, or ethoxycarbonyl-substituted methyl, ethyl, or n- or i-propyl; represents optionally cyano-, fluorine-, chlorine-, methoxy-, ethoxy-, or n- or i-propoxy-substituted acetyl, propionyl, methoxycarbonyl, or ethoxycarbonyl; represents optionally fluorine- and/or chlorine-substituted methylthio, ethylthio, n- or i-propylthio, n-, s-, or t-butylthio, methylsulphinyl, ethylsulphinyl, methylsulphonyl, or ethylsulphonyl; represents optionally fluorine-, chlorine-, and/or bromine-substituted propenyl, butenyl, propynyl, or butynyl; represents optionally fluorine-, chlorine- or methyl-substituted cyclopropyl, cyclopropylcarbonyl, or cyclopropylmethyl; represents optionally cyano-, nitro-, fluorine-, chlorine-, bromine-, methyl-, ethyl-, n- or i-propyl-, n-, s-, or t-butyl-, trifluoromethyl-, methoxy-, ethoxy-, s- or i-propoxy-, difluoromethoxy-, or trifluoromethoxy-substituted phenyl, benzoyl, phenoxycarbonyl, benzyl, phenylmethylcarbonyl, or phenylmethoxycarbonyl;

$R^9$ represents hydrogen; represents optionally cyano-, fluorine-, chlorine-, methoxy-, ethoxy-, n- or i-propoxy-, acetyl-, propionyl-, methoxycarbonyl-, or ethoxycarbonyl-substituted methyl, ethyl, or n- or i-propyl; represents optionally cyano-, fluorine-, chlorine-, methoxy-, ethoxy-, or n- or i-propoxy-substituted acetyl, propionyl, methoxycarbonyl, or ethoxycarbonyl; represents optionally fluorine- and/or chlorine-substituted methylthio, ethylthio, n- or i-propylthio, n-, s-, or t-butylthio, methylsulphinyl, ethylsulphinyl, methylsulphonyl, or ethylsulphonyl; represents optionally fluorine-, chlorine-, and/or bromine-substituted propenyl, butenyl, propynyl, or butynyl; represents optionally fluorine-, chlorine-, or methyl-substituted cyclopropyl, cyclopropylcarbonyl, or cyclopropylmethyl; or represents optionally cyano-, nitro-, fluorine-, chlorine-, bromine-, methyl-, ethyl-, n- or i-propyl-, n-, s-, or t-butyl-, trifluoromethyl-, methoxy-, ethoxy-, s- or i-propoxy-, difluoromethoxy-, or trifluoromethoxy-substituted phenyl, benzoyl, phenoxycarbonyl, benzyl, phenylmethylcarbonyl, or phenylmethoxycarbonyl; or R.sup.9 together with R.sup.2 and the nitrogen to which they are attached represent optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, or trifluoromethoxy-substituted pyrrolidinyl, oxopyrrolidinyl, pyrrolyl, indolyl, pyrazolyl, oxazolyl, isoxazolyl, dihydropyranyl, piperidinyl, oxopiperidinyl, morpholinyl, thiomorpholinyl, 3-oxomorpholinyl, 3-oxo-thiomorpholinyl, piperazinyl, imidazolyl, imidazolidinyl, oxo-imidazolidinyl, triazol, triazolinyl, tetrazolinyl, or pyridinyl;

$R^{10}$ represents hydrogen or formyl; represents optionally cyano-, fluorine-, chlorine-, methoxy-, ethoxy-, n- or i-propoxy-, acetyl-, propionyl-, n- or i-butyroyl-, methoxycarbonyl-, ethoxycarbonyl-, or n- or i-propoxycarbonyl-substituted methyl, ethyl, n- or i-propyl, n-, s-, or t-butyl, n-, s-, or t-pentyl; represents optionally cyano-, fluorine-, chlorine-, methoxy-, ethoxy-, or n- or i-propoxy-substituted acetyl, propionyl, n- or i-butyroyl, methoxycarbonyl, ethoxycarbonyl, n- or i-propoxycarbonyl, methylaminocarbonyl, ethylaminocarbonyl, or n- or i-propylaminocarbonyl; represents dimethylaminocarbonyl; represents optionally fluorine- and/or chlorine-substituted methylthio, ethylthio, n- or i-propylthio, n-, s-, or t-butylthio, methylsulphinyl, ethylsulphinyl, methylsulphonyl, or ethylsulphonyl; represents optionally fluorine-, chlorine-, and/or bromine-substituted propenyl, butenyl, propynyl, or butynyl; represents optionally fluorine-, chlorine-, or methyl-substituted cyclopropyl, cyclopropylcarbonyl, or cyclopropylmethyl; represents optionally nitro-, cyano-, fluorine-, chlorine-, bromine-, methyl-, ethyl-, n- or i-propyl-, n-, s-, or t-butyl-, trifluoromethyl-, methoxy-, ethoxy-, n- or i-propoxy-, difluoromethoxy-, or trifluoromethoxy-substituted phenyl, benzoyl, phenoxycarbonyl, phenylaminocarbonyl, benzyl, phenylmethylcarbonyl, or phenylmethoxycarbonyl; or represents optionally nitro-, cyano-, fluorine-, chlorine-, bromine-, methyl-, ethyl, n- or i-propyl-, n-, s-, or t-butyl-, trifluoromethyl, methoxy-, ethoxy-, n- or i-propoxy-, difluoromethoxy-, or trifluoromethoxy-substituted heterocyclyl, heterocyclylcarbonyl, or heterocyclylalkyl selected from the group consisting of furyl, furylcarbonyl, furylmethyl, thienyl, thienylcarbonyl, thienylmethyl, pyrrolidinyl, pyrrolyl, indolyl, pyrrolylmethyl, pyrazolyl, pyrazolylmethyl, isoxazolyl, piperidinyl, morpholinyl, piperazinyl, pyridinyl, and pyridinylmethyl;

X represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl, or dimethylaminosulphonyl;

Y represents hydrogen, nitro, cyano, fluorine, chlorine, bromine, iodine, methyl, ethyl, difluoromethyl, trifluoromethyl, dichloromethyl, trichloromethyl, methoxymethyl, methylthiomethyl, methylsulphinylmethyl, methylsulphonylmethyl, methoxy, ethoxy, difluoromethoxy, trifluoromethoxy, methylthio, ethylthio, methylsulphinyl, ethylsulphinyl, methylsulphonyl, ethylsulphonyl, or dimethylaminosulphonyl, and m represents the number 0 or 2.

5. A process for preparing a compound of formula (I) according to claim 1 comprising (a) reacting a carboxylic acid of formula (II)

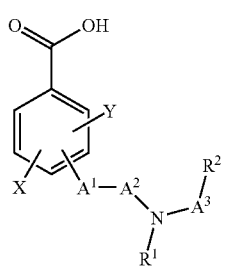

(II)

in which $A^1, A^2, A^3, R^1, R^2$, X, and Y are as defined for formula (I) in claim 1,
or an alkali metal, alkaline earth metal, or ammonium salt thereof,
with a compound of formula (III)

H—Z (III)

in which Z is as defined for formula (I) in claim 1, or (b) reacting a carboxylic acid derivative of formula (IX)

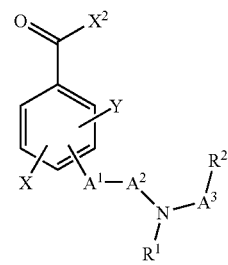

(IX)

in which
$A^1, A^2, A^3, R^1, R^2$, X, and Y are as defined for formula (I) in claim 1, and
$X^2$ represents CN, halogen, imidazolyl, or triazolyl, with a compound of formula (III)

H—Z (III)

in which Z is as defined for formula (I) in claim 1, or (c) reacting a compound of formula (XIII)

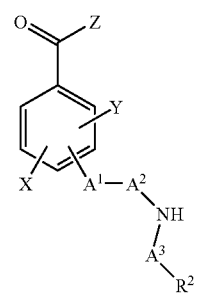

(XIII)

in which $A^1, A^2, A^3, R^1, R^2$, X, and Y are as defined for formula (I) in claim 1,
with a compound of formula (XI)

$X^1$—$R^1$ (XI)

in which $R^1$ is as defined for formula (I) in claim 1, and $X^1$ represents halogen, arylsulphonate, or alkylsulphonate, or (d) reacting a compound of formula (XIV)

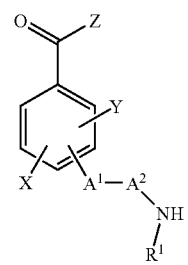

(XIV)

in which $A^1$, $A^2$, $R^1$, X, Y, and Z are as defined for formula (I) in claim 1, with a compound of formula (V)

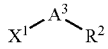

(V)

in which
A³ and R² are as defined for formula (I) in claim 1, and
X¹ represents halogen or tosylate, or (e) reacting a compound of formula (XV)

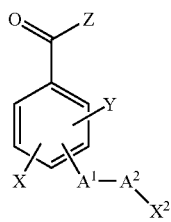

(XV)

in which
A¹, A², X, Y, and Z are as defined for formula (I) in claim 1, and
X² represents halogen or tosylate, with a compound of formula (VII)

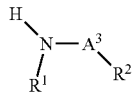

(VII)

in which A³, R¹, and R² are as defined for formula (I) in claim 1, optionally in the presence of one or more reaction auxiliaries and optionally in the presence of one or more diluents.

6. A process according to claim 5 in which in alternative (b) X² of formula (IX) represents Cl, Br, I, imidazolyl, or triazolyl.

7. A process according to claim 5 in which in alternative (c) X¹ of formula (XI) represents chlorine, bromine, iodine, mesylate, or tosylate.

8. A process according to claim 5 in which in alternative (d) X¹ of formula (V) represents chlorine, bromine, or tosylate.

9. A process according to claim 5 in which in alternative (e) X² of formula (XV) represents chlorine, bromine, or tosylate.

10. A pesticide comprising one or more compounds of formula (I) according to claim 1 and one or more extenders and/or surfactants.

11. A process for preparing a pesticide comprising mixing one or more compounds of formula (I) according to claim 1 with one or more extenders and/or surfactants.

* * * * *